US008449875B2

(12) United States Patent
Chen et al.

(10) Patent No.: US 8,449,875 B2
(45) Date of Patent: May 28, 2013

(54) TARGETING PSEUDOTYPED RETROVIRAL VECTORS

(75) Inventors: Irvin S.Y. Chen, Palos Verdes Estates, CA (US); Kouki Morizono, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/623,265

(22) Filed: Nov. 20, 2009

(65) Prior Publication Data

US 2010/0184206 A1 Jul. 22, 2010

Related U.S. Application Data

(63) Continuation of application No. 11/628,586, filed as application No. PCT/US2005/019624 on Jun. 3, 2005, now abandoned.

(60) Provisional application No. 60/577,248, filed on Jun. 3, 2004.

(51) Int. Cl.
*A01N 63/00* (2006.01)
*A61K 39/12* (2006.01)
*A61K 39/21* (2006.01)
*A61K 39/193* (2006.01)
*A61K 39/395* (2006.01)

(52) U.S. Cl.
USPC ............... 424/93.2; 424/130.1; 424/199.1; 424/207.1; 424/218.1

(58) Field of Classification Search
USPC ............ 424/93.2, 199.1, 207.1, 218.1, 130.1
See application file for complete search history.

(56) References Cited

U.S. PATENT DOCUMENTS

| 6,589,533 | B1 | 7/2003 | Brown et al. |
| 7,060,811 | B2 | 6/2006 | Aldaz et al. |
| 7,267,978 | B1 | 9/2007 | Carey et al. |
| 7,527,789 | B2 * | 5/2009 | Loibner et al. ............ 424/143.1 |

OTHER PUBLICATIONS

Lu et al., 1999, Journal of Virology, vol. 73, No. 5, p. 4272-4278.*
Gardner et al., 2000, Journal of Virology, vol. 74, No. 24, p. 11849-11857.*
Pence et al., 1990, Virology, vol. 175, No. 1, abstract.*
Maruelo, D., 2004, US 20040102410 A1.*
Dubuisson et al., 1993, Journal of Virology, vol. 67, No. 6, p. 3363-3374.*
Xu et al., 2001, US 20010055596 A1.*
Kaye et al., 1990, Proc. Natl. Acad. Sci. USA, vol. 87, pp. 6922-6926.
Morizono, Kouki et al.; "Antibody-Directed Targeting of Retroviral Vectors via Cell Surface Antigens"; 2001, *Journal of Virology*, vol. 75, No. 17, pp. 8016-8020.
Sharkey, C. Matthew et al.; "Ross River Virus Glycoprotein-Pseudotyped Retroviruses and Stable Cell Lines for Their Production"; 2001, *Journal of Virology*, vol. 75, No. 6, pp. 2653-2659.
Skolnick et al., 2000, Trends in Biotech, vol. 18, p. 34-39.
Tomasinsig et al., 2005, Current Protein and Peptide Science, vol. 6, p. 23-34.

* cited by examiner

*Primary Examiner* — Shin-Lin Chen
(74) *Attorney, Agent, or Firm* — Morgan, Lewis & Bockius LLP; Annette S. Parent

(57) ABSTRACT

The present invention provides targeted lentiviral vectors that are psuedotyped with mutated Sindbis envelopes. For example, mutations in the Sindbis E2 protein are used to alter viral titer, specificity, specificity index, tropism, and susceptibility to host immune response. Typically, one or more of the E1, E2, or E3 proteins can be mutated at one or more amino acid positions. The psuedotyped, targeted lentiviral vectors of the invention are used to transduce heterologous genes into a cell and can be used for in vivo and ex vivo therapeutic applications, as well as for diagnostic and research tool applications.

8 Claims, 18 Drawing Sheets

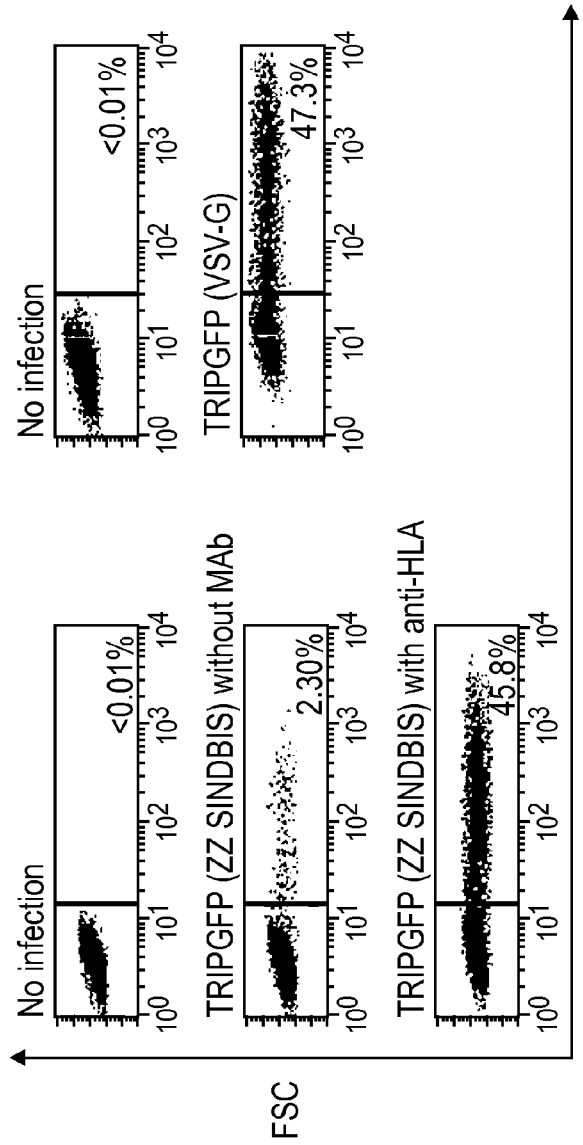
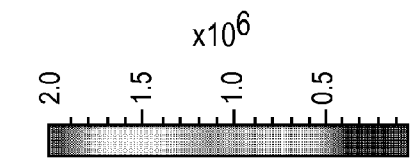
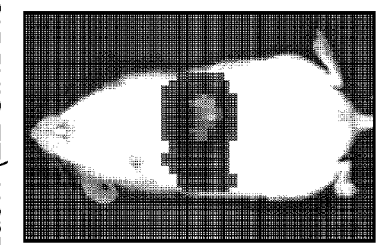
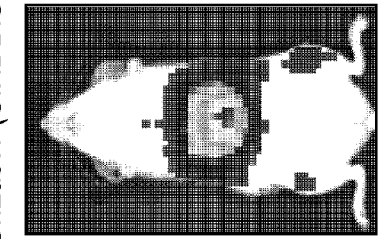
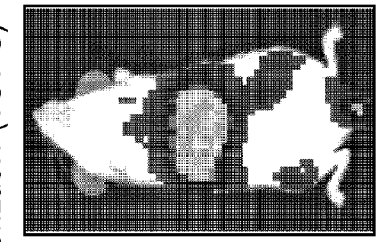
FIG. 2A
FIG. 2B

Nucleic acid sequence encoding ZZSINDBIS

```
ATGGCGTCCGCAGCACCACTGGTCACGGCAATGTGTTTGCTCGGAAATGTGAGCTTCCCATGCGACCGCCCGCCC
ACATGCTATACCCGCGAACCTTCCAGAGCCCTCGACATCCTTGAAGAGAACGTGAACCATGAGGCCTACGATACC
CTGCTCAATGCCATATTGCGGTGCGGATCGTCTGGCAGAAGCAAAAGAAGCGTCATTGACGACTTTACCCTGACC
AGCCCCTACTTGGGCACATGCTCGTACTGCCACCATACTGTACCGTGCTTCAGCCCTGTTAAGATCGAGCAGGTC
TGGGACGAAGCGGACGATAACACCATACGCATACAGACTTCCGCCCAGTTTGGATACGACCAAAGCGGAGCAGCA
AGCGCAAACAAGTACCGCTACATGTCGCTTAAGCAGGTAACCGACAACAAATTCAACAAAGAACAACAAAACGCG
TTCTATGAGATCTTACATTTACCTAACTTAAACGAAGAACAACGAAACGCCTTCATCCAAAGTTTAAAAGATGAC
CCAAGCCAAAGCGCTAACCTTTTAGCAGAAGCTAAAAAGCTAAATGATGCTCAGGCGCCGAAAGTAGACAACAAA
TTCAACAAAGAACAACAAAACGCGTTCTATGAGATCTTACATTTACCTAACTTAAACGAAGAACAACGAAACGCC
TTCATCCAAAGTTTAAAAGATGACCCAAGCCAAAGCGCTAACCTTTTAGCAGAAGCTAAAAAGCTAAATGATGCT
CAGGCGCCGAAAGTAGACGCGAATTCGAGCTCGGTACCCGGGGATCCGGTAACCACCGTTAAAGAAGGCACCATG
GATGACATCAAGATTAGCACCTCAGGACCGTGTAGAAGGCTTAGCTACAAAGGATACTTTCTCCTCGCAAAATGC
CCTCCAGGGGACAGCGTAACGGTTAGCATAGTGAGTAGCAACTCAGCAACGTCATGTACACTGGCCCGCAAGATA
AAACCAAAATTCGTGGGACGGGAAAAATATGATCTACCTCCCGTTCACGGTAAAAAAATTCCTTGCACAGTGTAC
GACCGTCTGAAAGAAACAACTGCAGGCTACATCACTATGCACAGGCCGAGACCGCACGCTTATACATCCTACCTG
GAAGAATCATCAGGGAAAGTTTACGCAAAGCCGCCATCTGGGAAGAACATTACGTATGAGTGCAAGTGCGGCGAC
TACAAGACCGGAACCGTTTCGACCCGCACCGAAATCACTGGTTGCACCGCCATCAAGCAGTGCGTCGCCTATAAG
AGCGACCAAACGAAGTGGGTCTTCAACTCACCGGACTTGATCAGACATGACGACCACACGGCCCAAGGGAAATTG
CATTTGCCTTTCAAGTTGATCCCGAGTACCTGCATGGTCCTGTTGCCCACGCGCCGAATGTAATACATGGCTTT
AAACACATCAGCCTCCAATTAGATACAGACCACTTGACATTGCTCACCACCAGGAGACTAGGGGCAAACCCGGAA
CCAACCACTGAATGGATCGTCGGAAAGACGGTCAGAAACTTCACCGTCGACCGAGATGGCCTGGAATACATATGG
GGAAATCATGAGCCAGTGAGGGTCTATGCCCAAGAGTCAGCACCAGGAGACCCTCACGGATGGCCACACGAAATA
GTACAGCATTACTACCATCGCCATCCTGTGTACACCATCTTAGCCGTCGCATCAGCTACCGTGGCGATGATGATT
GGCGTAACTGTTGCAGTGTTATGTGCCTGTAAAGCGCGCCGTGAGTGCCTGACGCCATACGCCCTGGCCCCAAAC
GCCGTAATCCCAACTTCGCTGGCACTCTTTGTGCTGCGTTAGGTCGGCCAATGCTGAAACGTTCACCGAGACCATG
AGTTACTTGTGGTCGAACAGTCAGCCGTTCTTCTGGGTCCAGTTGTGCATACCTTTGGCCGCTTTCATCGTTCTA
ATGCGCTGCTGCTCCTGCTGCCTGCCTTTTTTAGTGGTTGCCGGCGCCTACCTGGCGAAGGTAGACGCCTACGAA
CATGCGACCACTGTTCCAAATGTGCCACAGATACCGTATAAGGCACTTGTTGAAAGGGCAGGGTATGCCCCGCTC
AATTTGGAGATCACTGTCATGTCCTCGGAGGTTTTGCCTTCCACCAACCAAGAGTACATTACCTGCAAATTCACC
ACTGTGGTCCCCTCCCCAAAAATCAAATGCTGCGGCTCCTTGGAATGTCAGCCGGCCGCTCATGCAGACTATACC
TGCAAGGTCTTCGGAGGGGTCTACCCCTTTATGTGGGGAGGAGCGCAATGTTTTTGCGACAGTGAGAACAGCCAG
ATGAGTGAGGCGTACGTCGAATTGTCAGCAGATTGCGCGTCTGACCACGCGCAGGCGATTAAGGTGCACACTGCC
GCGATGAAAGTAGGACTGCGTATTGTGTACGGGAACACTACCAGTTTCCTAGATGTGTACGTGAACGGAGTCACA
CCAGGAACGTCTAAAGACTTGAAAGTCATAGCTGGACCAATTTCAGCATCGTTTACGCCATTCGATCATAAGGTC
GTTATCCATCGCGGCCTGGTGTACAACTATGACTTCCCGGAATATGGAGCGATGAAACCAGGAGCGTTTGGAGAC
ATTCAAGCTACCTCCTTGACTAGCAAGGATCTCATCGCCAGCACAGACATTAGGCTACTCAAGCCTTCCGCCAAG
AACGTGCATGTCCCGTACACGCAGGCCTCATCAGGATTTGAGATGTGGAAAAACAACTCAGGCCGCCCACTGCAG
GAAACCGCACCTTTCGGGTGTAAGATTGCAGTAAATCCGCTCCGAGCGGTGGACTGTTCATACGGGAACATTCCC
ATTTCTATTGACATCCCGAACGCTGCCTTTATCAGGACATCAGATGCACCACTGGTCTCAACAGTCAAATGTGAA
GTCAGTGAGTGCACTTATTCAGCAGACTTCGGCGGGATGGCCACCCTGCAGTATGTATCCGACCGCGAAGGTCAA
TGCCCCGTACATTCGCATTCGAGCACAGCAACTCTCCAAGAGTCGACAGTACATGTCCTGGAGAAAGGAGCGGTG
ACAGTACACTTTAGCACCGCGAGTCCACAGGCGAACTTTATCGTATCGCTGTGTGGGAAGAAGACAACATGCAAT
GCAGAATGTAAACCACCAGCTGACCATATCGTGAGCACCCCGCACAAAAATGACCAAGAATTTCAAGCCGCCATC
TCAAAAACATCATGGAGTTGGCTGTTTGCCCTTTTCGGCGGCGCCTCGTCGCTATTAATTATAGGACTTATGATT
TTTGCTTGCAGCATGATGCTGACTAGCACACGAAGATGA
```

FIG. 8

Nucleic acid sequence encoding m168

```
ATGGCGTCCGCAGCACCACTGGTCACGGCAATGTGTTTGCTCGGAAATGTGAGCTTCCCATGCGACCGCCCGCCC
ACATGCTATACCCGCGAACCTTCCAGAGCCCTCGACATCCTTGAAGAGAACGTGAACCATGAGGCCTACGATACC
CTGCTCAATGCCATATTGCGGTGCGGATCGTCTGGCAGCGTCATTGACGACTTTACCCTGACCAGCCCCTACTTG
GGCACATGCTCGTACTGCCACCATACTGTACCGTGCTTCAGCCCTGTTAAGATCGAGCAGGTCTGGGACGAAGCG
GACGATAACACCATACGCATACAGACTTCCGCCCAGTTTGGATACGACCAAAGCGGAGCAGCAAGCGCAAACAAG
TACCGCTACATGGCGGCTGCGGCGGTAACCGACAACAAATTCAACAAAGAACAACAAAACGCGTTCTATGAGATC
TTACATTTACCTAACTTAAACGAAGAACAACGAAACGCCTTCATCCAAAGTTTAAAAGATGACCCAAGCCAAAGC
GCTAACCTTTTAGCAGAAGCTAAAAAGCTAAATGATGCTCAGGCGCCGAAAGTAGACAACAAATTCAACAAAGAA
CAACAAAACGCGTTCTATGAGATCTTACATTTACCTAACTTAAACGAAGAACAACGAAACGCCTTCATCCAAAGT
TTAAAAGATGACCCAAGCCAAAGCGCTAACCTTTTAGCAGAAGCTAAAAAGCTAAATGATGCTCAGGCGCCGAAA
GTAGACGCGAATTCGAGCTCGGTACCCGGGGATCCGGTAACCACCGTTAAAGAAGGCACCATGGATGACATCAAG
ATTAGCACCTCAGGACCGTGTAGAAGGCTTAGCTACAAAGGATACTTTCTCCTCGCAAATGCCCTCCAGGGGAC
AGCGTAACGGTTAGCATAGTGAGTAGCAACTCAGCAACGTCATGTACACTGGCCCGCAAGATAAAACCAAAATTC
GTGGGACGGGAAAAATATGATCTACCTCCCGTTCACGGTAAAAAAATTCCTTGCACAGTGTACGACCGTCTGGCA
GCAACAACTGCAGGCTACATCACTATGCACAGGCCGAGACCGCACGCTTATACATCCTACCTGGAAGAATCATCA
GGGAAAGTTTACGCAAAGCCGCCATCTGGGAAGAACATTACGTATGAGTGCAAGTGCGGCGACTACAAGACCGGA
ACCGTTTCGACCCGCACCGAAATCACTGGTTGCACCGCCATCAAGCAGTGCGTCGCCTATAAGAGCGACCAAACG
AAGTGGGTCTTCAACTCACCGGACTTGATCAGACATGACGACCACACGGCCCAAGGGAAATTGCATTTGCCTTTC
AAGTTGATCCCGAGTACCTGCATGGTCCCTGTTGCCCACGCGCCGAATGTAATACATGGCTTTAAACACATCAGC
CTCCAATTAGATACAGACCACTTGACATTGCTCACCACCAGGAGACTAGGGGCAAACCCGGAACCAACCACTGAA
TGGATCGTCGGAAAGACGGTCAGAAACTTCACCGTCGACCGAGATGGCCTGGAATACATATGGGGAAATCATGAG
CCAGTGAGGGTCTATGCCCAAGAGTCAGCACCAGGAGACCCTCACGGATGGCCACACGAAATAGTACAGCATTAC
TACCATCGCCATCCTGTGTACACCATCTTAGCCGTCGCATCAGCTACCGTGGCGATGATGATTGGCGTAACTGTT
GCAGTGTTATGTGCCTGTAAAGCGCGCCGTGAGTGCCTGACGCCATACGCCCTGGCCCCAAACGCCGTAATCCCA
ACTTCGCTGGCACTCTTGTGCTGCGTTAGGTCGGCCAATGCTGAAACGTTCACCGAGACCATGAGTTACTTGTGG
TCGAACAGTCAGCCGTTCTTCTGGGTCCAGTTGTGCATACCTTTGGCCGCTTTCATCGTTCTAATGCGCTGCTGC
TCCTGCTGCCTGCCTTTTTTAGTGGTTGCCGGCGCCTACCTGGCGAAGGTAGACGCCTACGAACATGCGACCACT
GTTCCAAATGTGCCACAGATACCGTATAAGGCACTTGTTGAAAGGGCAGGGTATGCCCCGCTCAATTTGGAGATC
ACTGTCATGTCCTCGGAGGTTTTGCCTTCCACCAACCAAGAGTACATTACCTGCAAATTCACCACTGTGGTCCCC
TCCCCAAAAATCAAATGCTGCGGCTCCTTGGAATGTCAGCCGGCCGCTCATGCAGACTATACCTGCAAGGTCTTC
GGAGGGGTCTACCCCTTTATGTGGGGAGGAGCGCAATGTTTTTGCGACAGTGAGAACAGCCAGATGAGTGAGGCG
TACGTCGAATTGTCAGCAGATTGCGCGTCTGACCACGCGCAGGCGATTAAGGTGCACACTGCCGCGATGAAAGTA
GGACTGCGTATTGTGTACGGGAACACTACCAGTTTCCTAGATGTGTACGTGAACGGAGTCACACCAGGAACGTCT
AAAGACTTGAAAGTCATAGCTGGACCAATTTCAGCATCGTTTACGCCATTCGATCATAAGGTCGTTATCCATCGC
GGCCTGGTGTACAACTATGACTTCCCGGAATATGGAGCGATGAAACCAGGAGCGTTTGGAGACATTCAAGCTACC
TCCTTGACTAGCAAGGATCTCATCGCCAGCACAGACATTAGGCTACTCAAGCCTTCCGCCAAGAACGTGCATGTC
CCGTACACGCAGGCCTCATCAGGATTTGAGATGTGGAAAAACAACTCAGGCCGCCCACTGCAGGAAACCGCACCT
TTCGGGTGTAAGATTGCAGTAAATCCGCTCCGAGCGGTGGACTGTTCATACGGGAACATTCCCATTTCTATTGAC
ATCCCGAACGCTGCCTTTATCAGGACATCAGATGCACCACTGGTCTCAACAGTCAAATGTGAAGTCAGTGAGTGC
ACTTATTCAGCAGACTTCGGCGGATGGCCACCCTGCAGTATGTATCCGACCGCGAAGGTCAATGCCCCGTACAT
TCGCATTCGAGCACAGCAACTCTCCAAGAGTCGACAGTACATGTCCTGGAGAAAGGAGCGGTGACAGTACACTTT
AGCACCGCGAGTCCACAGGCGAACTTTATCGTATCGCTGTGTGGGAAGAAGACAACATGCAATGCAGAATGTAAA
CCACCAGCTGACCATATCGTGAGCACCCCGCACAAAAATGACCAAGAATTTCAAGCCGCCATCTCAAAAACATCA
TGGAGTTGGCTGTTTGCCCTTTTCGGCGGCGCCTCGTCGCTATTAATTATAGGACTTATGATTTTTGCTTGCAGC
ATGATGCTGACTAGCACACGAAGATGA
```

FIG. 9

FIG. 10A
HE staining
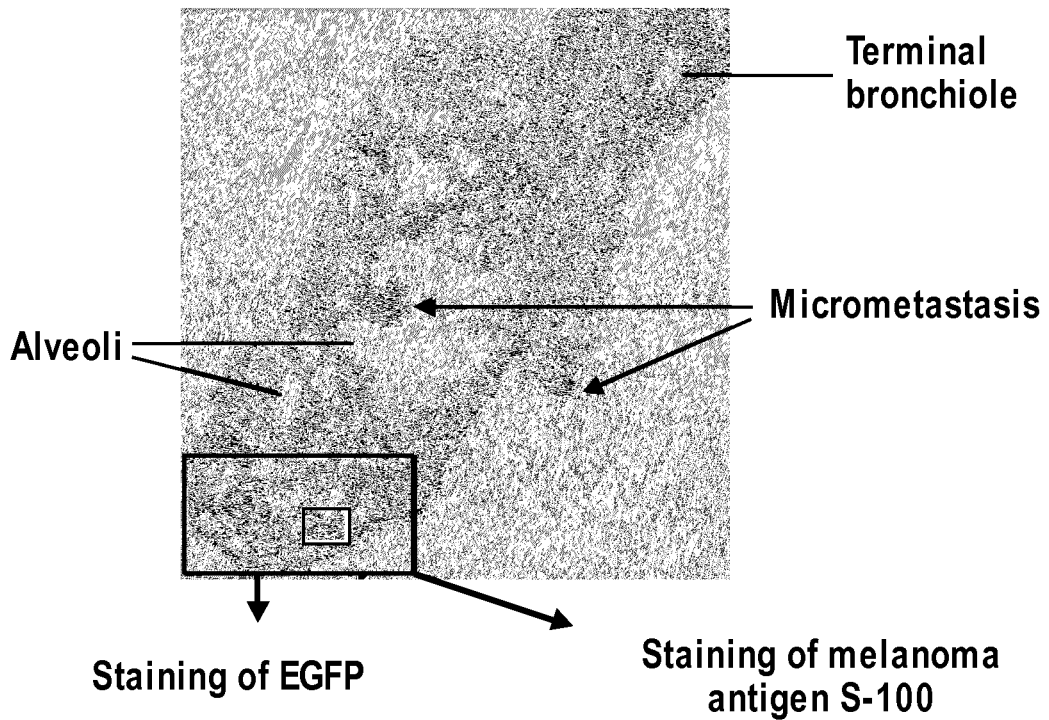
Terminal bronchiole
Alveoli
Micrometastasis
Staining of EGFP
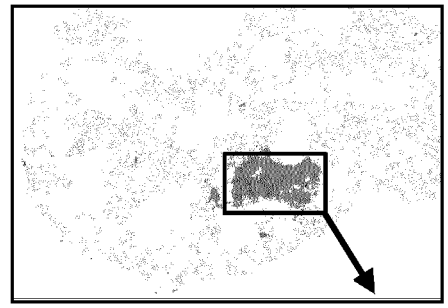
FIG. 10B
Staining of melanoma antigen S-100
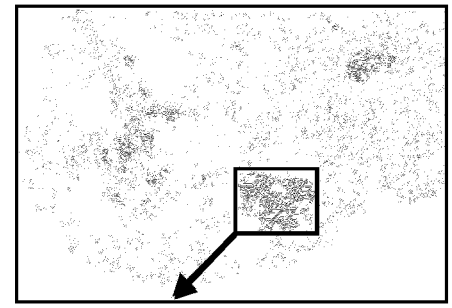
FIG. 10C
HE staining
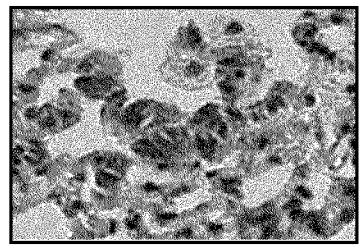
FIG. 10D

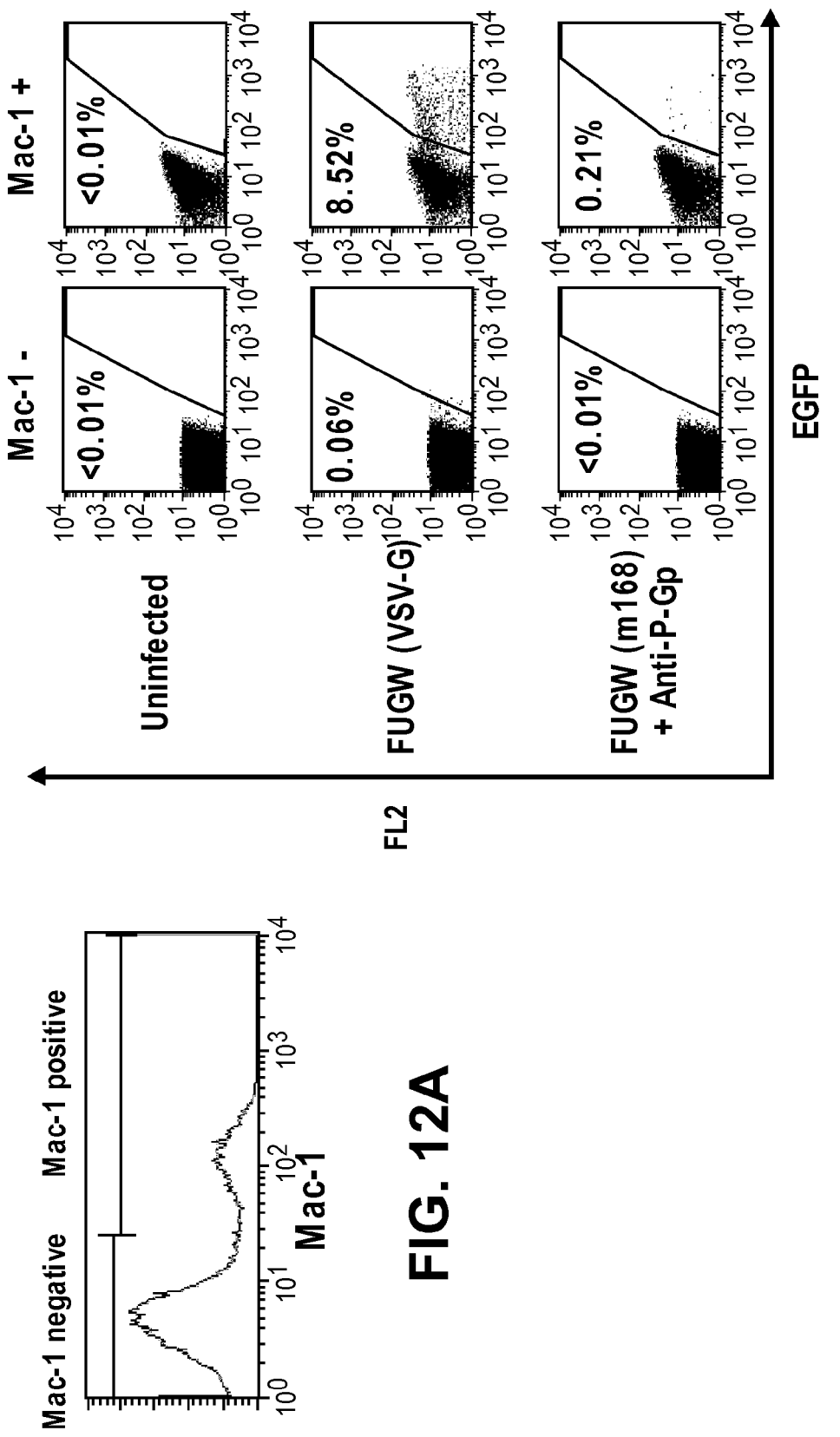

United States Patent

SEQUENCE LISTING

<160> NUMBER OF SEQ ID NOS: 16

<210> SEQ ID NO 1
<211> LENGTH: 3339
<212> TYPE: DNA
<213> ORGANISM: Sindbis virus
<220> FEATURE:
<223> OTHER INFORMATION: ZZSINBIS Sindbis virus ZZ envelope protein mutant -continued

```
<400> SEQUENCE: 1
atggcgtccg cagcaccact ggtcacggca atgtgtttgc tcggaaatgt gagcttccca      60
tgcgaccgcc cgcccacatg ctatacccgc gaaccttcca gagccctcga catccttgaa     120
gagaacgtga accatgaggc ctacgatacc ctgctcaatg ccatattgcg gtgcggatcg     180
tctggcagaa gcaaaagaag cgtcattgac gactttaccc tgaccagccc ctacttgggc     240
acatgctcgt actgccacca tactgtaccg tgcttcagcc ctgttaagat cgagcaggtc     300
tgggacgaag cggacgataa caccatacgc atacagactt ccgcccagtt tggatacgac     360
caaagcggag cagcaagcgc aaacaagtac cgctacatgt cgcttaagca ggtaaccgac     420
aacaaattca caaagaaca acaaaacgcg ttctatgaga tcttacattt acctaactta     480
aacgaagaac aacgaaacgc cttcatccaa agtttaaaag atgacccaag ccaaagcgct     540 aacctttag cagaagctaa aaagctaaat gatgctcagg cgccgaaagt agacaacaaa     600
ttcaacaaag aacaacaaaa cgcgttctat gagatcttac atttacctaa cttaaacgaa     660
gaacaacgaa acgccttcat ccaaagttta aaagatgacc caagccaaag cgctaacctt     720
ttagcagaag ctaaaaagct aaatgatgct caggcgccga agtagacgc gaattcgagc     780 tcggtacccg gggatccggt aaccaccgtt aaagaaggca ccatggatga catcaagatt     840
agcacctcag gaccgtgtag aaggcttagc tacaaaggat actttctcct cgcaaaatgc     900
cctccagggg acagcgtaac ggttagcata gtgagtagca actcagcaac gtcatgtaca     960
ctggcccgca agataaaacc aaaattcgtg ggacgggaaa aatatgatct acctcccgtt    1020
cacggtaaaa aaattccttg cacagtgtac gaccgtctga agaaacaac tgcaggctac    1080 atcactatgc acaggccgag accgcacgct tatacatcct acctggaaga tcatcagggg   1140
aaagtttacg caaagccgcc atctgggaag aacattacgt atgagtgcaa gtgcggcgac   1200
tacaagaccg gaaccgtttc gacccgcacc gaaatcactg gttgcaccgc catcaagcag   1260
tgcgtcgcct ataagagcga ccaaacgaag tgggtcttca actcaccgga cttgatcaga   1320
catgacgacc acacggccca agggaaattg catttgcctt tcaagttgat cccgagtacc   1380
tgcatggtcc ctgttgccca cgcgccgaat gtaatacatg ctttaaaca catcagcctc   1440 caattagata cagaccactt gacattgctc accaccagga gactaggggc aaacccggaa   1500
ccaaccactg aatggatcgt cggaaagacg gtcagaaact tcaccgtcga ccgagatggc   1560
ctggaataca tatggggaaa tcatgagcca gtgagggtct atgcccaaga gtcagcacca   1620
ggagaccctc acggatggcc acacgaaata gtacagcatt actaccatcg ccatcctgtg   1680
tacaccatct tagccgtcgc atcagctacc gtggcgatga tgattggcgt aactgttgca   1740
gtgttatgtg cctgtaaagc gcgccgtgag tgcctgacgc catacgccct ggccccaaac   1800
gccgtaatcc caacttcgct ggcactcttg tgctgcgtta ggtcggccaa tgctgaaacg    1860
ttcaccgaga ccatgagtta cttgtggtcg aacagtcagc cgttcttctg ggtccagttg    1920 tgcataccttt ggccgctttt catcgttcta atgcgctgct gctcctgctg cctgccttt    1980 ttagtggttg ccggcgccta cctggcgaag gtagacgcct acgaacatgc gaccactgtt    2040
ccaaatgtgc cacagatacc gtataaggca cttgttgaaa gggcaggta tgccccgctc    2100 aatttggaga tcactgtcat gtcctcggag gttttgcctt ccaccaacca agagtacatt    2160
acctgcaaat tcaccactgt ggtcccctcc ccaaaaatca atgctgcgg ctccttggaa    2220 tgtcagccgg ccgctcatgc agactatacc tgcaaggtct cggagggggt ctaccccttt    2280
atgtggggag gagcgcaatg ttttttgcgac agtgagaaca gccagatgag tgaggcgtac    2340
```

-continued

```
gtcgaattgt cagcagattg cgcgtctgac cacgcgcagg cgattaaggt gcacactgcc    2400
gcgatgaaag taggactgcg tattgtgtac gggaacacta ccagtttcct agatgtgtac    2460
gtgaacggag tcacaccagg aacgtctaaa gacttgaaag tcatagctgg accaatttca    2520
gcatcgttta cgccattcga tcataaggtc gttatccatc gcggcctggt gtacaactat    2580
gacttcccgg aatatggagc gatgaaacca ggagcgtttg agacattca  agctacctcc    2640 ttgactagca aggatctcat cgccagcaca gacattaggc tactcaagcc ttccgccaag    2700
aacgtgcatg tcccgtacac gcaggcctca tcaggatttg agatgtggaa aaacaactca    2760
ggccgcccac tgcaggaaac cgcaccttc  gggtgtaaga ttgcagtaaa tccgctccga    2820
gcggtggact gttcatacgg gaacattccc atttctattg catcccgaa  cgctgccttt    2880 atcaggacat cagatgcacc actggtctca acagtcaaat gtgaagtcag tgagtgcact    2940
tattcagcag acttcggcgg gatggccacc ctgcagtatg tatccgaccg cgaaggtcaa    3000
tgccccgtac attcgcattc gagcacagca actctccaag agtcgacagt acatgtcctg    3060
gagaaaggag cggtgacagt acactttagc accgcgagtc cacaggcgaa ctttatcgta    3120
tcgctgtgtg ggaagaagac aacatgcaat gcagaatgta aaccaccagc tgaccatatc    3180
gtgagcaccc cgcacaaaaa tgaccaagaa tttcaagccg ccatctcaaa aacatcatgg    3240
agttggctgt ttgcccttt  cggcggcgcc tcgtcgctat taattatagg acttatgatt    3300
tttgcttgca gcatgatgct gactagcaca cgaagatga                           3339
```

<210> SEQ ID NO 2
<211> LENGTH: 1112
<212> TYPE: PRT
<213> ORGANISM: Sindbis virus
<220> FEATURE:
<223> OTHER INFORMATION: ZZSINDBIS Sindbis virus ZZ envelope protein mutant

<400> SEQUENCE: 2

```
Met Ala Ser Ala Ala Pro Leu Val Thr Ala Met Cys Leu Leu Gly Asn
  1               5                  10                  15

Val Ser Phe Pro Cys Asp Arg Pro Pro Thr Cys Tyr Thr Arg Glu Pro
             20                  25                  30

Ser Arg Ala Leu Asp Ile Leu Glu Glu Asn Val Asn His Glu Ala Tyr
         35                  40                  45

Asp Thr Leu Leu Asn Ala Ile Leu Arg Cys Gly Ser Ser Gly Arg Ser
     50                  55                  60

Lys Arg Ser Val Ile Asp Asp Phe Thr Leu Thr Ser Pro Tyr Leu Gly
 65                  70                  75                  80

Thr Cys Ser Tyr Cys His His Thr Val Pro Cys Phe Ser Pro Val Lys
                 85                  90                  95

Ile Glu Gln Val Trp Asp Glu Ala Asp Asp Asn Thr Ile Arg Ile Gln
            100                 105                 110

Thr Ser Ala Gln Phe Gly Tyr Asp Gln Ser Gly Ala Ala Ser Ala Asn
        115                 120                 125

Lys Tyr Arg Tyr Met Ser Leu Lys Gln Val Thr Asp Asn Lys Phe Asn
    130                 135                 140

Lys Glu Gln Gln Asn Ala Phe Tyr Glu Ile Leu His Leu Pro Asn Leu
145                 150                 155                 160

Asn Glu Glu Gln Arg Asn Ala Phe Ile Gln Ser Leu Lys Asp Asp Pro
                165                 170                 175

Ser Gln Ser Ala Asn Leu Leu Ala Glu Ala Lys Lys Leu Asn Asp Ala
```

-continued

```
                180                 185                 190
Gln Ala Pro Lys Val Asp Asn Lys Phe Asn Lys Glu Gln Gln Asn Ala
            195                 200                 205

Phe Tyr Glu Ile Leu His Leu Pro Asn Leu Asn Glu Glu Gln Arg Asn
210                 215                 220

Ala Phe Ile Gln Ser Leu Lys Asp Asp Pro Ser Gln Ser Ala Asn Leu
225                 230                 235                 240

Leu Ala Glu Ala Lys Lys Leu Asn Asp Ala Gln Ala Pro Lys Val Asp
            245                 250                 255

Ala Asn Ser Ser Val Pro Gly Asp Pro Val Thr Thr Val Lys Glu
            260                 265                 270

Gly Thr Met Asp Asp Ile Lys Ile Ser Thr Ser Gly Pro Cys Arg Arg
            275                 280                 285

Leu Ser Tyr Lys Gly Tyr Phe Leu Leu Ala Lys Cys Pro Pro Gly Asp
            290                 295                 300

Ser Val Thr Val Ser Ile Val Ser Ser Asn Ser Ala Thr Ser Cys Thr
305                 310                 315                 320

Leu Ala Arg Lys Ile Lys Pro Lys Phe Val Gly Arg Glu Lys Tyr Asp
            325                 330                 335

Leu Pro Pro Val His Gly Lys Lys Ile Pro Cys Thr Val Tyr Asp Arg
            340                 345                 350

Leu Lys Glu Thr Thr Ala Gly Tyr Ile Thr Met His Arg Pro Arg Pro
            355                 360                 365

His Ala Tyr Thr Ser Tyr Leu Glu Glu Ser Ser Gly Lys Val Tyr Ala
            370                 375                 380

Lys Pro Pro Ser Gly Lys Asn Ile Thr Tyr Glu Cys Lys Cys Gly Asp
385                 390                 395                 400

Tyr Lys Thr Gly Thr Val Ser Thr Arg Thr Glu Ile Thr Gly Cys Thr
                405                 410                 415

Ala Ile Lys Gln Cys Val Ala Tyr Lys Ser Asp Gln Thr Lys Trp Val
            420                 425                 430

Phe Asn Ser Pro Asp Leu Ile Arg His Asp Asp His Thr Ala Gln Gly
            435                 440                 445

Lys Leu His Leu Pro Phe Lys Leu Ile Pro Ser Thr Cys Met Val Pro
            450                 455                 460

Val Ala His Ala Pro Asn Val Ile His Gly Phe Lys His Ile Ser Leu
465                 470                 475                 480

Gln Leu Asp Thr Asp His Leu Thr Leu Leu Thr Thr Arg Arg Leu Gly
            485                 490                 495

Ala Asn Pro Glu Pro Thr Thr Glu Trp Ile Val Gly Lys Thr Val Arg
            500                 505                 510

Asn Phe Thr Val Asp Arg Asp Gly Leu Glu Tyr Ile Trp Gly Asn His
            515                 520                 525

Glu Pro Val Arg Val Tyr Ala Gln Glu Ser Ala Pro Gly Asp Pro His
            530                 535                 540

Gly Trp Pro His Glu Ile Val Gln His Tyr Tyr His Arg His Pro Val
545                 550                 555                 560

Tyr Thr Ile Leu Ala Val Ala Ser Ala Thr Val Ala Met Met Ile Gly
                565                 570                 575

Val Thr Val Ala Val Leu Cys Ala Cys Lys Ala Arg Arg Glu Cys Leu
            580                 585                 590

Thr Pro Tyr Ala Leu Ala Pro Asn Ala Val Ile Pro Thr Ser Leu Ala
            595                 600                 605
```

-continued

```
Leu Leu Cys Cys Val Arg Ser Ala Asn Ala Glu Thr Phe Thr Glu Thr
610                 615                 620

Met Ser Tyr Leu Trp Ser Asn Ser Gln Pro Phe Phe Trp Val Gln Leu
625                 630                 635                 640

Cys Ile Pro Leu Ala Ala Phe Ile Val Leu Met Arg Cys Cys Ser Cys
                645                 650                 655

Cys Leu Pro Phe Leu Val Val Ala Gly Ala Tyr Leu Ala Lys Val Asp
                660                 665                 670

Ala Tyr Glu His Ala Thr Thr Val Pro Asn Val Pro Gln Ile Pro Tyr
            675                 680                 685

Lys Ala Leu Val Glu Arg Ala Gly Tyr Ala Pro Leu Asn Leu Glu Ile
690                 695                 700

Thr Val Met Ser Ser Glu Val Leu Pro Ser Thr Asn Gln Glu Tyr Ile
705                 710                 715                 720

Thr Cys Lys Phe Thr Thr Val Pro Ser Pro Lys Ile Lys Cys Cys
                725                 730                 735

Gly Ser Leu Glu Cys Gln Pro Ala Ala His Ala Asp Tyr Thr Cys Lys
                740                 745                 750

Val Phe Gly Gly Val Tyr Pro Phe Met Trp Gly Gly Ala Gln Cys Phe
                755                 760                 765

Cys Asp Ser Glu Asn Ser Gln Met Ser Glu Ala Tyr Val Glu Leu Ser
770                 775                 780

Ala Asp Cys Ala Ser Asp His Ala Gln Ala Ile Lys Val His Thr Ala
785                 790                 795                 800

Ala Met Lys Val Gly Leu Arg Ile Val Tyr Gly Asn Thr Thr Ser Phe
                805                 810                 815

Leu Asp Val Tyr Val Asn Gly Val Thr Pro Gly Thr Ser Lys Asp Leu
                820                 825                 830

Lys Val Ile Ala Gly Pro Ile Ser Ala Ser Phe Thr Pro Phe Asp His
                835                 840                 845

Lys Val Val Ile His Arg Gly Leu Val Tyr Asn Tyr Asp Phe Pro Glu
850                 855                 860

Tyr Gly Ala Met Lys Pro Gly Ala Phe Gly Asp Ile Gln Ala Thr Ser
865                 870                 875                 880

Leu Thr Ser Lys Asp Leu Ile Ala Ser Thr Asp Ile Arg Leu Leu Lys
                885                 890                 895

Pro Ser Ala Lys Asn Val His Val Pro Tyr Thr Gln Ala Ser Ser Gly
                900                 905                 910

Phe Glu Met Trp Lys Asn Asn Ser Gly Arg Pro Leu Gln Glu Thr Ala
                915                 920                 925

Pro Phe Gly Cys Lys Ile Ala Val Asn Pro Leu Arg Ala Val Asp Cys
930                 935                 940

Ser Tyr Gly Asn Ile Pro Ile Ser Ile Asp Ile Pro Asn Ala Ala Phe
945                 950                 955                 960

Ile Arg Thr Ser Asp Ala Pro Leu Val Ser Thr Val Lys Cys Glu Val
                965                 970                 975

Ser Glu Cys Thr Tyr Ser Ala Asp Phe Gly Gly Met Ala Thr Leu Gln
                980                 985                 990

Tyr Val Ser Asp Arg Glu Gly Gln Cys Pro Val His Ser His Ser Ser
                995                 1000                1005

Thr Ala Thr Leu Gln Glu Ser Thr Val His Val Leu Glu Lys Gly Ala
    1010                1015                1020

Val Thr Val His Phe Ser Thr Ala Ser Pro Gln Ala Asn Phe Ile Val
1025                1030                1035                1040
```

```
Ser Leu Cys Gly Lys Lys Thr Thr Cys Asn Ala Glu Cys Lys Pro Pro
            1045                1050                1055
Ala Asp His Ile Val Ser Thr Pro His Lys Asn Asp Gln Glu Phe Gln
        1060                1065                1070
Ala Ala Ile Ser Lys Thr Ser Trp Ser Trp Leu Phe Ala Leu Phe Gly
    1075                1080                1085
Gly Ala Ser Ser Leu Leu Ile Ile Gly Leu Met Ile Phe Ala Cys Ser
  1090                1095                1100
Met Met Leu Thr Ser Thr Arg Arg
1105                1110

<210> SEQ ID NO 3
<211> LENGTH: 3327
<212> TYPE: DNA
<213> ORGANISM: Sindbis virus
<220> FEATURE:
<223> OTHER INFORMATION: m168 Sindbis virus ZZ envelope protein mutant

<400> SEQUENCE: 3
```

| | | | | | |
|---|---|---|---|---|---|
| atggcgtccg | cagcaccact | ggtcacggca | atgtgtttgc | tcggaaatgt | gagcttccca | 60 |
| tgcgaccgcc | cgcccacatg | ctatacccgc | gaaccttcca | gagccctcga | catccttgaa | 120 |
| gagaacgtga | accatgaggc | ctacgatacc | ctgctcaatg | ccatattgcg | gtgcggatcg | 180 |
| tctggcagcg | tcattgacga | ctttaccctg | accagcccct | acttgggcac | atgctcgtac | 240 |
| tgccaccata | ctgtaccgtg | cttcagccct | gttaagatcg | agcaggtctg | ggacgaagcg | 300 |
| gacgataaca | ccatacgcat | acagacttcc | gcccagtttg | gatacgacca | aagcggagca | 360 |
| gcaagcgcaa | acaagtaccg | ctacatggcg | gctgcggcgg | taaccgacaa | caaattcaac | 420 |
| aaagaacaac | aaaacgcgtt | ctatgagatc | ttacatttac | ctaacttaaa | cgaagaacaa | 480 |
| cgaaacgcct | tcatccaaag | tttaaaagat | gacccaagcc | aaagcgctaa | ccttttagca | 540 |
| gaagctaaaa | agctaaatga | tgctcaggcg | ccgaaagtag | acaacaaatt | caacaaagaa | 600 |
| caacaaaacg | cgttctatga | gatcttacat | ttacctaact | taaacgaaga | caacgaaaac | 660 |
| gccttcatcc | aaagtttaaa | agatgaccca | agccaaagcg | ctaaccttt  | agcagaagct | 720 |
| aaaaagctaa | atgatgctca | ggcgccgaaa | gtagacgcga | attcgagctc | ggtacccggg | 780 |
| gatccggtaa | ccaccgttaa | agaaggcacc | atggatgaca | tcaagattag | cacctcagga | 840 |
| ccgtgtagaa | ggcttagcta | caaaggatac | tttctcctcg | caaatgccc  | tccaggggac | 900 |
| agcgtaacgg | ttagcatagt | gagtagcaac | tcagcaacgt | catgtacact | ggcccgcaag | 960 |
| ataaaaccaa | aattcgtggg | acgggaaaaa | tatgatctac | ctcccgttca | cggtaaaaaa | 1020 |
| attccttgca | cagtgtacga | ccgtctggca | gcaacaactg | caggctacat | cactatgcac | 1080 |
| aggccgagac | cgcacgctta | tacatcctac | ctggaagaat | catcagggaa | agtttacgca | 1140 |
| aagccgccat | ctgggaagaa | cattacgtat | gagtgcaagt | gcggcgacta | caagaccgga | 1200 |
| accgtttcga | cccgcaccga | atcactggtt | gcaccgcca  | tcaagcagtg | cgtcgcctat | 1260 |
| aagagcgacc | aaacgaagtg | gtcttcaac  | tcaccggact | tgatcagaca | tgacgaccac | 1320 |
| acggcccaag | ggaaattgca | tttgcctttc | aagttgatcc | cgagtacctg | catggtccct | 1380 |
| gttgcccacg | cgccgaatgt | aatacatggc | tttaaacaca | tcagcctcca | attagataca | 1440 |
| gaccacttga | cattgctcac | caccaggaga | ctaggggcaa | acccggaacc | aaccactgaa | 1500 |
| tggatcgtcg | gaaagacggt | cagaaacttc | accgtcgacc | gagatggcct | ggaatacata | 1560 |
| tggggaaatc | atgagccagt | gagggtctat | gcccaagagt | cagcaccagg | agaccctcac | 1620 |

-continued

```
ggatggccac acgaaatagt acagcattac taccatcgcc atcctgtgta caccatctta    1680
gccgtcgcat cagctaccgt ggcgatgatg attggcgtaa ctgttgcagt gttatgtgcc    1740
tgtaaagcgc gccgtgagtg cctgacgcca tacgccctgg ccccaaacgc cgtaatccca    1800
acttcgctgg cactcttgtg ctgcgttagg tcggccaatg ctgaaacgtt caccgagacc    1860
atgagttact tgtggtcgaa cagtcagccg ttcttctggg tccagttgtg catacctttg    1920
gccgctttca tcgttctaat gcgctgctgc tcctgctgcc tgccttttt agtggttgcc    1980
ggcgcctacc tggcgaaggt agacgcctac gaacatgcga ccactgttcc aaatgtgcca    2040
cagataccgt ataaggcact tgttgaaagg cagggtatg ccccgctcaa tttggagatc    2100
actgtcatgt cctcggaggt tttgccttcc accaaccaag agtacattac ctgcaaattc    2160
accactgtgg tccctccccc aaaaatcaaa tgctgcggct ccttggaatg tcagccggcc    2220
gctcatgcag actatacctg caaggtcttc ggaggggtct acccctttat gtggggagga    2280
gcgcaatgtt tttgcgacag tgagaacagc cagatgagtg aggcgtacgt cgaattgtca    2340
gcagattgcg cgtctgacca cgcgcaggcg attaaggtgc acactgccgc gatgaaagta    2400
ggactgcgta ttgtgtacgg gaacactacc agtttcctag atgtgtacgt gaacggagtc    2460
acaccaggaa cgtctaaaga cttgaaagtc atagctggac caatttcagc atcgtttacg    2520
ccattcgatc ataaggtcgt tatccatcgc ggcctggtgt acaactatga cttcccggaa    2580
tatggagcga tgaaaccagg agcgtttgga gacattcaag ctacctcctt gactagcaag    2640
gatctcatcg ccagcacaga cattaggcta ctcaagcctt ccgccaagaa cgtgcatgtc    2700
ccgtacacgc aggcctcatc aggatttgag atgtggaaaa acaactcagg ccgcccactg    2760
caggaaaccg cacctttcgg gtgtaagatt gcagtaaatc cgctccgagc ggtggactgt    2820
tcatacggga acattcccat ttctattgac atcccgaacg ctgcctttat caggacatca    2880
gatgcaccac tggtctcaac agtcaaatgt gaagtcagtg agtgcactta ttcagcagac    2940
ttcggcggga tggccaccct gcagtatgta tccgaccgcg aaggtcaatg ccccgtacat    3000
tcgcattcga gcacagcaac tctccaagag tcgacagtac atgtcctgga aaaggagcg    3060
gtgacagtac actttagcac cgcgagtcca caggcgaact tatcgtatc gctgtgtggg    3120
aagaagacaa catgcaatgc agaatgtaaa ccaccagctg accatatcgt gagcacccccg    3180
cacaaaaatg accaagaatt tcaagccgcc atctcaaaaa catcatggag ttggctgttt    3240
gccctttcg gcggcgccctc gtcgctatta attataggac ttatgatttt tgcttgcagc    3300
atgatgctga ctagcacacg aagatga                                        3327
```

<210> SEQ ID NO 4
<211> LENGTH: 1108
<212> TYPE: PRT
<213> ORGANISM: Sindbis virus
<220> FEATURE:
<223> OTHER INFORMATION: m168 Sindbis virus ZZ envelope protein mutant

<400> SEQUENCE: 4

```
Met Ala Ser Ala Ala Pro Leu Val Thr Ala Met Cys Leu Leu Gly Asn
 1               5                  10                  15

Val Ser Phe Pro Cys Asp Arg Pro Pro Thr Cys Tyr Thr Arg Glu Pro
             20                  25                  30

Ser Arg Ala Leu Asp Ile Leu Glu Glu Asn Val Asn His Glu Ala Tyr
         35                  40                  45

Asp Thr Leu Leu Asn Ala Ile Leu Arg Cys Gly Ser Ser Gly Ser Val
     50                  55                  60
```

```
Ile Asp Asp Phe Thr Leu Thr Ser Pro Tyr Leu Gly Thr Cys Ser Tyr
 65                  70                  75                  80

Cys His His Thr Val Pro Cys Phe Ser Pro Val Lys Ile Glu Gln Val
                 85                  90                  95

Trp Asp Glu Ala Asp Asn Thr Ile Arg Ile Gln Thr Ser Ala Gln
             100                 105                 110

Phe Gly Tyr Asp Gln Ser Gly Ala Ala Ser Ala Asn Lys Tyr Arg Tyr
             115                 120                 125

Met Ala Ala Ala Val Thr Asp Asn Lys Phe Asn Lys Glu Gln Gln
130                 135                 140

Asn Ala Phe Tyr Glu Ile Leu His Leu Pro Asn Leu Asn Glu Glu Gln
145                 150                 155                 160

Arg Asn Ala Phe Ile Gln Ser Leu Lys Asp Asp Pro Ser Gln Ser Ala
                 165                 170                 175

Asn Leu Leu Ala Glu Ala Lys Lys Leu Asn Asp Ala Gln Ala Pro Lys
             180                 185                 190

Val Asp Asn Lys Phe Asn Lys Glu Gln Gln Asn Ala Phe Tyr Glu Ile
             195                 200                 205

Leu His Leu Pro Asn Leu Asn Glu Glu Gln Arg Asn Ala Phe Ile Gln
210                 215                 220

Ser Leu Lys Asp Asp Pro Ser Gln Ser Ala Asn Leu Leu Ala Glu Ala
225                 230                 235                 240

Lys Lys Leu Asn Asp Ala Gln Ala Pro Lys Val Asp Ala Asn Ser Ser
                 245                 250                 255

Ser Val Pro Gly Asp Pro Val Thr Thr Val Lys Glu Gly Thr Met Asp
             260                 265                 270

Asp Ile Lys Ile Ser Thr Ser Gly Pro Cys Arg Arg Leu Ser Tyr Lys
             275                 280                 285

Gly Tyr Phe Leu Leu Ala Lys Cys Pro Pro Gly Asp Ser Val Thr Val
             290                 295                 300

Ser Ile Val Ser Ser Asn Ser Ala Thr Ser Cys Thr Leu Ala Arg Lys
305                 310                 315                 320

Ile Lys Pro Lys Phe Val Gly Arg Glu Lys Tyr Asp Leu Pro Pro Val
                 325                 330                 335

His Gly Lys Lys Ile Pro Cys Thr Val Tyr Asp Arg Leu Ala Ala Thr
             340                 345                 350

Thr Ala Gly Tyr Ile Thr Met His Arg Pro Arg Pro His Ala Tyr Thr
             355                 360                 365

Ser Tyr Leu Glu Glu Ser Ser Gly Lys Val Tyr Ala Lys Pro Pro Ser
370                 375                 380

Gly Lys Asn Ile Thr Tyr Glu Cys Lys Cys Gly Asp Tyr Lys Thr Gly
385                 390                 395                 400

Thr Val Ser Thr Arg Thr Glu Ile Thr Gly Cys Thr Ala Ile Lys Gln
                 405                 410                 415

Cys Val Ala Tyr Lys Ser Asp Gln Thr Lys Trp Val Phe Asn Ser Pro
             420                 425                 430

Asp Leu Ile Arg His Asp Asp His Thr Ala Gln Gly Lys Leu His Leu
             435                 440                 445

Pro Phe Lys Leu Ile Pro Ser Thr Cys Met Val Pro Val Ala His Ala
450                 455                 460

Pro Asn Val Ile His Gly Phe Lys His Ile Ser Leu Gln Leu Asp Thr
465                 470                 475                 480

Asp His Leu Thr Leu Leu Thr Thr Arg Arg Leu Gly Ala Asn Pro Glu
                 485                 490                 495
```

```
Pro Thr Thr Glu Trp Ile Val Gly Lys Thr Val Arg Asn Phe Thr Val
            500                 505                 510

Asp Arg Asp Gly Leu Glu Tyr Ile Trp Gly Asn His Glu Pro Val Arg
            515                 520                 525

Val Tyr Ala Gln Glu Ser Ala Pro Gly Asp Pro His Gly Trp Pro His
            530                 535                 540

Glu Ile Val Gln His Tyr Tyr His Arg His Pro Val Tyr Thr Ile Leu
545                 550                 555                 560

Ala Val Ala Ser Ala Thr Val Ala Met Met Ile Gly Val Thr Val Ala
            565                 570                 575

Val Leu Cys Ala Cys Lys Ala Arg Arg Glu Cys Leu Thr Pro Tyr Ala
            580                 585                 590

Leu Ala Pro Asn Ala Val Ile Pro Thr Ser Leu Ala Leu Leu Cys Cys
            595                 600                 605

Val Arg Ser Ala Asn Ala Glu Thr Phe Thr Glu Thr Met Ser Tyr Leu
            610                 615                 620

Trp Ser Asn Ser Gln Pro Phe Phe Trp Val Gln Leu Cys Ile Pro Leu
625                 630                 635                 640

Ala Ala Phe Ile Val Leu Met Arg Cys Cys Ser Cys Cys Leu Pro Phe
            645                 650                 655

Leu Val Val Ala Gly Ala Tyr Leu Ala Lys Val Asp Ala Tyr Glu His
            660                 665                 670

Ala Thr Thr Val Pro Asn Val Pro Gln Ile Pro Tyr Lys Ala Leu Val
            675                 680                 685

Glu Arg Ala Gly Tyr Ala Pro Leu Asn Leu Glu Ile Thr Val Met Ser
690                 695                 700

Ser Glu Val Leu Pro Ser Thr Asn Gln Glu Tyr Ile Thr Cys Lys Phe
705                 710                 715                 720

Thr Thr Val Val Pro Ser Pro Lys Ile Lys Cys Cys Gly Ser Leu Glu
            725                 730                 735

Cys Gln Pro Ala Ala His Ala Asp Tyr Thr Cys Lys Val Phe Gly Gly
            740                 745                 750

Val Tyr Pro Phe Met Trp Gly Gly Ala Gln Cys Phe Cys Asp Ser Glu
            755                 760                 765

Asn Ser Gln Met Ser Glu Ala Tyr Val Glu Leu Ser Ala Asp Cys Ala
            770                 775                 780

Ser Asp His Ala Gln Ala Ile Lys Val His Thr Ala Ala Met Lys Val
785                 790                 795                 800

Gly Leu Arg Ile Val Tyr Gly Asn Thr Thr Ser Phe Leu Asp Val Tyr
            805                 810                 815

Val Asn Gly Val Thr Pro Gly Thr Ser Lys Asp Leu Lys Val Ile Ala
            820                 825                 830

Gly Pro Ile Ser Ala Ser Phe Thr Pro Phe Asp His Lys Val Val Ile
            835                 840                 845

His Arg Gly Leu Val Tyr Asn Tyr Asp Phe Pro Glu Tyr Gly Ala Met
850                 855                 860

Lys Pro Gly Ala Phe Gly Asp Ile Gln Ala Thr Ser Leu Thr Ser Lys
865                 870                 875                 880

Asp Leu Ile Ala Ser Thr Asp Ile Arg Leu Leu Lys Pro Ser Ala Lys
            885                 890                 895

Asn Val His Val Pro Tyr Thr Gln Ala Ser Ser Gly Phe Glu Met Trp
            900                 905                 910

Lys Asn Asn Ser Gly Arg Pro Leu Gln Glu Thr Ala Pro Phe Gly Cys
```

-continued

```
                915                 920                 925
Lys Ile Ala Val Asn Pro Leu Arg Ala Val Asp Cys Ser Tyr Gly Asn
    930                 935                 940
Ile Pro Ile Ser Ile Asp Ile Pro Asn Ala Ala Phe Ile Arg Thr Ser
945                 950                 955                 960
Asp Ala Pro Leu Val Ser Thr Val Lys Cys Glu Val Ser Glu Cys Thr
                965                 970                 975
Tyr Ser Ala Asp Phe Gly Gly Met Ala Thr Leu Gln Tyr Val Ser Asp
            980                 985                 990
Arg Glu Gly Gln Cys Pro Val His Ser His Ser Ser Thr Ala Thr Leu
        995                 1000                1005
Gln Glu Ser Thr Val His Val Leu Glu Lys Gly Ala Val Thr Val His
    1010                1015                1020
Phe Ser Thr Ala Ser Pro Gln Ala Asn Phe Ile Val Ser Leu Cys Gly
1025                1030                1035                1040
Lys Lys Thr Thr Cys Asn Ala Glu Cys Lys Pro Pro Ala Asp His Ile
                1045                1050                1055
Val Ser Thr Pro His Lys Asn Asp Gln Glu Phe Gln Ala Ala Ile Ser
            1060                1065                1070
Lys Thr Ser Trp Ser Trp Leu Phe Ala Leu Phe Gly Gly Ala Ser Ser
        1075                1080                1085
Leu Leu Ile Ile Gly Leu Met Ile Phe Ala Cys Ser Met Met Leu Thr
    1090                1095                1100
Ser Thr Arg Arg
1105

<210> SEQ ID NO 5
<211> LENGTH: 3327
<212> TYPE: DNA
<213> ORGANISM: Sindbis virus
<220> FEATURE:
<223> OTHER INFORMATION: m168 mutant (E1 AK226-227SG) Sindbis virus ZZ
      envelope protein mutant, m168 with mutation in E1 domain

<400> SEQUENCE: 5
atggcgtccg cagcaccact ggtcacggca atgtgtttgc tcggaaatgt gagcttccca      60
tgcgaccgcc cgcccacatg ctatacccgc gaaccttcca gagccctcga catccttgaa     120
gagaacgtga accatgaggc ctacgatacc ctgctcaatg ccatattgcg gtgcggatcg     180
tctggcagcg tcattgacga ctttaccctg accagcccct acttgggcac atgctcgtac     240
tgccaccata ctgtaccgtg cttcagccct gttaagatcg agcaggtctg ggacgaagcg     300
gacgataaca ccatacgcat acagacttcc gcccagtttg atacgacca aagcggagca     360 gcaagcgcaa acaagtaccg ctacatggcg gctgcggcgg taaccgacaa caaattcaac     420
aaagaacaac aaaacgcgtt ctatgagatc ttacatttac ctaacttaaa cgaagaacaa     480
cgaaacgcct tcatccaaag tttaaaagat gacccaagcc aaagcgctaa ccttttagca     540
gaagctaaaa agctaaatga tgctcaggcg ccgaaagtag acaacaaatt caacaaagaa     600
caacaaaacg cgttctatga gatcttacat ttacctaact taaacgaaga caacgaaac      660 gccttcatcc aaagtttaaa agatgaccca agccaaagcg ctaacctttt agcagaagct     720
aaaaagctaa atgatgctca ggcgccgaaa gtagacgcga attcgagctc ggtacccggg     780
gatccggtaa ccaccgttaa agaaggcacc atggatgaca tcaagattag cacctcagga     840
ccgtgtagaa ggcttagcta caaggatac tttctcctcg caaatgccc tccagggac       900 agcgtaacgg ttagcatagt gagtagcaac tcagcaacgt catgtacact ggcccgcaag     960
```

```
ataaaaccaa aattcgtggg acgggaaaaa tatgatctac ctcccgttca cggtaaaaaa      1020
attccttgca cagtgtacga ccgtctggca gcaacaactg caggctacat cactatgcac      1080
aggccgagac cgcacgctta tacatcctac ctggaagaat catcagggaa agtttacgca      1140
aagccgccat ctgggaagaa cattacgtat gagtgcaagt gcggcgacta caagaccgga      1200
accgtttcga cccgcaccga aatcactggt tgcaccgcca tcaagcagtg cgtcgcctat      1260
aagagcgacc aaacgaagtg ggtcttcaac tcaccggact tgatcagaca tgacgaccac      1320
acggcccaag ggaaattgca tttgcctttc aagttgatcc cgagtacctg catggtccct      1380
gttgcccacg cgccgaatgt aatacatggc tttaaacaca tcagcctcca attagataca      1440
gaccacttga cattgctcac caccaggaga ctagggggcaa acccggaacc aaccactgaa      1500
tggatcgtcg gaaagacggt cagaaacttc accgtcgacc gagatggcct ggaatacata      1560
tggggaaatc atgagccagt gagggtctat gcccaagagt cagcaccagg agaccctcac      1620
ggatggccac acgaaatagt acagcattac taccatcgcc atcctgtgta caccatctta      1680
gccgtcgcat cagctaccgt ggcgatgatg attggcgtaa ctgttgcagt gttatgtgcc      1740
tgtaaagcgc gccgtgagtg cctgacgcca tacgccctgg ccccaaacgc cgtaatccca      1800
acttcgctgg cactcttgtg ctgcgttagg tcggccaatg ctgaaacgtt caccgagacc      1860
atgagttact tgtggtcgaa cagtcagccg ttcttctggg tccagttgtg catacctttg      1920
gccgctttca tcgttctaat gcgctgctgc tcctgctgcc tgccttttt agtggttgcc      1980 ggcgcctacc tggcgaaggt agacgcctac gaacatgcga ccactgttcc aaatgtgcca      2040
cagataccgt ataaggcact tgttgaaagg gcagggtatg ccccgctcaa tttggagatc      2100
actgtcatgt cctcggaggt tttgcttcc accaaccaag agtacattac ctgcaaattc      2160
accactgtgg tcccctcccc aaaaatcaaa tgctgcggct ccttggaatg tcagccggcc      2220
gctcatgcag actatacctg caaggtcttc ggaggggtct accccttat gtggggagga      2280 gcgcaatgtt tttgcgacag tgagaacagc cagatgagtg aggcgtacgt cgaattgtca      2340
gcagattgcg cgtctgacca cgcgcaggcg attaaggtgc acactgccgc gatgaaagta      2400
ggactgcgta ttgtgtacgg gaacactacc agtttcctag atgtgtacgt gaacggagtc      2460
acaccaggaa cgtctaaaga cttgaaagtc atagctggac caatttcagc atcgtttacg      2520
ccattcgatc ataaggtcgt tatccatcgc ggcctggtgt acaactatga cttcccggaa      2580
tatggagcga tgaaaccagg agcgtttgga gacattcaag ctacctcctt gactagcaag      2640
gatctcatcg ccagcacaga cattaggcta ctcaagcctt cctccgggaa cgtgcatgtc      2700
ccgtacacgc aggcctcatc aggatttgag atgtggaaaa acaactcagg ccgcccactg      2760
caggaaaccg caccttcgg gtgtaagatt gcagtaaatc cgctccgagc ggtggactgt      2820
tcatacggga acattcccat ttctattgac atcccgaacg ctgcctttat caggacatca      2880
gatgcaccac tggtctcaac agtcaaatgt gaagtcagtg agtgcactta ttcagcagac      2940
ttcggcggga tggccaccct gcagtatgta tccgaccgcg aaggtcaatg ccccgtacat      3000
tcgcattcga gcacagcaac tctccaagag tcgacagtac atgtcctgga aaaggagcg      3060 gtgacagtac actttagcac cgcgagtcca caggcgaact ttatcgtatc gctgtgtggg      3120
aagaagacaa catgcaatgc agaatgtaaa ccaccagctg accatatcgt gagcaccccg      3180
cacaaaaatg accaagaatt tcaagccgcc atctcaaaaa catcatggag ttggctgttt      3240
gcccttttcg gcggcgcctc gtcgctatta attataggac ttatgatttt tgcttgcagc      3300
atgatgctga ctagcacacg aagatga                                          3327
```

<210> SEQ ID NO 6
<211> LENGTH: 1108
<212> TYPE: PRT
<213> ORGANISM: Sindbis virus
<220> FEATURE:
<223> OTHER INFORMATION: m168 mutant (E1 AK226-227SG) Sindbis virus ZZ
      envelope protein mutant, m168 with mutation in E1 domain

<400> SEQUENCE: 6

```
Met Ala Ser Ala Ala Pro Leu Val Thr Ala Met Cys Leu Leu Gly Asn
  1               5                  10                  15

Val Ser Phe Pro Cys Asp Arg Pro Pro Thr Cys Tyr Thr Arg Glu Pro
             20                  25                  30

Ser Arg Ala Leu Asp Ile Leu Glu Glu Asn Val Asn His Glu Ala Tyr
         35                  40                  45

Asp Thr Leu Leu Asn Ala Ile Leu Arg Cys Gly Ser Ser Gly Ser Val
 50                  55                  60

Ile Asp Asp Phe Thr Leu Thr Ser Pro Tyr Leu Gly Thr Cys Ser Tyr
 65                  70                  75                  80

Cys His His Thr Val Pro Cys Phe Ser Pro Val Lys Ile Glu Gln Val
                 85                  90                  95

Trp Asp Glu Ala Asp Asp Asn Thr Ile Arg Ile Gln Thr Ser Ala Gln
                100                 105                 110

Phe Gly Tyr Asp Gln Ser Gly Ala Ala Ser Ala Asn Lys Tyr Arg Tyr
            115                 120                 125

Met Ala Ala Ala Val Thr Asp Asn Lys Phe Asn Lys Glu Gln Gln
        130                 135                 140

Asn Ala Phe Tyr Glu Ile Leu His Leu Pro Asn Leu Asn Glu Glu Gln
145                 150                 155                 160

Arg Asn Ala Phe Ile Gln Ser Leu Lys Asp Asp Pro Ser Gln Ser Ala
                165                 170                 175

Asn Leu Leu Ala Glu Ala Lys Lys Leu Asn Asp Ala Gln Ala Pro Lys
            180                 185                 190

Val Asp Asn Lys Phe Asn Lys Glu Gln Gln Asn Ala Phe Tyr Glu Ile
        195                 200                 205

Leu His Leu Pro Asn Leu Asn Glu Glu Gln Arg Asn Ala Phe Ile Gln
    210                 215                 220

Ser Leu Lys Asp Asp Pro Ser Gln Ser Ala Asn Leu Leu Ala Glu Ala
225                 230                 235                 240

Lys Lys Leu Asn Asp Ala Gln Ala Pro Lys Val Asp Ala Asn Ser Ser
                245                 250                 255

Ser Val Pro Gly Asp Pro Val Thr Thr Val Lys Glu Gly Thr Met Asp
            260                 265                 270

Asp Ile Lys Ile Ser Thr Ser Gly Pro Cys Arg Arg Leu Ser Tyr Lys
        275                 280                 285

Gly Tyr Phe Leu Leu Ala Lys Cys Pro Pro Gly Asp Ser Val Thr Val
    290                 295                 300

Ser Ile Val Ser Ser Asn Ser Ala Thr Ser Cys Thr Leu Ala Arg Lys
305                 310                 315                 320

Ile Lys Pro Lys Phe Val Gly Arg Glu Lys Tyr Asp Leu Pro Pro Val
                325                 330                 335

His Gly Lys Lys Ile Pro Cys Thr Val Tyr Asp Arg Leu Ala Ala Thr
            340                 345                 350

Thr Ala Gly Tyr Ile Thr Met His Arg Pro Arg Pro His Ala Tyr Thr
        355                 360                 365
```

Ser Tyr Leu Glu Glu Ser Ser Gly Lys Val Tyr Ala Lys Pro Pro Ser
    370                 375                 380

Gly Lys Asn Ile Thr Tyr Glu Cys Lys Cys Gly Asp Tyr Lys Thr Gly
385                 390                 395                 400

Thr Val Ser Thr Arg Thr Glu Ile Thr Gly Cys Thr Ala Ile Lys Gln
            405                 410                 415

Cys Val Ala Tyr Lys Ser Asp Gln Thr Lys Trp Val Phe Asn Ser Pro
        420                 425                 430

Asp Leu Ile Arg His Asp His Thr Ala Gln Gly Lys Leu His Leu
            435                 440                 445

Pro Phe Lys Leu Ile Pro Ser Thr Cys Met Val Pro Val Ala His Ala
    450                 455                 460

Pro Asn Val Ile His Gly Phe Lys His Ile Ser Leu Gln Leu Asp Thr
465                 470                 475                 480

Asp His Leu Thr Leu Leu Thr Thr Arg Arg Leu Gly Ala Asn Pro Glu
            485                 490                 495

Pro Thr Thr Glu Trp Ile Val Gly Lys Thr Val Arg Asn Phe Thr Val
        500                 505                 510

Asp Arg Asp Gly Leu Glu Tyr Ile Trp Gly Asn His Glu Pro Val Arg
    515                 520                 525

Val Tyr Ala Gln Glu Ser Ala Pro Gly Asp Pro His Gly Trp Pro His
530                 535                 540

Glu Ile Val Gln His Tyr Tyr His Arg His Pro Val Tyr Thr Ile Leu
545                 550                 555                 560

Ala Val Ala Ser Ala Thr Val Ala Met Met Ile Gly Val Thr Val Ala
            565                 570                 575

Val Leu Cys Ala Cys Lys Ala Arg Arg Glu Cys Leu Thr Pro Tyr Ala
        580                 585                 590

Leu Ala Pro Asn Ala Val Ile Pro Thr Ser Leu Ala Leu Leu Cys Cys
    595                 600                 605

Val Arg Ser Ala Asn Ala Glu Thr Phe Thr Glu Thr Met Ser Tyr Leu
610                 615                 620

Trp Ser Asn Ser Gln Pro Phe Phe Trp Val Gln Leu Cys Ile Pro Leu
625                 630                 635                 640

Ala Ala Phe Ile Val Leu Met Arg Cys Cys Ser Cys Cys Leu Pro Phe
            645                 650                 655

Leu Val Val Ala Gly Ala Tyr Leu Ala Lys Val Asp Ala Tyr Glu His
        660                 665                 670

Ala Thr Thr Val Pro Asn Val Pro Gln Ile Pro Tyr Lys Ala Leu Val
    675                 680                 685

Glu Arg Ala Gly Tyr Ala Pro Leu Asn Leu Glu Ile Thr Val Met Ser
690                 695                 700

Ser Glu Val Leu Pro Ser Thr Asn Gln Glu Tyr Ile Thr Cys Lys Phe
705                 710                 715                 720

Thr Thr Val Val Pro Ser Pro Lys Ile Lys Cys Cys Gly Ser Leu Glu
            725                 730                 735

Cys Gln Pro Ala Ala His Ala Asp Tyr Thr Cys Lys Val Phe Gly Gly
        740                 745                 750

Val Tyr Pro Phe Met Trp Gly Gly Ala Gln Cys Phe Cys Asp Ser Glu
    755                 760                 765

Asn Ser Gln Met Ser Glu Ala Tyr Val Glu Leu Ser Ala Asp Cys Ala
770                 775                 780

Ser Asp His Ala Gln Ala Ile Lys Val His Thr Ala Ala Met Lys Val

```
                785                 790                 795                 800
Gly Leu Arg Ile Val Tyr Gly Asn Thr Thr Ser Phe Leu Asp Val Tyr
                    805                 810                 815
Val Asn Gly Val Thr Pro Gly Thr Ser Lys Asp Leu Lys Val Ile Ala
                820                 825                 830
Gly Pro Ile Ser Ala Ser Phe Thr Pro Phe Asp His Lys Val Val Ile
                835                 840                 845
His Arg Gly Leu Val Tyr Asn Tyr Asp Phe Pro Glu Tyr Gly Ala Met
            850                 855                 860
Lys Pro Gly Ala Phe Gly Asp Ile Gln Ala Thr Ser Leu Thr Ser Lys
865                 870                 875                 880
Asp Leu Ile Ala Ser Thr Asp Ile Arg Leu Leu Lys Pro Ser Ser Gly
                885                 890                 895
Asn Val His Val Pro Tyr Thr Gln Ala Ser Ser Gly Phe Glu Met Trp
            900                 905                 910
Lys Asn Asn Ser Gly Arg Pro Leu Gln Glu Thr Ala Pro Phe Gly Cys
        915                 920                 925
Lys Ile Ala Val Asn Pro Leu Arg Ala Val Asp Cys Ser Tyr Gly Asn
    930                 935                 940
Ile Pro Ile Ser Ile Asp Ile Pro Asn Ala Ala Phe Ile Arg Thr Ser
945                 950                 955                 960
Asp Ala Pro Leu Val Ser Thr Val Lys Cys Glu Val Ser Glu Cys Thr
                965                 970                 975
Tyr Ser Ala Asp Phe Gly Gly Met Ala Thr Leu Gln Tyr Val Ser Asp
                980                 985                 990
Arg Glu Gly Gln Cys Pro Val His Ser His Ser Ser Thr Ala Thr Leu
            995                 1000                1005
Gln Glu Ser Thr Val His Val Leu Glu Lys Gly Ala Val Thr Val His
        1010                1015                1020
Phe Ser Thr Ala Ser Pro Gln Ala Asn Phe Ile Val Ser Leu Cys Gly
1025                1030                1035                1040
Lys Lys Thr Thr Cys Asn Ala Glu Cys Lys Pro Pro Ala Asp His Ile
                1045                1050                1055
Val Ser Thr Pro His Lys Asn Asp Gln Glu Phe Gln Ala Ala Ile Ser
            1060                1065                1070
Lys Thr Ser Trp Ser Trp Leu Phe Ala Leu Phe Gly Gly Ala Ser Ser
        1075                1080                1085
Leu Leu Ile Ile Gly Leu Met Ile Phe Ala Cys Ser Met Met Leu Thr
    1090                1095                1100
Ser Thr Arg Arg
1105

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence:m168
      sequence modified for mutant (E1 AK226-227SG) Sindbis virus ZZ
      envelope protein mutant, m168 with mutation in E1
      domain

<400> SEQUENCE: 7
aagccttccg ccaag                                                    15

<210> SEQ ID NO 8
<211> LENGTH: 15
```

```
<212> TYPE: DNA
<213> ORGANISM: Artificial Sequence
<220> FEATURE:
<223> OTHER INFORMATION: Description of Artificial Sequence:m168
      sequence modified in mutant (E1 AK226-227SG) Sindbis virus ZZ
      envelope protein mutant, m168 with mutation in E1
      domain

<400> SEQUENCE: 8
aagccttcct ccggg                                                     15

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence:synthetic
      integrin binding sequence "4C-RGD"

<400> SEQUENCE: 9

Cys Asp Cys Arg Gly Asp Cys Phe Cys
 1               5

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:synthetic
      integrin binding sequence "4C-RGD"

<400> SEQUENCE: 10
tgcgactgta gaggcgactg tttctgc                                        27

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence:synthetic
      transferrin receptor targeting sequence "B6"

<400> SEQUENCE: 11

Gly His Lys Ala Lys Gly Pro Arg Lys
 1               5

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:synthetic
      transferrin receptor targeting sequence "B6"

<400> SEQUENCE: 12
ggacataaag ctaagggtcc tagaaag                                        27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Fluc-a PCR
      primer for analysis of vector copy number (Firefly
      Luciferase)

<400> SEQUENCE: 13
gagatacgcc ctggttcctg                                                20
```

-continued

```
<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:Fluc-b PCR
      primer for analysis of vector copy number (Firefly
      Luciferase)

<400> SEQUENCE: 14
gcatacgacg attctgtgat ttg                                            23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:beta-actin-F
      PCR primer for analysis of cell number (mouse beta
      actin)

<400> SEQUENCE: 15
caactccatc atgaagtgtg ac                                             22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:beta-actin-R
      PCR primer for analysis of cell number (mouse beta
      actin)

<400> SEQUENCE: 16
ccacacggag tacttgcgct c                                              21
```

TARGETING PSEUDOTYPED RETROVIRAL VECTORS

CROSS-REFERENCES TO RELATED APPLICATIONS

This application is a continuation of U.S. patent application Ser. No. 11/628,586, which is a National Stage of International Application No. PCT/US2005/019624 filed Jun. 3, 2005, which claims the benefit of U.S. Provisional Patent Application No. 60/577,248, filed Jun. 3, 2004, the disclosures of which are all hereby incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant Nos. AI039975, AI069350, DK054912 awarded by the National Institutes of Health. The Government has certain rights in the invention.

FIELD OF THE INVENTION

The present invention relates to lentiviral vectors pseudotyped with Sindbis envelope and targeted to specific cell types via a targeting moiety linked to the envelope.

BACKGROUND OF THE INVENTION

Clinically effective gene therapy protocols for various diseases would ideally utilize procedures for efficient and specific targeting of therapeutic genes to affected cells while maintaining stable transduction and long term expression. This would be accomplished by direct injection into the bloodstream followed by homing of the vector to the desired target cells or organs. Thus, there have been many attempts to develop targeted gene transduction systems based upon various viral vectors. Adenovirus and adeno-associated virus vectors have been used in targeted gene delivery strategies because of their simple binding and entry mechanisms. (Nicklin and Baker, Curr Gene Ther. 2, 273-293 (2002)) Although these vectors have been used successfully in vitro, for targeting to specific cells, their usefulness in vivo has been limited by their natural tropism (Muller et al., Nat. Blotechnol. 21, 1040-1046 (2003)), especially to liver cells (Martin et al., Mol. Ther. 8, 485-494 (2003)).

Oncoretroviral- and lentiviral-based vectors have several properties that make them ideal for use in gene therapy (Sandrin et al., Curr. Top. Microbiol. Immunol. 281:137-78, 137-178 (2003)). Efficient integration of retroviral DNA into the host genome enables stable long-term transgene expression. Unlike oncoretroviral vectors, lentiviral vectors are capable of transducing non-dividing cells. The application of specific targeting with retroviral vectors has been problematic and the few studies of retroviral vector targeting in living animals are not efficient (Martin et al., Mol. Ther. 5, 269-274 (2002); Jiang and Dornburg, Gene Ther. 6, 1982-1987 (1999)). Inserting ligands, peptides or single chain antibodies into the retroviral receptor binding envelope subunit has been the most common approach used to alter and/or restrict the host range of retroviral vectors (Han et al., Proc Natl. Acad Sci U.S.A. 92, 9747-9751 (1995); Jiang et al., J. Virol. 72, 10148-10156 (1998); Marin et al., J. Virol. 70, 2957-2962 (1996); Martin et al., J. Virol. 73, 6923-6929 (1999); Nilson et al., Gene Ther. 3, 280-286 (1996); Somia et al., Proc Natl. Acad Sci U.S.A. 92, 7570-7574 (1995); Valsesia-Wittmann et al., J. Virol 68, 4609-4619 (1994)). Another approach is bridging virus vector and cells by antibodies or ligands (Boerger et al., Proc Natl. Acad Sci U.S.A. 96, 9867-9872 (1999); Roux et al., Proc Natl. Acad Sci U.S.A. 86, 9079-9083 (1989)). In general, most strategies have suffered from inconsistent specificity and low viral titers as a result of modification of the retroviral envelope (Han et al., Proc Natl. Acad Sci U.S.A. 92, 9747-9751 (1995); Marin et al., J. Virol. 70, 2957-2962 (1996); Nilson et al., Gene Ther. 3, 280-286 (1996); Somia et al., Proc Natl. Acad Sci U.S.A. 92, 7570-7574 (1995); Valsesia-Wittmann et al., J. Virol 68, 4609-4619 (1994); Kasahara et al., Science 266, 1373-1376 (1994)). The modified envelope proteins appear to have specific binding activity but low fusion activity resulting in inefficient entry into cells (Martin et al., J. Virol. 73, 6923-6929 (1999); Zhao et al., Proc Natl. Acad Sci U.S.A. 96, 4005-4010 (1999)). In the absence of specific targeting, current strategies depend upon direct injection to a localized site (Akporiaye and Hersh, Curr. Opin. Mol. Ther. 1, 443-453 (1999)) or, as in the case of the only successful treatment of a heritable disease, X-linked SCID, ex vivo isolation, purification and transduction of target hematopoietic cells (Kohn et al., Nat. Med. 1, 1017-1023 (1995); Cavazzana-Calvo et al., Science 288, 669-672 (2000)).

Sindbis virus is a member of the Alphavirus genus (Schlesinger and Schlesinger, Fundamental Virology 523-539, Raven, Philadelphia (1996)). In mature Sindbis virions the plus-stranded RNA viral genome is complexed with the capsid protein to form an icosahedral nucleocapsid surrounded by a lipid bilayer embedded with two integral membrane glycoproteins, E1 and E2, that form a heterodimer and function as a unit. E1 and E2 are anchored in the membrane independently. E2 binds to the host cell receptor. E1 can mediate membrane fusion as long as it is exposed to the low pH of the endosome and in the absence of a specific interaction with a receptor. Monoclonal antibodies capable of neutralizing virus infection are usually E2 specific, and mutation of E2 is frequently associated with altered host range and virulence. E2 can be modified substantially yet retain viral infectivity. This property of E2 has been exploited to develop Sindbis virus vectors that target specific cells (Ohno et al., Nat Biotechnol. 15, 763-767 (1997)). However, since Sindbis virus vectors are cytotoxic (Tseng et al. Systemic tumor targeting and killing by Sindbis viral vectors, Nat. Biotechnol. (2003)) and unable to stably transduce their target cells, they cannot be used where stable expression is desired.

We previously found that the Sindbis virus envelope (with E1 and E2) is able to pseudotype oncoretroviruses and lentiviruses (Morizono et al., J. Virol., September; 75 (17):8015-20. 75, 8016-8020 (2001)). We used the flexibility of the Sindbis virus E2 protein to our advantage in developing oncoretroviral and lentiviral vectors with the capacity to target specific cells. We previously reported an oncoretroviral and lentiviral gene targeting system based on antibody-mediated specific binding of a modified Sindbis virus envelope (ZZ SINDBIS) that encoded the ZZ domain of protein A. We demonstrated that monoclonal antibodies directed to cell surface antigens can be used to redirect the target specificity of these vectors when pseudotyped with the modified Sindbis envelope. Of particular note, the vectors maintained high viral titers, which could be further increased by simple ultracentrifugation.

Sindbis virus has a broad natural host range. The high-affinity laminin receptor (Wang et al., J. Virol. 66, 4992-5001 (1992)) and heparin sulfate are among the known receptors (Klimstra et al., J. Virol. 72, 7357-7366 (1998)). Their wide distribution and highly conserved nature may be in part responsible for the residual non-specific tropism observed with the ZZ SINDBIS pseudotyped vector. Accordingly, there exists a need for targeted retroviral vectors with decreased binding of endogenous receptors. The present invention fulfills this and other needs.

BRIEF SUMMARY OF THE INVENTION

In order to further reduce the natural tropism of the Sindbis virus envelope and thereby increase the specificity of targeted gene transduction in vivo, we screened a panel of E2 mutants. We identified several mutants within E2 that reduced the endogenous tropism of E2. We utilized our modified ZZ SINDBIS envelope, designated m168, and a lentiviral reporter vector to target P-glycoprotein (P-gp) expressing melanoma cells in the lungs of a murine model for metastatic melanoma. We demonstrate specific targeting of metastatic tumor cells through direct injection of the vector into the bloodstream.

The present invention therefore provides targeted lentiviral vectors that are pseudotyped with mutated Sindbis envelopes. In particular, mutations in the E2 protein and are used to alter viral titer, specificity, specificity index, tropism, and susceptibility to host immune response. The pseudotyped, targeted lentiviral vectors of the invention are used to transduce heterologous genes into a cell and can be used for in vivo and ex vivo therapeutic applications, as well as for diagnostic and research tool applications.

Accordingly, in a first aspect, the invention provides a pseudotyped, targeted retroviral vector comprising:
   a) a mutated Sindbis envelope comprising Sindbis envelope proteins E1, E2, and E3, wherein at least one of E1, E2, or E3 is mutated as compared to a wild-type sequence;
   b) a targeting moiety linked to the Sindbis envelope.

In certain embodiments, the vector further comprises a retroviral-based nucleic acid genome. In certain embodiments, the retroviral-based nucleic acid genome is a lentivirus or an oncoretrovirus genome. The genome can also optionally comprise a heterologous gene.

In certain embodiments, the vector is isolated. Typically, one or more of the E1, E2, or E3 proteins can be mutated at one or more amino acid positions. In one preferred embodiment, the vector comprises the following envelope protein mutations in comparison to wild-type Sindbis virus envelope proteins: (i) deletion of E3 amino acids 61-64; (ii) E2 KE159-160AA; and (iii) E2 SLKQ68-71AAAA (SEQ ID NOs:3-4). In a further embodiment, the vector additionally comprises the envelope protein mutation E1 AK226-227SG. The vectors can also have a protein binding domain that specifically binds a protein of interest (i.e., a targeting moiety, including an antibody, an integrin, a transferrin receptor). In certain embodiments, the targeting moiety is an antibody.

The invention further encompasses a packaging system comprising a cell comprising one or more nucleic acids encoding the pseudotyped, targeted retroviral vectors described herein. In a related aspect, the invention provides expression vectors comprising one or more nucleic acids encoding Sindbis envelope proteins E1, E2, and E3, wherein at least one of E1, E2 or E3 is mutated as compared to a wild-type sequence.

In another aspect, the invention provides methods of making the pseudotyped, targeted retroviral vectors of the invention, the methods comprising the steps of expressing in a cell one or more nucleic acids comprising Sindbis envelope proteins E1, E2, and E3. The vector can optionally comprise a nucleic acid comprising the retroviral based nucleic acid genome. The Sindbis envelope proteins E1, E2 and E3 and the retroviral-based nucleic acid genome can be encoded on the same or separate nucleic acids.

In a related aspect, the invention also provides methods of transducing cells with a heterologous gene; methods of treating or preventing a disease state; and methods of diagnosing a disease state, the methods comprising the step of contacting a cell with the pseudotyped, targeted retroviral vectors described herein. In certain embodiments the cells are contacted in vitro, ex vivo, or in vivo. The pseudotyped, targeted retroviral vectors are typically administered intravenously.

In a another aspect, the invention provides a method for delivering a pseudotyped, targeted retroviral vector across the blood brain barrier in a subject, the method comprising the step of contacting a cell with a pseudotyped, targeted retroviral vector of the present invention, wherein the targeting moiety specifically binds to a transferrin receptor.

DEFINITIONS

"Sindbis envelope," "ZZSINDBIS," and "m168" refer to a viral envelope comprising the Sindbis E1, E2, and E3 proteins. The terms "Sindbis E1 protein," "Sindbis E2 protein" and "Sindbis E3 protein" or a nucleic acid encoding "Sindbis E1 protein," "Sindbis E2 protein" and "Sindbis E3 protein" refer to nucleic acids and polypeptide polymorphic variants, alleles, mutants, and interspecies homologs that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000, or more nucleic acids, up to the full length sequence, to the nucleotide sequence of E1, E2, and/or E3; (2) bind to antibodies, e.g., polyclonal or monoclonal antibodies, raised against an immunogen comprising an amino acid sequence of an E1, E2, and/or E3 protein, and conservatively modified variants thereof; (3) specifically hybridize under stringent hybridization conditions to an anti-sense strand corresponding to a nucleic acid sequence of E1, E2, and/or E3 and conservatively modified variants thereof; (4) encode a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000, or more amino acids, to a E1, E2, and/or E3 protein. The nucleic acids and proteins of the invention include both naturally occurring or recombinant molecules, as well as point mutations, including randomly generated point mutations and those generated by site-directed mutagenesis. E1, E2, and E3 are encoded by a polyprotein, the amino acid sequence of which is provided, e.g., by Accession No. VHWVB, VHWVB2, and P03316; the nucleic acid sequence is provided, e.g., by Accession No. SVU90536 and V01403 (see also Rice & Strauss, *Proc. Nat'l Acad. Sci. USA* 78:2062-2066 (1981); and Strauss et al., *Virology* 133:92-110 (1984)). Other Togaviridae family envelopes, e.g., from the Alphavirus genus, e.g., Semliki Forest Virus, Ross River Virus, and equine encephalitis virus, can also be used to pseudotype the vectors of the invention. The envelope protein sequences for such Alphaviruses are known in the art.

"Pseudotype" refers to a virus particle, where the envelope or capsid includes heterologous viral proteins.

"Nucleic acid genome" refers to the genomic or nucleic acid component of a virus particle, which encodes the genome of the virus particle, including any proteins required for replication and/or integration of the genome, if required, and optionally a heterologous protein operably linked to a promoter, the promoter being either native to the protein or heterologous (viral or non-viral). The nucleic acid genome can be based on any virus, and have an RNA or DNA genome, either single stranded or double stranded. Preferably, the nucleic acid genome is from the family Retroviridae.

"Lentiviral vector" refers to viruses comprising nucleic acid genomes based on viruses of the Lentiviral genus of the family Retroviridae. Optionally, the vector encodes a heterologous gene.

"Retroviral vectors," as used herein, refer to viruses based on viruses of the Retroviridae family. In their wild-type form, retroviral vectors typically contain a genomic nucleic acid. The pseudotyped, targeted retroviral vectors of the invention can optionally comprise a nucleic acid genome. The vectors of the invention can also comprise a heterologous gene.

"Targeting moiety" refers to a heterologous protein linked, either covalently or non-covalently, to a pseudotyped virus particle, typically linked to an envelope protein, e.g., E1, E2, or E3. The targeting moiety binds to a protein on the cell surface of a selected cell type. Representative targeting moieties include antibodies and receptor ligands.

A viral "envelope" protein, or "Env" protein, as used herein, refers to any polypeptide sequence that resides on the surface lipid bilayer of a retroviral virion whose function is to mediate the adsorption to and the penetration of host cells susceptible to infection. A retroviral envelope is formed by a cell-derived lipid bilayer into which proteins encoded by the env region of the viral genome are inserted. Envelope proteins are typically glycoproteins and usually comprise a transmembrane (TM) and a surface (SU) component linked together by disulfide bonds. Virus structure is described in detail in, for example, Coffin, et al., *Retroviruses,* 1997, Cold Spring Harbor Laboratory Press.

A viral "capsid," as used herein, refers to the principal structural protein of the virion core derived from the central region of the Gag polyprotein. The capsid protein in a mature viral particle forms a shell surrounding the ribonucleoprotein complex that contains the genomic nucleic acid. This shell, which includes additional proteins, is also referred to as a capsid. A capsid shell can exist as a component of a virion without surrounding a genomic nucleic acid.

A "virion" refers to a retrovirus body, including the outer lipid bilayer which surrounds a capsid shell which in turn surrounds a genomic nucleic acid, when present. A virion of the invention, can, but need not, have a genomic nucleic acid.

"Mutated Sindbis envelope" refers to a point mutation, insertion, or deletion in the amino acid sequence of a wild-type Sindbis E1, E2, or E3 protein. The E1, E2, or E3 protein can have one or more mutations. In addition, combinations of mutations in E1, E2, and E3 are encompassed by the invention, e.g., mutations in E1 and E2, or in E2 and E3, or E3 and E1, or E1, E2, and E3. Exemplary wild type sequences of E1, E2, and E3 proteins from Sindbis strains include Accession No. VHWVB, VHWVB2, and P03316.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

BRIEF DESCRIPTION OF THE DRAWINGS

FIG. 2. HIV vector pseudotyped by ZZ SINDBIS has non-specific infectivity in the absence of target specific antibody in vitro and in vivo. a) 293T cells ($2\times10^5$) were infected with TRIP GFP (ZZ SINDBIS) (34 ng of HIV p24) with or without anti-HLA (1 μg/ml). For comparison of titers, cells were infected with TRIP GFP (VSV-G) (8 ng of HIV p24). Three days after infection, EGFP expression was analyzed by flow cytometry. The titers of TRIP GFP (ZZ SINDBIS) and TRIP GFP (VSV-G) with 1 μg/ml of anti-HLA were $3\times10^5$ and $1.3\times10^6$ EGFP transduction units/100 ng HIV p24. (b) FUhLucW (VSV-G) (15 pg HIV p24), FUhLucW (Sindbis) (30 μg HIV p24) and FUhLucW (ZZ SINDBIS) (30 μg HIV p24) were injected intravenously through the tail vein. Five days after injection, mice were anesthetized and injected intraperitonially with 30 mg of D-luciferin. The reporter gene (Firefly luciferase) expression was imaged using a CCCD camera for 1 min prior to imaging. The acquisition time was determined to avoid saturation of the signal.

FIG. 3. Anti-SINDBIS virus antibody blocked non-specific background infectivity of the ZZ SINDBIS pesudotyped lentiviral vector. TRIP GFP (VSV-G) (3 ng HIV p24), TRIP GFP (Sindbis) (35 ng HIV p24) and TRIP GFP (ZZ SINDBIS 103 ng HIV p24) were incubated with anti-Sindbis virus antibody (0.1% volume) or control antibody for 1 hour at 4° C. The viruses were used for infection of 293T cells ($2\times10^5$).

FIG. 4. Schematic representation of mutated domains and mutants.

FIG. 5. Analysis of the m168 mutant by flow cytometry and Western blotting. (a) 293T cells ($1\times10^5$) were infected with 200 μl of unconcentrated TRIP GFP (ZZ SINDBIS) (24 ng HIV p24) or TRIP GFP (m168) (40 ng HIV p24) with or without anti-HLA (1 μg/ml). Three days after infection, EGFP expression was analyzed by flow cytometry. (b) SDS-PAGE and Western blotting of ZZ SINDBIS and m168 pseudotyped virions. Ultracentrifuged samples of HIV vectors (FUhLucW) pseudotyped by ZZ SINDBIS or m168 were lysed and subjected to SDS-polyacrylamide gel electrophoresis and Western blotting as described in the Methods section. The amount of virus for each sample was normalized by the amount of HIV p24 antigen (5 ng/sample). Viral proteins were detected with anti-Sindbis virus mouse immune ascites fluid. The band at approximately 65 kD in the ZZ SINDBIS lane is the chimeric E2 protein. The band at approximately 75 kD in the m168 lane is chimeric E2 protein with uncleaved E3 protein.

FIG. 6. The m168 pseudotyped lentiviral vector has reduced non-specific infectivity in vivo. FUhLucW (ZZ SINDBIS) (30 μg HIV p24) and FUhLucW (m168) were each injected into 3 mice via the tail vein. Five days after injection, mice were anesthetized and injected intraperitonially with D-luciferin (30 μg). The reporter gene (Firefly luciferase) expression was imaged in the dorsal and abdominal aspects of the mice using a CCCD camera for 1 min. The acquisition time was determined to avoid saturation of the signal.

FIG. 7. The m168 pseudotyped lentiviral vector mediates antibody-directed targeted gene transduction after systemic injection into mouse. *Renilla* luciferase expressing B16F10MDR5 ($2\times10^5$ cells in 150 μl of PBS) were injected into mice via the tail vein. Thirty minutes later, FUhLucW (ZZ SINDBIS) or FUhLucW (m168) to which we had added anti P-glycoprotein monoclonal antibody or isotype (IgG2a) control antibody (10 μg/ml) was injected into the tail vein. The amount of each virus used for injection was normalized to the amount of HIV p24 (36 μg of HIV p24 in 150 μl PBS). Ten days later, the level of metastasis in the lungs of mice that had received B16F10MDR5 was investigated by CCCD imaging to determine the level of *Renilla* luciferase expression as described in the Methods section. Twelve days after cell and virus injection, virus infection was determined by imaging the expression level of Firefly luciferase reporter gene as described in the Methods section.

FIG. 8. Nucleic acid sequence encoding ZZ SINDBIS (SEQ ID NO:1).

FIG. 9. Nucleic acid sequence encoding m168 (SEQ ID NO:3).

FIG. 10. Immunohistochemical analysis of metastasized tumors targeted by FUGW (m168) with anti-P-Glycoprotein. Frozen sections were prepared from the lungs of mice injected with B16F10 MDR5 cells and FUGW (m168) plus anti-P-Glycoprotein. Serial 10 μm sections were prepared and processed. a) Slides were stained for hematoxylin-eosin (HE). b) An adjacent serial section (to that shown in (a)) was stained for transgene expression (EGFP) and nuclei (DAPI). c) Another adjacent serial section was stained for melanoma antigen (S-100) and nuclei (DAPI). d) A EGFP and S-100 positive colony stained with HE is pictured at a higher magnification to show the morphology of the colony.

FIG. 11. Confocal microscopy analysis of frozen liver sections prepared from mice which had been injected with B16F10MDR5 cells, and FUGW (VSV-G) or FUGW (m168) and anti-P-Glycoprotein. The sections were stained for Kupffer cell marker F4/80 (red) and EGFP (green).

FIG. 12. a) Flow cytometric analysis of Mac-1 expression on splenocytes of NOD/SCID mice. b) Flow cytometric analysis of EGFP expression in splenocytes isolated from mice injected with B16F10MDR5 cells, and FUGW (VSV-G) or FUGW (m168) and anti-P-Glycoprotein. The cells were stained to determine Mac-1 expression. EGFP expression in Mac-1 positive and negative population was analyzed.

FIG. 13. (a) B16F10 MDR5 cells were injected into mice via the tail vein. Twelve days later, FUhLucW (m168), to which we had added anti-P-glycoprotein monoclonal antibody or isotype control antibody, or FUhLucW (VSV-G) was injected into the tail vein. The amount of each virus used for injection was normalized to the amount of HIV p24 (2.5 μg of HIV p24 in 250 μl PBS). Fifteen days after virus injection, virus infection was determined by imaging the level of Firefly luciferase reporter gene expression. (b) The mice were sacrificed immediately after whole body imaging and each organ was isolated to image luciferase expression.

FIG. 14. Prostate cells can be targeted in vitro through the prostate stem cell antigen. LPSCA4 cells were derived from LNCaP cells after stable transfection of the prostate stem cell antigen (PSCA). $1\times10^5$ LNCaP and LPSCA4 cells were infected with FUGW pseudotyped with m168 envelope (12 ng HIV-1 p24) without Ab targeting, or with αHLA or 1G8 mAb (1G8 mAB recognizes PSCA (Saffran, et al., *Proc Natl Acad Sci* (2001) 98:2658-2663)). Three days after infection, eGFP expression was analyzed by flow cytometry (ten thousand events acquired per sample). The x-axis indicates eGFP fluorescence intensity. Percentage and mean fluorescence intensity of the positive population (R2) is indicated in each plot. Infection of LPSCA4 cells targeted with 1G8 is comparable to infection targeted with αHLA, whereas in LNCaP cells targeting with 1G8 antibody gives background levels similar to those without any antibody targeting.

FIG. 15. Transcription from the PSE-BC promoter in vitro in prostate cell lines (A) and non-prostate cell lines (B). $1\times10^5$ cells were infected with lentivirus vectors expressing eGFP under the control of the ubiquitin-C promoter (FUGW) or the PSE-BC promoter (FPGW) pseudotyped with VSV G (40 ng of HIV-1 p24). Three days after infection eGFP expression was analyzed by flow cytometry (ten thousand events acquired per sample). The x-axis indicates eGFP fluorescence intensity. Percentage and mean fluorescence intensity of the positive population (R2) is indicated in each plot. Expression from the PSE-BC promoter is comparable to ubiquitin-C promoter in prostate cell lines and up to 30 times lower in non-prostate cell lines.

Figure 16:
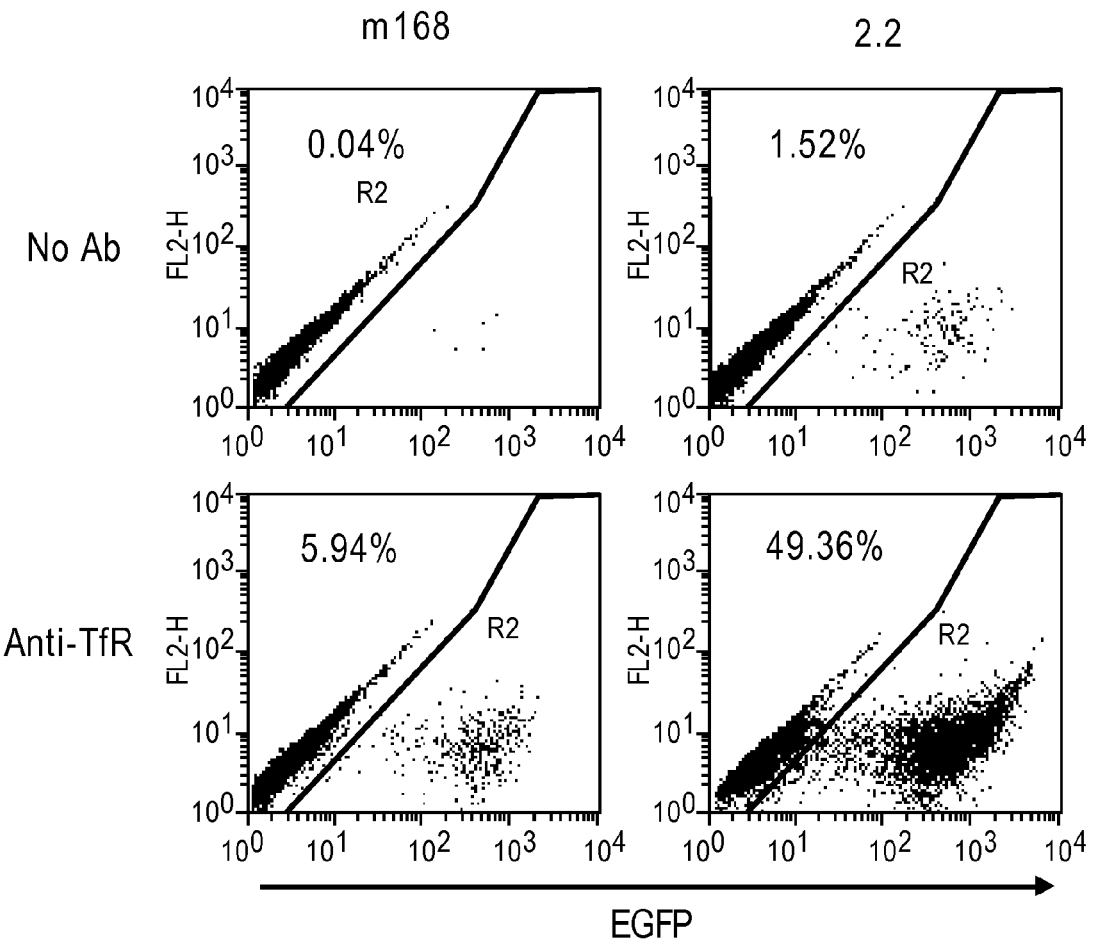

FIG. 16. New targeting envelope (2.2), comprised of m168+E1 AK226-227SG, mediated transferrin receptor (TfR) targeted gene transduction more efficiently than previous targeting envelope (m168). $4 \times 10^4$ HUVEC cells were infected with lentiviral vector (40 ng HIV-1 p24) pseudotyped with m168 envelope protein or 2.2 envelope protein with or without anti-transferrin receptor antibody (2 µg/ml). The lentiviral vector carried EGFP as reporter gene. Three days after infection, EGFP expression was analyzed by flow cytometry. The X-axis indicates EGFP fluorescence intensity. Percentage of the positive population is indicated in each plot.

Figure 17:
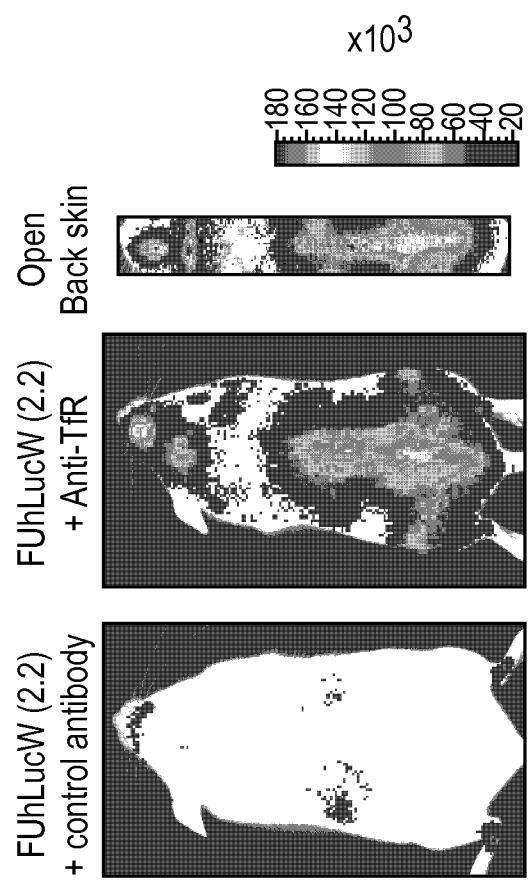

FIG. 17. Targeting envelope mediates targeted gene transduction to CNS via transferrin receptor (TfR). Lentiviral vector (3 µg HIV-1 p24) pseudotyped with 2.2 envelope protein was injected into NOD/SCID mice via the tail vein with or without anti-transferrin receptor antibody (50 µg/ml). The lentiviral vector carried Firefly luciferase as reporter gene. Five days after injection, mice were anesthetized and injected intraperitoneally with D-luciferin (30 ng). The reporter gene expression was imaged using a CCCD camera. Luciferase expression from the brain and spinal column was confirmed by removing the skin from the back after sacrifice.

DETAILED DESCRIPTION

Targeted gene transduction to specific tissues and organs via intravenous injection would be the ultimate preferred method of gene delivery. Here, we report successful targeting in a living animal via intravenous injection of a lentiviral vector pseudotyped with a modified chimeric Sindbis virus envelope. After intravenous administration into mice, the previously reported parental vector has non-specific infectivity in liver and spleen due to the residual natural tropism of Sindbis virus. Mutagenesis of domains within the Sindbis envelope ablated regions necessary for this natural tropism. M168 pseudotypes had significantly less non-specific infectivity to liver and spleen and these pseudotypes have high titer and high targeting specificity. A murine cancer model for metastatic melanoma was utilized to test specific targeting with m168. Human P-glycoprotein was ectopically expressed on the surface of melanoma cells and targeted by the m168 pseudotyped lentiviral vector conjugated with anti P-glycoprotein antibody. M168 pseudotypes successfully targeted metastatic melanoma cells growing in the lung after systemic administration via tail vein injection. This targeting technology has applications not only for cancers but also for genetic, infectious and autoimmune diseases.

The present invention therefore provides a pseudotyped virus or viral vector comprising an envelope comprising Sindbis E1, E2, and E3 proteins linked to a targeting moiety. The vector optionally further comprises a viral nucleic acid genome from the Retroviridae family, preferably the lentiviral genus. The vector can also optionally comprise a heterologous gene.

Structurally, at least one of the E1, E2, or E3 proteins has one or more mutations (preferably point mutations) in comparison to a wild type sequence in order to provide altered titer, specificity, specificity index, tropism, or host immune reaction. Combinations of mutated E1, E2, and E3 are also contemplated by the invention. Functionally, the mutated Sindbis viral envelope proteins of the present invention have a decreased ability to bind to endogenous receptors, including glycosaminoglycans (e.g., heparin sulfate). In certain embodiments, the pseudotyped virus vectors are isolated.

In certain embodiments, the pseudotyped viruses comprise one or more of the following mutations in a wild-type Sindbis or the Sindbis ZZ envelope sequence (SEQ ID NO:2): m1 (deletion of E3 amino acids 61-64), m2 (E2 R1D), m3 (m1+ m2), m4 (deletion of E2 amino acids 68-71), m5 (E2 S114 P), m6 (E2 KE159-160AA), m7 (E2 E216A T218A), m8 (E2 SLKQ68-71AAAA), m9 (E3 RSKRS60-64AAAAA), m16 (m1+m6), m17 (m1+m7), m18 (m1+m8) or E1 AK226-227SG. In one embodiment, the mutation is exemplified by the m168 sequence (SEQ ID NO:4), which comprises the mutations m1 (deletion of E3 amino acids 61-64), m6 (E2 KE159-160AA), and m8 (E2 SLKQ68-71AAAA). In another embodiment, the m168 sequence comprises a further mutation in the E1 domain that makes the m168 titer 2-10 fold higher. The sequence "aagccttccgccaag" (SEQ ID NO:7) in the sequence of m168 was modified to "aagccttcctccggg" (SEQ ID NO:8) (see SEQ ID NOs: 5 and 6). In this embodiment, the m168 sequence is further modified to eliminate cholesterol dependence for cell entry, (e.g. E1 AK226-227SG).

Mutations into one or more of the Sindbis viral envelope protein sequences can be introduced using any known methods in the art. Mutations can be targeted or random. For example, targeted mutations can be introduced using site-directed mutagenesis, for instance employing overlapping PCR or overlap extension PCR (see, for example, Aiyar, et al., *Methods Mol Biol* (1996) 57:177-91; and Pogulis, et al., *Methods Mol Biol* (1996) 57:167-76). Alternatively, mutations can be introduced by taking advantage of the error prone replication process of Sindbis viruses, which lack proof-reading and mismatch repair activities, and recombination between quasispecies in a virus population, for instance, by using a replication competent virus (see, Domingo and Holland, *Annu Rev Microbiol* (1997) 51:151-178). Mutant Sindbis virus envelope proteins of particular interest have a diminished ability to bind to endogenous receptors and therefore demonstrate decreased background infectivity in comparison to wild-type sequences. Preferably, the mutated Sindbis virus envelope proteins of the present invention have a decreased ability to bind to glycosaminoglycans (GAGs), including heparin sulfate (HS), in comparison to wild-type sequences.

The targeting moiety is covalently or non-covalently linked to the E1, E2, or E3 protein, preferably the E2 or E3 protein, or is linked to another portion of the envelope. In one embodiment, the targeting moiety is linked to E1, E2, or E3 via non-covalent interactions with a protein binding domain, where the protein binding domain is fused with E1, E2, or E3. In one embodiment, the protein binding domain is fused with E2 or E3. Exemplary protein binding domains include, e.g., the ZZ domain of protein A, streptavidin, avidin, a leucine zipper, a STAT protein N terminal domain, an FK506 binding protein, integrin binding sequence "4C-RGD" (CDCRGD-CFC (SEQ ID NO:9) encoded by tgcgactgtagaggcgact-gtttctgc (SEQ ID NO:10)), and transferrin receptor targeting sequence "B6" (GHKAKGPRK (SEQ ID NO:11) encoded by ggacataaagctaagggtcctagaaag (SEDQ ID NO:12)) (see, e.g., O'Shea, *Science* 254: 539 (1991), Barahmand-Pour et al., *Curr. Top. Microbiol. Immunol.* 211:121-128 (1996); Klemm et al., *Annu. Rev. Immunol.* 16:569-592 (1998); Klemm et al., *Annu. Rev. Immunol.* 16:569-592 (1998); Ho et al., *Nature* 382:822-826 (1996); Pomeranz et al., *Biochem.* 37:965 (1998); and Xia, et al., *J Virol* (2000) 74:11359-66). In another embodiment, the targeting moiety is a fusion protein with either the E1, E2, or E3 protein. In one embodiment, the targeting moiety is fused with the E2 or the E3 protein. The targeting moiety can be, e.g., an antibody, such as a monoclonal or single chain antibody that specifically binds to an antigen or a cell surface molecule, or a ligand or binding partner of a cell surface molecule.

The targeting moiety can target normal or diseased tissue. For example, the targeting antigen can be directed to a transferrin receptor for delivery of the present vectors across the blood-brain barrier. The targeting moiety also can be directed to marker proteins indicative of diseases including cancers (e.g., breast, lung, ovarian, prostate, colon, lymphoma, leukemia, and melanoma); autoimmune disease (e.g., myasthenia gravis, multiple sclerosis, systemic lupus erythymatosis, rheumatoid arthritis, and diabetes mellitus); infectious disease, including infection by HIV, HCV, HBV, CMV, and HPV; and genetic diseases including sickle cell anemia, cystic fibrosis, Tay-Sachs, β-thalassemia, neurofibromatosis, polycystic kidney disease, hemophilia, etc. In certain embodiments, the targeting moiety targets a cell surface antigen specific to a particular cell or tissue type, e.g., lymphocytes, myocytes, keratinocytes, neurons, hepatocytes, lung, kidney, muscle, vascular, thyroid, ocular, breast, ovarian, testis, prostate tissue.

Exemplary antigens and cell surface molecules for targeting include, e.g., P-glycoprotein, Her2/Neu, erythropoietin (EPO), epidermal growth factor receptor (EGFR), vascular endothelial growth factor receptor (VEGF-R), cadherin, carcinoembryonic antigen (CEA), CD4, CD8, CD19, CD20, CD33, CD34, CD45, CD117 (c-kit), CD133, HLA-A, HLA-B, HLA-C, chemokine receptor 5 (CCR5), stem cell marker ABCG2 transporter, ovarian cancer antigen CA125, immunoglobulins, integrins, prostate specific antigen (PSA), prostate stem cell antigen (PSCA), dendritic cell-specific intercellular adhesion molecule 3-grabbing nonintegrin (DC-SIGN), thyroglobulin, granulocyte-macrophage colony stimulating factor (GM-CSF), myogenic differentiation promoting factor-1 (MyoD-1), Leu-7 (CD57), LeuM-1, cell proliferation-associated human nuclear antigen defined by the monoclonal antibody Ki-67 (Ki-67), viral envelope proteins, HIV gp120, transferrin receptor, etc. Any cell surface protein, known in the art or yet to be identified, preferentially expressed on a particular cell or tissue type can find use as a potential target for the pseudotyped, targeted vector of the invention.

The pseudotyped, targeted vectors of the invention can optionally comprise a genomic nucleic acid. The nucleic acid genome can be from any suitable virus and in one embodiment, is derived from the Retroviridae family of viruses, e.g., from the lentiviral genus: HIV1, HIV2, SIV, FIV, BIV, Visna, CAEV, and EIAV; and from oncogenic retroviruses or oncoretroviruses, e.g., avian sarcoma/leucosis viruses (ASLV); mammalian C-type viruses (murine leukemia viruses (MuLV); feline leukemia viruses (FeLV)); B-type viruses (mouse mammary tumor viruses (MMTV); D-type viruses; and HTLV-BLV group of viruses (human T cell leukemia viruses (HTLV). Preferably, the oncogenic retroviruses lack an oncogene. Retroviruses are reviewed in Coffin, et al., *Retroviruses*, 1997, Cold Spring Harbor Laboratory Press. The nucleic acid genome is based on any suitable virus, and contains genetic components and encodes proteins so that the genome can be replicated and transcribed. However, vectors of the present invention can be replication competent or replication incompetent. In one embodiment, the nucleic acid genome is from the family Retroviridae and contains genetic components and encodes proteins so that it can be reverse transcribed and integrated into the host genome. Optionally, the genome is replication incompetent so that it cannot make productive, infectious viral particles. In certain embodiments, the genome is replication competent. Retroviral nucleic acid genomes known to those of skill in the art can be used in the invention, or made according to methods known to those of skill in the art (see, Coffin, et al, supra). Within the genome, the E1, E2, E3 and optional heterologous gene sequences can be encoded as individual polypeptides, or one or more fusion proteins. The E1, E2, E3 and optional heterologous gene sequences can be on the same or separate nucleic acid sequences. The nucleic acid genome can be RNA or DNA.

Vectors that do not comprise a genomic nucleic acid find use in the targeted delivery of a desired protein. For example, a protein to be delivered can be expressed as a fusion protein with a viral protein that is incorporated into a viral capsid. Viral proteins that are incorporated into a capsid shell, including, for example, the virion-associated regulatory proteins, viral protein r (VPR), viral protein x (VPX); and integrase, are well known in the art. See, for example, Wu, et al., *J Virol* (1995) 69:3389-98; and Katz, et al., *Virology* (1996) 217:178-90.

The genome also optionally comprises a heterologous gene operably linked to a promoter, either a viral promoter or a heterologous promoter. The heterologous gene can be a marker gene, a cytotoxic gene, a gene encoding an inhibitory sequence or protein for therapeutic applications, or a gene encoding a wild type protein for gene therapy applications. Exemplary marker genes include luciferase, a fluorescent protein (green fluorescent protein, red fluorescent protein, yellow fluorescent protein), and β-galactosidase. Exemplary cytotoxic genes include ricin, tumor necrosis factor (TNF) and apoptin. Exemplary inhibitory sequences include those that encode antisense RNA, small inhibitory RNA, oligonucleotide aptamers, and antibodies. Exemplary wild-type proteins for gene therapy applications include glial cell-derived neurotrophic factor (GDNF), Factor VIII, adenosine deaminase (ADA), hypoxanthine guanine phosphoribosyl transferase, LDL receptor, cystic fibrosis (CF) transmembrane conductance regulators (CFTR), hexosaminidase gene (HEXA), hemoglobin, β-globin, proliferative kidney disease 1 gene (PKD1) and tumor suppressor genes including neurofibromatosis gene (NF1 and NF2), breast cancer marker genes (BRCA1 and BRCA2), retinoblastoma gene (Rb), von-Hippel Lindau gene (VHL). Additional heterologous genes of use in the present invention are described in, for example, Strachan and Read, *Human Genetics 2*, $2^{nd}$ Ed., 1999, BIOS Scientific Publishers Ltd.; *Gene Therapy in Inflammatory Diseases*, Evans and Robbing, eds., 2000, Springer Verlag; *Vascular Disease: Molecular Biology and Gene Therapy Protocols*, Baker, ed., 1999, Human Press; *Cancer Gene Therapy*, Curiel and Douglas, 2005, Human Press; *Gene Therapy for Autoimmune Diseases,* 2004, Kluwer Academic Pub.; and *Progress In Gene Technology And Skin Gene Therapy: Special Issue Cells Tissues Organs* 2004, Hengge, ed., 2004, S Karger Pub.

The promoter can be a constitutive promoter (e.g., ubiquitin, actin) or an inducible promoter (e.g. metallothionein). In certain embodiments, the promoter allows for preferential expression of a heterologous gene in tissues of interest, including for example, prostate tissue (e.g., a prostate specific antigen (PSA) promoter (PSE-BC; see, Adams, et al., *Nat Med* (2002) 8:891-897; and Wu, et al., *Gene Ther* (2001) 8:1416-1426); testis tissue (Grimes, *Gene* (2004) 343:11-22; cardiovascular tissue (Beck, et al., *Curr Gene Ther* (2004) 4:457-467; breast tissue (e.g., a mammoglobin promoter; see, Goedegebuure, et al., *Curr Cancer Drug Targets* (2004) 4:531-542); thyroid tissue (e.g., a thyroglobulin promoter;

see, DeGroot, and Zhang, *Curr Drug Targets Immune Endocr Metabol Disord* (2004) 4:235-44); a gastrointestinal tissue (e.g., UDP glucuronosyltransferase promoter; see, Gregory, et al., *Toxicol Appl Pharmacol* (2004) 199:354-63); and cervical tissue (see, Rein, et al., *J. Gene Med* (2004) 6:1281-9). Tissue specific promoters of use in cancer gene therapy are reviewed in Saukkonen and Hemminki, *Expert Opin Biol Ther* (2004) 4:683-96. Tissue specific promoters of use in the gene therapy treatment of prostate cancer are reviewed in Shiradawa, et al., *Mol Urol* (2000) 4:73-82. Additional tissue specific promoters of use in the present vectors and methods include those reviewed in Hart, *Semin Oncol* (1996) 23:154-8.

Packaging cells and systems, packaging techniques and vectors for packaging the nucleic acid genome into the pseudotyped viral particle are also known to those of skill in the art and can be made according to methods known to those of skill in the art (see, for example, Polo, et al, *Proc Natl Acad Sci USA*, (1999) 96:4598-4603). Methods of packaging include using packaging cells that permanently express the envelope components, or by transiently transfecting cells with plasmids encoding the components of the vector, or by using an adenoviral system that encodes the components of the vector. Virus packaging cells and kits are commercially available, for example, from BD Sciences/Clontech in Mountain View, Calif.).

The pseudotyped virus of the invention can be used for diagnostic and therapeutic applications, as well as for research tool applications. Diagnostic applications include both in vitro, ex vivo, and in vivo uses, e.g., in vivo imaging. Therapeutic applications include both in vivo, in vitro, and ex vivo uses. For example, a virus particle of the invention can be administered to a subject via IV injection to treat or prevent cancers, e.g., breast, lung, ovarian, prostate, colon, lymphoma, leukemia, and melanoma; autoimmune disease such as myasthenia gravis, multiple sclerosis, systemic lupus erythymatosis, rheumatoid arthritis, and diabetes mellitus; infectious disease such as infection by HIV, HCV, HBV, CMV, and HPV; and genetic diseases such as sickle cell anemia, cystic fibrosis, Tay-Sachs, β-thalassemia, neurofibromatosis, polycystic kidney disease, hemophilia, etc. For in vivo applications, preferably the targeting moiety is covalently linked. The virus particles of the invention can also be administered ex vivo, e.g., to whole bone marrow by targeting CD34+ cells with the targeting moiety. In this embodiment, the targeting moiety can be covalently or non-covalently linked (e.g., via protein A or its ZZ domain). The virus particles can be used for diagnostic applications with heterologous marker genes, and can be used as research tools to transduce specific cell types. The targeted Sindbis envelope of the invention can also be used to target cell to cell interactions, by expressing the targeted envelope in a cell such as a lymphocyte, and then allowing the cell to contact the targeted cell in vivo, in vitro, or ex vivo.

The present invention also provides methods of purifying the virus from cells. In one embodiment, the virus is purified from cells by the following method: Virus is filtered through 0.22-microM-pore-size filter before concentration. Virus (30 mL) was loaded onto sucrose cushion (7 mL) and spinned using SW32 (Beckman) roter. 20% Sucrose (wt/wt) in 1×PBS with 1 mM EDTA was used for cushion. The spinning condition is 40000×g for 90 min at 4 degree. The supernatant is discarded and pellet is resuspended in 300 microL of Hanks Balanced Salt Solution. The concentrated virus is filtered again using same size filter before administration into animal.

The present invention also provides methods of transducing cells with the virus, as follows: some primarily hematopoietic cells are resistant to gene transduction (primary T cells and stem cell) in vitro. However changing the pH of the medium (7.4 to 5.5) during gene transduction makes gene transduction efficiency higher. (3-20 fold). This method is useful for ex vivo and in vitro transduction of some cell types.

Pharmaceutical Compositions and Administration

Pharmaceutically acceptable carriers are determined in part by the particular composition being administered (e.g., nucleic acid, protein, virus or transduced cell), as well as by the particular method used to administer the composition. Accordingly, there are a wide variety of suitable formulations of pharmaceutical compositions of the present invention (see, e.g., *Remington's Pharmaceutical Sciences,* $17^{th}$ ed., 1989). Administration can be in any convenient manner, e.g., by injection, oral administration, inhalation, transdermal application, or rectal administration.

In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Targeted Lentiviral Vectors with Mutated Sindbis Envelopes

Methods

Plasmid Construction.

All mutants of pIntron ZZ SINDBIS were generated using a site directed mutagenesis kit (Stratagene, La Jolla, Calif.). Initially, the envelope region of pIntronZZ SINDBIS was cloned into pBS-SKII. Mutagenesis was performed using various oligonucleotide corresponding to the mutations (Table 1) following the manufacturer's protocol. The mutations were confirmed by sequence analysis. The sequenced regions were then cloned back into pIntron ZZSINBIS. CCR MDRsc1 was constructed from pRRL-cPPTCMV-X-PRE (kindly provided by Dr. William Osborne) (Barry et al., *Hum. Gene Ther.* 12, 1103-1108 (2001)) and ha-MDRsc (kindly provided by Dr. Brian Sorrentino) (Bunting et al., *Blood* 92, 2269-2279 (1998)). FUhLucW was constructed from FUGW (kindly provided by Dr. David Baltimore) and pGL3-Basic (Promega, Madison, Wis.). FUIntronRW was constructed from FUGW and phRL-CMV (Promega).

flow cytometry. The clone designated B16F10 MDR5 showed the highest level of the expression of the MDR-1 gene and was used for all further experiments.

Virus Production.

All lentivirus vectors were produced by calcium phosphate-mediated transient transfection of 293T cells. 293 T cells ($1.8 \times 10^7$) were transfected with pCMVR8.2DVPR (12.5 µg), the appropriate lentiviral vector plasmid (12.5 µg), and pHCMVG (5 µg) or pIntron SINDBIS, pIntron ZZ SINDBIS or mutants derived thereof (10 µg). For in vitro screening of the mutant pIntron ZZ SINDBIS, TRIP GFP (kindly provided by Dr. Pierre Charneau) (Zennou et al., *Cell*, 101, 173-185 (2000)) was used as the lentiviral vector plasmid. CCRMDRsci was used as the lentiviral vector and pHCMVG as the envelope plasmid for generation of the MDR-1 expressing lentiviral vector. The *Renilla* luciferase expressing lentiviral vector was generated using FUIntronRW as the lentiviral vector plasmid and pHCMVG as the envelope plasmid. FUhLucW was used as the lentivirus vector for generation of the humanized Firefly luciferase expressing lentivirus vector.

Antibodies.

Anti-HLA ABC was purchased from Sigma (St. Louis, Mo.). Anti-P-gp (multiple drug resistant gene-1 product) was

TABLE 1

Sindbis Envelope Mutations

| Mutant | Domain | Details of mutation | *Selectivity Index 293T | *Selectivity Index HepG2 | **Titer (% of ZZ SINDBIS) 293T | **Titer (% of ZZ SINDBIS) HepG2 |
|---|---|---|---|---|---|---|
| ZZ SINDBIS | | | 9 | 4.9 | 100 | 100 |
| m1 | R1 | deletion of E3 a.a. 61-64 | 21 | 11.4 | 38 | 69 |
| m2 | R1 | E2 R1D | 7.5 | 4.6 | 85 | 97 |
| m3 | R1 | m1 + m2 | 21 | 9.8 | 30 | 64 |
| m9 | R1 | E3 RSKRS60-64AAAAA | 32 | 9.2 | 47 | 71 |
| m4 | R2 | deletion of E2 a.a. 68-71 | 11 | 5.3 | 30 | 59 |
| m8 | R2 | E2 SLKQ68-71AAAA | 17 | 5.7 | 101 | 78 |
| m5 | R3 | E2 S114P | *** | *** | *** | *** |
| m6 | R4 | E2 K159A E160A | 10 | 4.9 | 113 | 95 |
| m7 | R5 | E2 E216A T218A | 11 | 4.6 | 111 | 86 |
| 1st combination of mutations | | | | | | |
| ZZ SINDBIS | | | 34 | 6.9 | 100 | 100 |
| m1 | R1 | deletion of E3 a.a. 61-64 | 132 | 13.2 | 40 | 109 |
| m16 | R1 + 4 | m1 + m6 | 151 | 14.9 | 53 | 115 |
| m17 | R1 + 5 | m1 + m7 | 80 | 12.0 | 21 | 87 |
| m18 | R1 + 2 | m1 + m8 | 120 | 15.4 | 42 | 105 |
| 2nd combination of mutations | | | | | | |
| ZZ SINDBIS | | | 42 | 6.3 | 100 | 100 |
| m1 | R1 | deletion of E3 a.a. 61-64 | 127 | 14.8 | 68 | 133 |
| m168 | R1 + 2 + 4 | m1 + m6 + m8 | 125 | 18.6 | 89 | 143 |

The results are average of three independent infection and flow cytometry. a.a. is abbreviation of amino acid
*Selectivity index was calculated as follows: (% EGFP + cells infected in the presence of anti-HLA monoclonal antibody)/(% EGFP + infected in the absence of antibody)
**Titer $CO_2$. The virus was removed and replaced with fresh medium (1 ml). Three days post infection; the cells were trypsinized and analyzed by flow cytometry. Background infectivity of TRIP GFP (ZZ SINDBIS) was blocked by anti-Sindbis virus ascites fluid. Anti-Sindbis virus ascites fluid or control acites fluid was added to unconcentrated TRIP GFP (VSV-G), TRIP GFP (Sindbis) or TRIP GFP (ZZ SINDBIS) (0.1% volume) and incubated for 1 hour at 4° C. The virus was used for infection of 293T cells and infectivity was analyzed as previously described.

Immunoblot Assay.

The HIV vectors (FUhLucW) pseudotyped with ZZ SINDBIS or m168 were concentrated 100-fold by ultracentrifugation and resuspended in PBS. The concentrated virus was mixed with equal volume of electrophoresis loading buffer [glycerol (20%), β-mercaptoethanol (10%), sodium dodecyl sulfate (4%), Tris-HCl pH 6.8 (125 mM), bromophenol blue (0.02%)] and boiled for 5 min. The amount of virus sample was normalized to the amount of HIV p24 (5 μg of p24/lane). The samples were subjected to electrophoresis through an SDS polyacrylamide gel (10%) as described previously (Morizono et al., *J. Virol.*, September; 75. (17):8015-20. 75, 8016-8020 (2001)). Immunoblot analysis was performed with anti-Sindbis virus ascites fluid and horseradish peroxidase-conjugated anti-mouse antibody (Santa Cruz Biotechnology, Santa Cruz, Calif.). The protein bands were visualized by enhanced chemiluminescence (Pierce, Rockford, Ill.).

In Vivo Analysis of Background Infection.

HIV vector (FUhLucW) pseudotyped by VSV-G, Sindbis virus, ZZ SINDBIS or m168 were injected into the tail vein of 6-week old female NOD/SCID mouse. The amount injected for each virus was normalized to the amount of HIV p24 (30 pg of HIV p24 in 300 μl PBS). Five days post injection, the mice were anesthetized and injected with D-luciferin (3 mg/mouse) (Xenogen, Alameda, Calif.) intraperitoneally. CCCD images were obtained using a cooled IVIS CCD camera (Xenogen), and analyzed with IGOR-PRO Living Image Software. The data acquisition was performed 20 min after D-luciferin injection for 1 min. Mice were sacrificed by $CO_2$ narcosis after CCCD imaging. The organs from each mouse were excised and genomic DNA was isolated using a Dneasy kit (QIAGEN, Valencia, Calif.) following the manufacturer's protocol. Quantitation of the vector copy number and cell number in the DNA isolate was performed by using SYBRgreen real time PCR kit (QIAGEN) and an ABI PRISM 7700 sequence detector (Perkin Elmer, Wellesley, Mass.). The primers for the analysis of vector copy number (Firefly Luciferase) were Fluc-a (gagatacgccctggttcctg; SEQ ID NO:13) and Fluc-b (gcatacgacgattctgtgatttg; SEQ ID NO:14). The standard for quantitation of vector copy number was FUhLucW. The primers for the analysis of cell number (mouse beta actin) were beta-actin-F (caactccatcatgaagtgtgac; SEQ ID NO:15) and beta-actin-R (ccacacggagtacttgcgctc; SEQ ID NO:16). The standard for the analysis of cell number was made using genomic DNA isolated from normal mouse peripheral blood mononuclear cells.

Targeted Infection of Melanoma Cells In Vitro.

B16F10MDR5 cells ($1\times10^4$) were seeded on 48-well plate at the day before infection. The cells were incubated with FUhLucW (ZZ SINDBIS) or FUhLucW (m168) (10 ng HIV p24) with or without anti-P-gap antibody (1 μg/ml) for 2 hours at 37° C. with 5% $CO_2$. The virus was subsequently removed and replaced with fresh medium (500 μl). Three days post infection, cells were lysed in passive lysis buffer (Promega) and Firefly luciferase activity was measured following the manufacturer's protocol.

Targeted Infection of Melanoma Cells In Vivo.

To express *Renilla* luciferase as a marker, the human P-gp expressing mouse cell line, B16F10MDR5, was transduced by the lentiviral vector FUIntronRW (VSV-G). One day prior to subsequent cell and virus injection, TMbeta-1 (1 mg) was injected into 6-week old female NOD/SCID mice. *Renilla* luciferase expressing B16F10MDR5 ($2\times10^5$ cells in 150 μl of PBS) were injected into mouse via the tail vein. Thirty minutes later, FUhLucW (ZZ SINDBIS) or FUhLucW (m168), to which we had added anti P-glycoprotein monoclonal antibody or Isotype (IgG2a) control antibody (10 μg/ml) was injected into the tail vein. The amount of each virus used for injection was normalized to the amount of HIV p24 (36 pg of HIV p24 in 150 μl PBS). Ten days after cells and virus injection, lung metastasis of B16F10MDR5 was determined by imaging the *Renilla* luciferase. Mice were anesthetized and coelenterazine (20 μg) (Prolume, Pinetop, Ariz.) was injected via the tail vein. Data acquisition was performed directly following coelenterazine injection for 1 min. Twelve days after cell and virus injection, virus infection was determined by imaging the expression of Firefly luciferase reporter gene. Mice were anesthetized and injected intraperitonially with D-luciferin (6 mg/mouse). Imaging was performed as previously described. Mice were sacrificed after imaging using D-Luciferin. To isolate tumor cells, whole lung was isolated, ground and passed through a cell strainer (BD, San Jose, Calif.). The cells were cultured for 10 days in DMEM supplemented with FCS (20%), penicillin (100 units/ml) and streptomycin (100>ag/ml). Cultured cells were trypsinized, counted, stained by anti-P-Glycoprotein monoclonal antibody conjugated to PE (BD) and analyzed by flow cytometry. More than 99% of cells expressed P-gp demonstrating that nearly all of the cells we harvested were B16F10MDR5 cells. Cells were not recovered from control mice that did not receive tumor cells. One million cells were then harvested and lysed in passive lysis buffer (200 μl) (Promega) and analyzed for Firefly luciferase activity following the manufacturer's protocol. Genomic DNA was isolated using a DNeasy kit (QIAGEN). The primers and standard for quantitation of vector copy number were the same as those used to quantitate the background level of infection as previously described. Quantitation of the cell number was performed using primers for murine beta-actin as described above and the standard was generated by using known numbers of B16F10MDR5 cells.

Results

Figure 1:
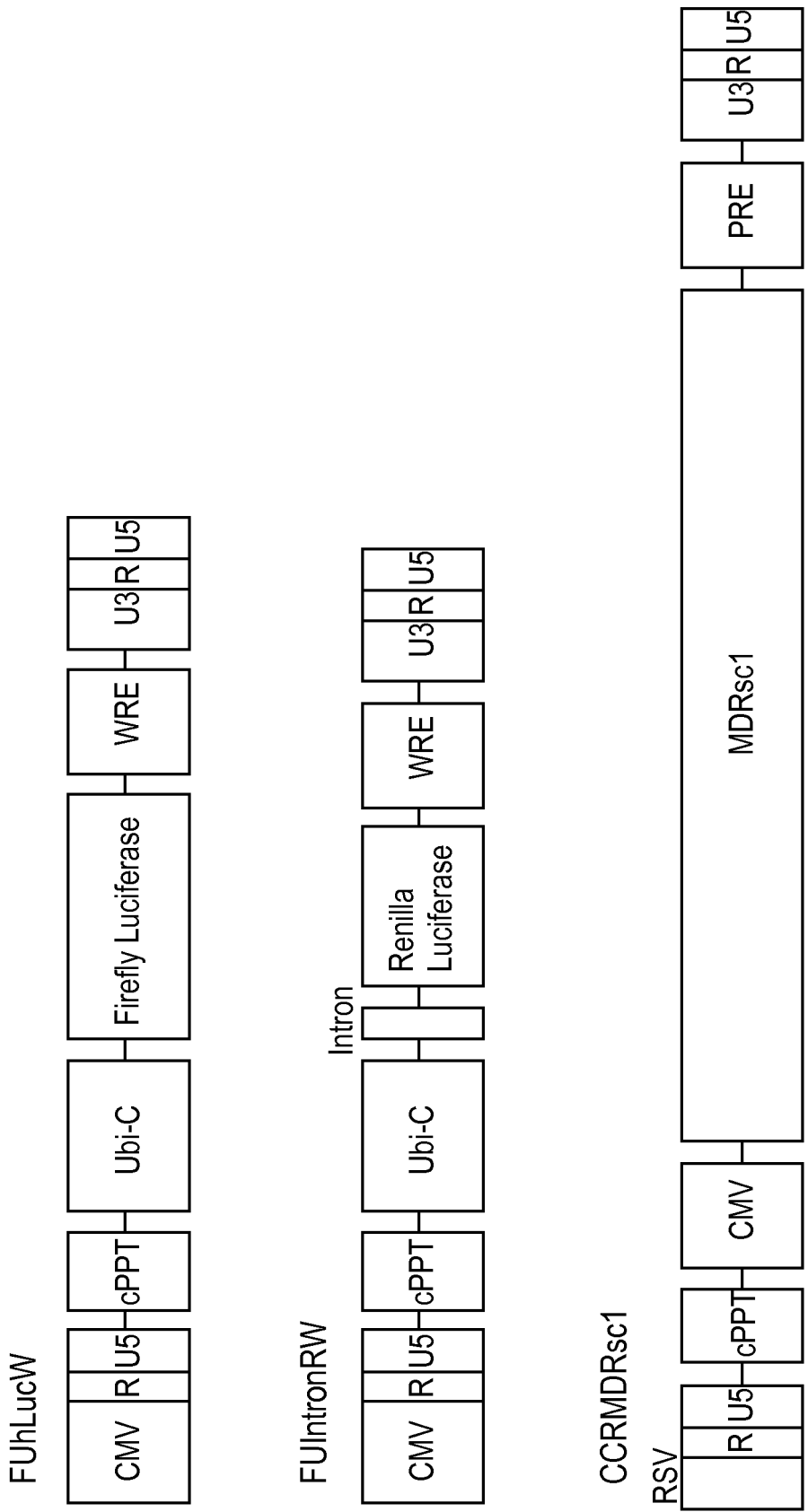
FIG. 1. Schematic representation of FUhLucW, FUIntronRW and CCRMDRsc1. FUhLucW and FUIntronRW have the CMV enhancer and CCRMDRsc1 has the RSV enhancer/promoter substituted for the U3 region of the 5' LTR. AU3 denotes a deletion in the U3 region of the 3' LTR that renders the 5' LTR of the integrated provirus transcriptionally inactive. FUhLucW and FUIntronRW have the Ubiquitin-C promoter as an internal promoter to express humanized Firefly luciferase or humanized *Renilla luciferase* respectively. CCRMDRsc1 has the CMV promoter as internal promoter to express MDRsc1 (P-glycoprotein). All vectors have the central polypurine tract (cPPT). FUhLucW and FUIntronRW contain the Woodchuck hepatitis virus post transcriptional element (WRE). CCRMDRsc1 has the human hepatitis virus post-transcriptional element (PRE). FUIntronRW has a chimeric intron derived from phRL-CMV.

We previously demonstrated specific targeting of our ZZ SINDBIS lentiviral vector and murine retroviral vectors to $CD4^+$ and $HLA^+$ cells using monoclonal antibodies specific for CD4 and HLA (Morizono et al., *J. Virol.*, September; 75. (17):8015-20. 75, 8016-8020 (2001)). These vectors demonstrated an approximately 30-fold selectivity for infection of target cells in the presence of the specific cell surface monoclonal antibody. Our goal is to utilize these vectors for direct targeting of gene therapy vectors to specific target cells via direct injection in the bloodstream. We utilized lentiviral vectors bearing two distinct types of reporter genes to assess transduction efficiency (FIG. 1). The EGFP-expressing virus vector allowed a quantitative assessment of infectivity in vitro as monitored by flow cytometry (Zennou et al., *Cell*, 101, 173-185 (2000)). We utilized both Firefly and *Renilla* luciferase-expressing virus vectors and non-invasive cooled charged-coupled device (CCCD) imaging to quantitate the level of specific targeting of vectors in live mice (Bhaumik and Gambhir, *Proc Natl. Acad. Sci. U.S.A.* 99, 377-382 (2002)).

HIV Vector Pseudotyped by ZZ SINDBIS has Non-Specific Infectivity In Vivo.

FIG. 2a shows the typical enhancement in infectivity of the ZZ SINDBIS pseudotyped virus vector in vitro using a monoclonal antibody directed to HLA. We observed approximately a 30-fold enhancement of EGFP+ cells in the presence of anti-HLA antibody relative to that seen in the absence of monoclonal antibody. As a comparison, VSV-G envelope pseudotyped virus infected cells at a high level in the absence of antibody. The titer of ZZ SINDBIS virus is usually about 5-fold lower than that of VSV-G pseudotyped virus but, like VSV-G pseudotypes can be further concentrated at least 100-fold by ultracentrifugation.

ZZ SINDBIS pseudotyped virus vectors expressing Firefly luciferase were utilized to quantitate the level and specificity of targeting in transduced cells in the organs of live mice. We used a lentiviral vector containing the Ubiquitin-C promoter for in vivo experiments since this vector has been shown to express well in all mouse tissues (Lois et al., Science, 295, 868-872 (2002)). ZZ SINDBIS virus vectors were injected into the tail vein in the absence of monoclonal antibody. The expression of virus was monitored by luciferase expression utilizing CCCD imaging (FIG. 2b). Lentiviral vectors pseudotyped with each of the envelopes, VSV-G, wild type Sindbis, and ZZ SINDBIS infected both liver and spleen. VSV-G and wild type Sindbis pseudotypes resulted in a strong signal. Although ZZ SINDBIS gave a weaker signal, consistent with its infectivity in vitro, there was still clear expression in liver and spleen. Injection of recombinant luciferase did not show a signal in major organs, indicating that the signal observed with ZZ SINDBIS was due to infection of cells in the organs (data not shown). We verified infection of Sindbis and ZZ SINDBIS in the liver and spleen by quantitative DNA PCR analysis (Table 2).

TABLE 2

Copy Number of Lentiviral Vector/$10^4$ Cells

| Vector | Liver | Heart | Spleen | Kidney | Lung | Ovary |
|---|---|---|---|---|---|---|
| No vector | *< | *< | *< | *< | *< | *< |
| SINDBIS | 569 | *< | 1407 | *< | *< | *< |
| ZZ SINDBIS | 75 | *< | 538 | *< | *< | *< |
| ZZ SINDBIS | 397 | *< | 520 | *< | *< | *< |
| ZZ SINDBIS | 146 | *< | 295 | *< | *< | *< |
| m168 | 26 | *< | 36 | *< | *< | *< |
| m168 | 66 | *< | 15 | *< | *< | *< |
| m168 | 38 | *< | 28 | *< | *< | *< |

Genomic DNA from each organ was isolated and analyzed as described in materials and methods.
*< represents undetectable
The threshold for the copy number for detection from each organ was as below.
Liver: 11 copies/$10^4$ cells.
Heart: 26 copies/$10^4$ cells.
Spleen: 3 copies/$10^4$ cells.
Kidney: 3.3 copies/$10^4$ cells.
Lung: 8.3 copies/$10^4$ cells.
Ovary: 13 copies/$10^4$ cells.

The Non-Specific Infectivity of ZZ Sindbis Pseudotypes is Due to Sindbis Envelope Sequences.

Figure 3:
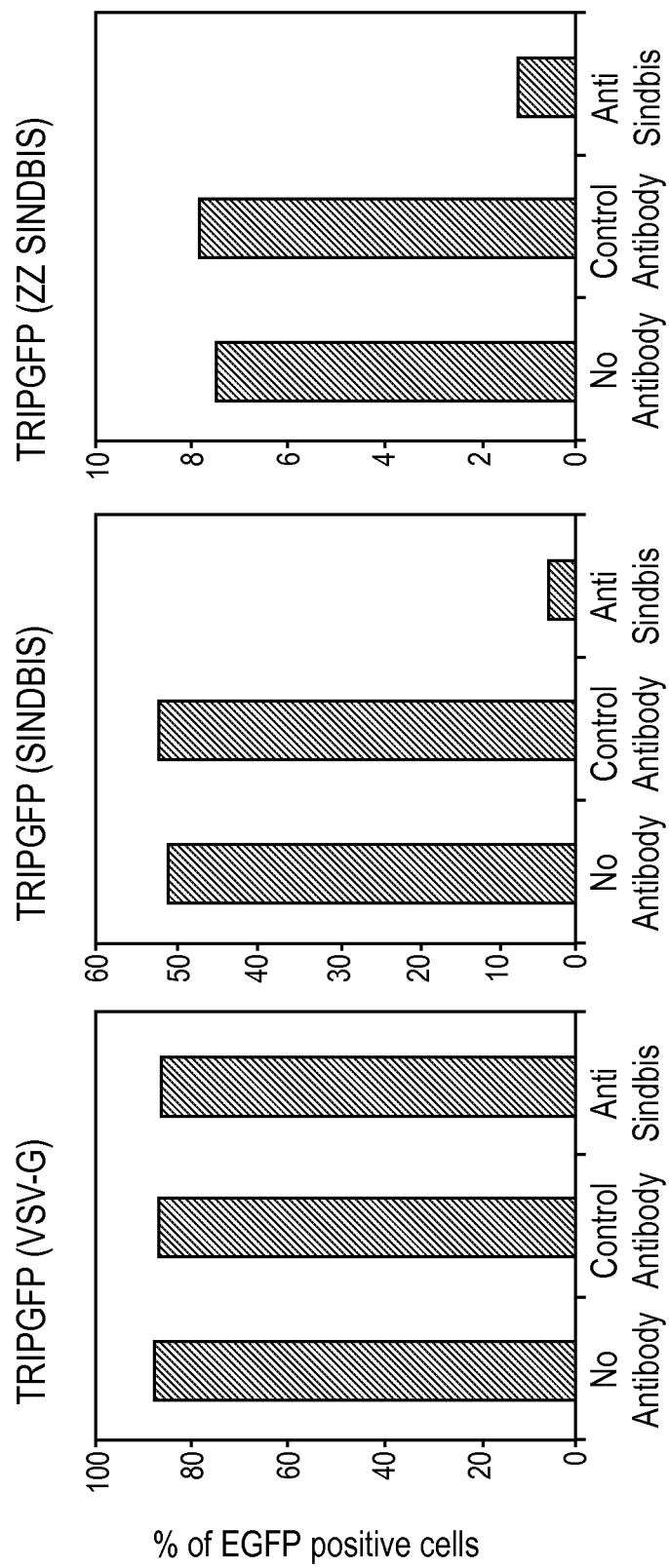

We further investigated the nature of the non-specific background infectivity of ZZ SINDBIS pseudotypes. A mouse polyclonal antibody which neutralizes wild type Sindbis virus infectivity was utilized to demonstrate that the background infectivity was the result of Sindbis virus domains and not the ZZ protein A sequences (FIG. 3). Using flow cytometry we determined that the level of GFP+ cells in the wild type and ZZ SINDBIS virus pseudotypes was substantially reduced in the presence of the anti-Sindbis antibody. Infectivity of VSV-G pseudotypes was not blocked nor was infection with the control antibody. These results indicate that Sindbis virus domains within the Sindbis virus envelope are responsible for the non-specific infectivity of ZZ SINDBIS pseudotypes. Thus, we undertook a structure-function analysis of the Sindbis virus envelope through site-directed mutagenesis of ZZ SINDBIS with the aim of ablating residual background infectivity.

Identification of a ZZ SINDBIS E2 Mutant with Enhanced Cell Targeting Specificity.

Figure 4:
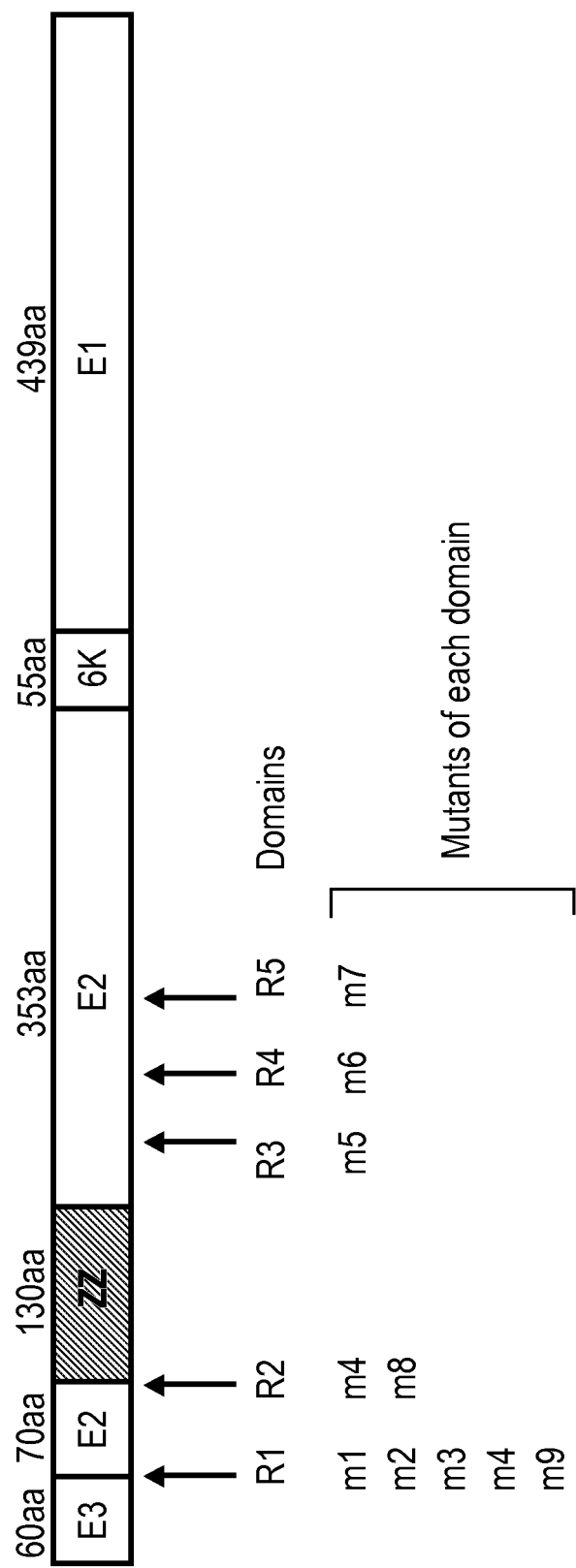

We first determined the regions responsible for the residual infectivity of our ZZ SINDBIS envelope. The domains we targeted for mutagenesis have previously been reported to affect binding to target cells, block epitopes for neutralizing antibody and function in Sindbis virus tropism (Klimstra et al., J. Virol. 72, 7357-7366 (1998); London et al., Proc Natl. Acad Sci U.S.A. 89, 207-211 (1992); Klimstra et al., J. Virol. 73, 6299-6306 (1999); Byrnes and Griffin, J. Virol. 74, 644-651 (2000); Pence et al., Virology 175, 41-49 (1990); Gardner et al., J. Virol 74, 11849-11857 (2000); Dubuisson and Rice, Journal of Virology 67, 3363-3374 (1993); Polo and Johnston, J. Virol. 65, 6358-6361 (1991); Lee et al., J. Virol. 76, 6302-6310 (2002)). All these domains were located in the E2 protein of the Sindbis virus envelope (FIG. 4). We analyzed E2 mutant pseudotyped virus vectors for infectivity in 293T cells using flow cytometry. The infectivity of mutants was tested on two different cell types, 293T, a human kidney cell line used for standard titration of virus stocks and HepG2 cells, derived from—a human hepatocellular carcinoma (Table 1). We tested infectivity in HepG2 cells, because of the background infectivity we observed in liver cells in vivo. We identified several E2 mutants with reduced levels of nonspecific infectivity and thus, an enhanced selectivity for targeting. Since some of these mutations also reduced the titer of viruses produced, we combined the mutations conferring enhanced selectivity with other mutations that enhanced infectivity. Five domains of Sindbis E2 previously reported to affect the infectivity of Sindbis virus were analyzed for their level of infectivity. Mutation m1 in domain R1 enhanced the selectivity on 293T cells relative to wild type ZZ SINDBIS virus. However, this mutation also resulted in a decrease in virus titer. Mutations in domain R4 enhanced the titer without altering the specificity. Combining mutation m1 and m6 resulted in partial restoration of the titer and maintenance of the higher selectivity of m1. A double mutant of m1 and m8 resulted in enhanced selectivity on HepG2 liver cells. The combination of mutations of m1, m6, and m8 in domains R1, R2, and R4, respectively, resulted in a pseudotyped virus with enhanced selectivity on 293T and HepG2 liver cells while maintaining stability during concentration by ultracentrifugation high viral titers. This mutant ZZ SINDBIS envelope was termed m168. Our data is consistent with previous studies that demonstrate the role of the R1 and R2 domains for heparin sulfate binding and the R5 domain for rescue of the reduced titer of an R1 mutant in replication competent Sindbis virus (Heidner et al., J. Virol. 68, 2683-2692 (1994)). Identification of a neurotropic strain of Sindbis virus suggested use of an alternative receptor in neuronal cells (Lee et al., J. Virol. 76, 6302-6310 (2002)). m168 also displayed a higher level of specificity than ZZ SINDBIS (>20-fold) in the neuroblastoma cell line, NB41A3 (data not shown).

Enhanced Specificity of the Modified m168 ZZ SINDBIS Pseudotyped Virus In Vitro.

Figure 5A:
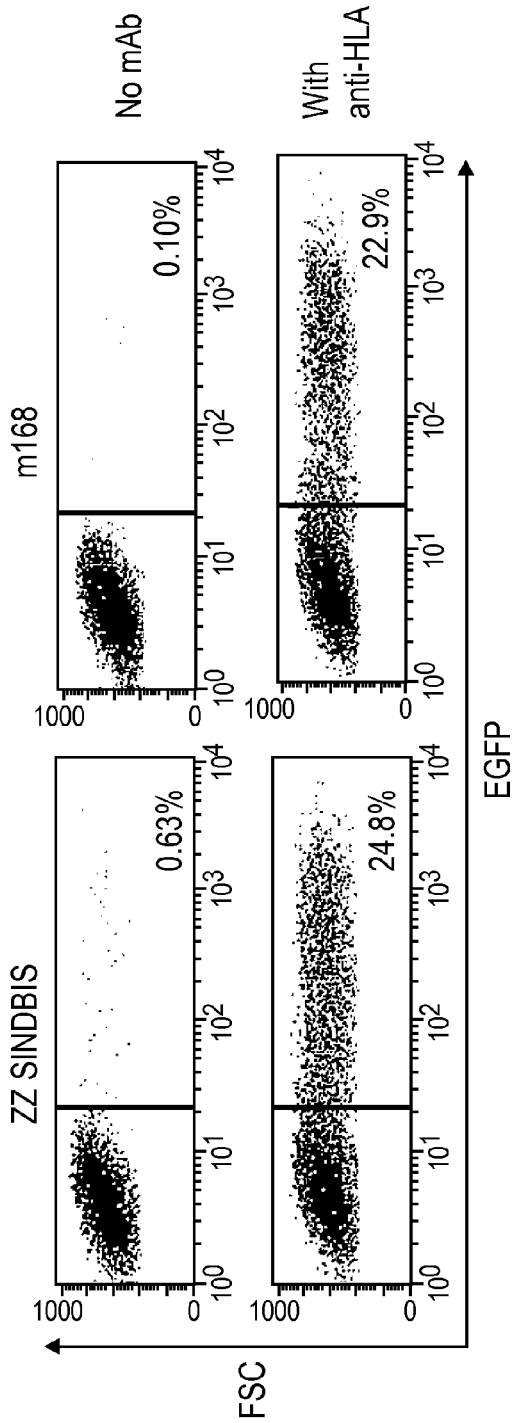
Figure 5B:
Figure 6:
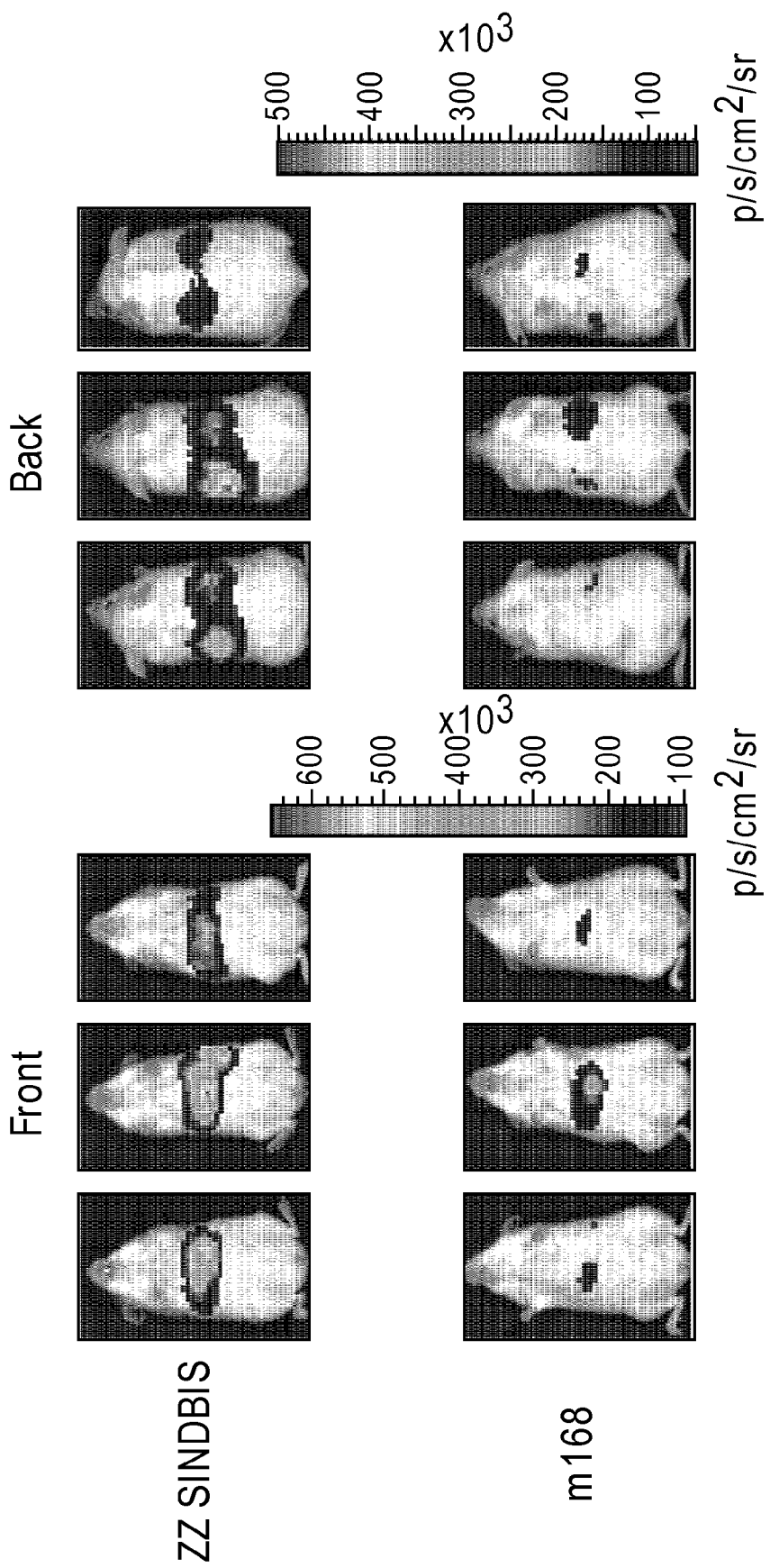

A representative experiment illustrating enhanced specificity of m168 infection in 293T cells, in the presence of an HLA monoclonal antibody is shown in FIG. 5a. In the absence of antibody the background level of infectivity is reduced when compared to the ZZ SINDBIS virus and the levels of infectivity and stability are maintained. A Western blot of m168 pseudotyped virions shows the E2 envelope protein expressed from wild type ZZ SINDBIS and m168 (FIG. 5b). Note that the m168 envelope protein is larger as a result of mutation m1 that prevents cleavage of E2 and E3. This mutant was used in subsequent experiments.

m168 ZZ SINDBIS Pseudotyped Virus Displays Reduced Non-Specific Infectivity in Mice.

The ultimate goal of these studies is to develop a gene transfer vector capable of delivery directly into the bloodstream to target specific tissues or cells. The ability of the genetically modified M168 lentiviral pseudotypes to infect target cells in live mice was tested. First, we determined the level of non-specific infectivity in the absence of targeting antibody. Viruses bearing luciferase reporter genes were injected via the tail vein into SCID mice and the location of the infectivity was assessed using a CCCD camera to determine the level of luciferase expression in the mice. Consistent with the in vitro results, the modified m168 ZZ SINDBIS pseudotyped virus displayed a substantially lower infectivity in the liver and spleen of inoculated animals, relative to the parental ZZ SINDBIS pseudotyped virus (FIG. 6). Because the intensity of the CCCD imaging for luciferase expression can be influenced by a number of variables such as depth of tissue and positioning of the animal during imaging, we confirmed these results by isolation of organs and PCR analysis for vector DNA sequences (Table 2). These results confirm that infectivity in liver and spleen is substantially reduced. Of note, we could not detect infection in ovaries indicating that transduction of our vector into germ line cells was unlikely to occur. Having successfully reduced the background infectivity, we tested the ability of these m168 pseudotypes to target cancer cells in the presence of monoclonal antibody directed to a tumor specific cell surface antigen, P-gp in mice.

m168 Virus Specifically Targets P-gp Expressing Melanoma Cells in NOD/SCID Mice.

Malignant melanoma is an aggressive human tumor that metastasizes to multiple tissues including remote skin, soft tissue, lympho node and lung (Allen and Coit, *Curr. Opin. Oncol.* 14, 221-226 (2002)). Several intrinsic properties of tumor cells contribute to the development of resistance to chemotherapeutic drugs. Increased expression of the multidrug resistant (MDR) genes causes overproduction of the transmembrane transport protein P-gp (Ambudkar et al., *Oncogene.* 22, 7468-7485 (2003)). P-gp transports neutral and cationic hydrophobic compounds across the cell membrane. Selection for tumor cells that are resistant to natural product amphiphilic anticancer drugs can induce expression of P-gp. Elevated levels of P-gp have been found in many solid tumors of the colon, kidney, liver and lung that had not been exposed to chemotherapy accompanied by development of the multi-drug resistance. One study demonstrated that 33 to 76% of the melanoma cell lines derived from primary tumors or metastases of untreated patients scored positive for P-gP (Berger et al., *Int. J. Cancer* 59, 717-723 (1994)).

We selected a murine model for human malignant metastatic melanoma where the tumor cells migrate through the bloodstream to engraft and form tumors in the lungs. We engineered the murine melanoma cells to express the human MDRsc1 gene (the vector is shown in FIG. 1) in order to provide a cell surface molecule for targeting. This served as our live animal model system that allowed us to stringently test whether our mutant E2 virus vector can target P-gp on the surface of the melanoma cells within live animals.

First, we demonstrated the specificity of the targeting for the P-gp expressing melanoma cells in vitro. A Firefly luciferase reporter gene was used to quantitate transduction of the melanoma cells by flow cytometry. Our results demonstrate that P-gp can be specifically targeted on the surface of the melanoma cells. In the presence of monoclonal antibody, infection of the melanoma cells is significantly greater than the original ZZ SINDBIS pseudotyped vector (Table 3). The P-gp transducing vector does not significantly infect cells that do not bear P-gp (data not shown). Thus, this combination of tumor cells and transducing vector was utilized for vector targeting in live mice.

TABLE 3

Luciferase Assay of Melanomas

| Virus | Antibody | RLU | Vector Copy#/ $10^4$ cells |
|---|---|---|---|
| §In vitro transduction | | | |
| — | — | <200* | |
| FUhLucW (ZZ SINDBIS) | — | 302 | |
| FUhLucW (ZZ SINDBIS) | Anti P-Glycoprotein | 1667 | |
| FUhLucW (m168) | — | 203 | |
| FUhLucW (m168) | Anti P-Glycoprotein | 1295 | |
| †In vivo transduction by systemic virus injection | | | |
| — | — | <200* | <19 |
| FUhLucW (m168) | control antibody | 405 | <19 |
| FUhLucW (m168) | control antibody | 233 | <19 |
| FUhLucW (m168) | control antibody | 296 | <19 |
| FUhLucW (m168) | Anti P-Glycoprotein | 2737 | 87 |
| FUhLucW (m168) | Anti P-Glycoprotein | 2397 | 50 |
| FUhLucW (m168) | Anti P-Glycoprotein | 3104 | 65 |
| FUhLucW (ZZ SINDBIS) | Anti P-Glycoprotein | 1834 | 77 |
| FUhLucW (ZZ SINDBIS) | Anti P-Glycoprotein | 115 | <19 |

Cells are harvested and analyzed for firefly luciferase expression and copy number of vector as described in materials and methods.
§The value of RLU for in vitro transduction is Relative Luciferase Unit/$10^4$ cells.
†The value of RLU for in vivo transduction is Relative Luciferase Unit/$10^3$ cells.
*The values of background (uninfected cells) ranged from 100 to 200.

The tumor cells were first marked in vitro by transducing with a vector expressing *Renilla* luciferase. This allowed us to differentially identify the location of vector expression in the tumor cells. The localization of vector expression and tumor cells in the mice was visualized using different substrates for the two luciferase genes, Firefly and *Renilla*, respectively (FIG. 7). Following injection, the tumor cells migrate to the lungs and can be visualized by CCCD imaging for *Renilla* luciferase. The virus bearing m168 and anti P-gp antibody was injected via the tail vein. Vectors injected in the absence of anti P-gp antibody, show no signal for Firefly luciferase. In contrast, when virus is pseudotyped with m168 bearing anti P-Gp antibody, the luciferase expression of Firefly luciferase (m168 virus vector) co-localizes in the lung with that of *Renilla* luciferase (tumor melanoma cells).

The co-localization in the lungs of Firefly and *Renilla* luciferase expression representing tumor and virus infection, respectively, was confirmed to be a result of infection of the melanoma cells by the targeting vector. Lung tissue was isolated and melanoma cells cultured. Firefly luciferase activity, representing expression from the vector, was observed predominately in those tumor cells isolated from animals in which anti P-gp targeted virus was used for the infection (Table 3). Quantitative real time PCR analysis confirmed these results. Interestingly, m168 pseudotype vectors demonstrate a higher level of infection in melanoma cells in vivo compared to the parental ZZ SINDBIS, most likely due to less nonspecific trapping in other mouse tissues.

The targeting of micrometastatic tumors was also visualized by immunohistochemistry (see, FIG. 10). Tumor micronodules are observed in the lungs at Day 6 following transplant with morphologic characteristics of melanoma and positive for melanoma antigen S-10037. About 1% of these nodules were also positive for EGFP, consistent with the previous PCR analysis (see, Table 2 of K. Morizono et al., Nature Med (2005) 11:346-352, hereby incorporated herein by reference in its entirety for all purposes).

Figure 11:
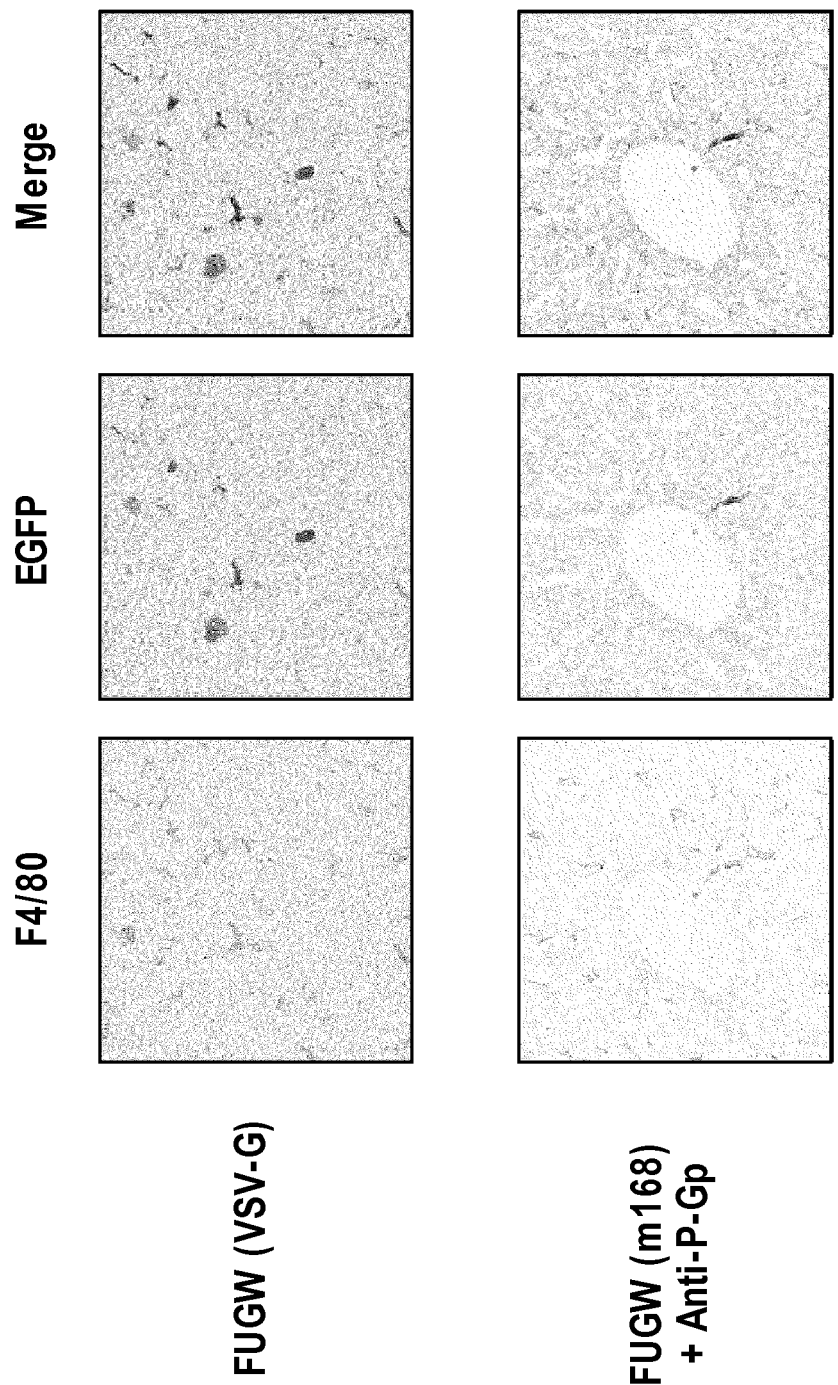

Rare transduced cells in the spleen and liver were identified as macrophages and related Kupffer cells, respectively, by flow cytometry and immunohistochemistry (FIGS. 11, 12a and 12b).

Targeting of Established Melanoma Tumors.

Figure 7:
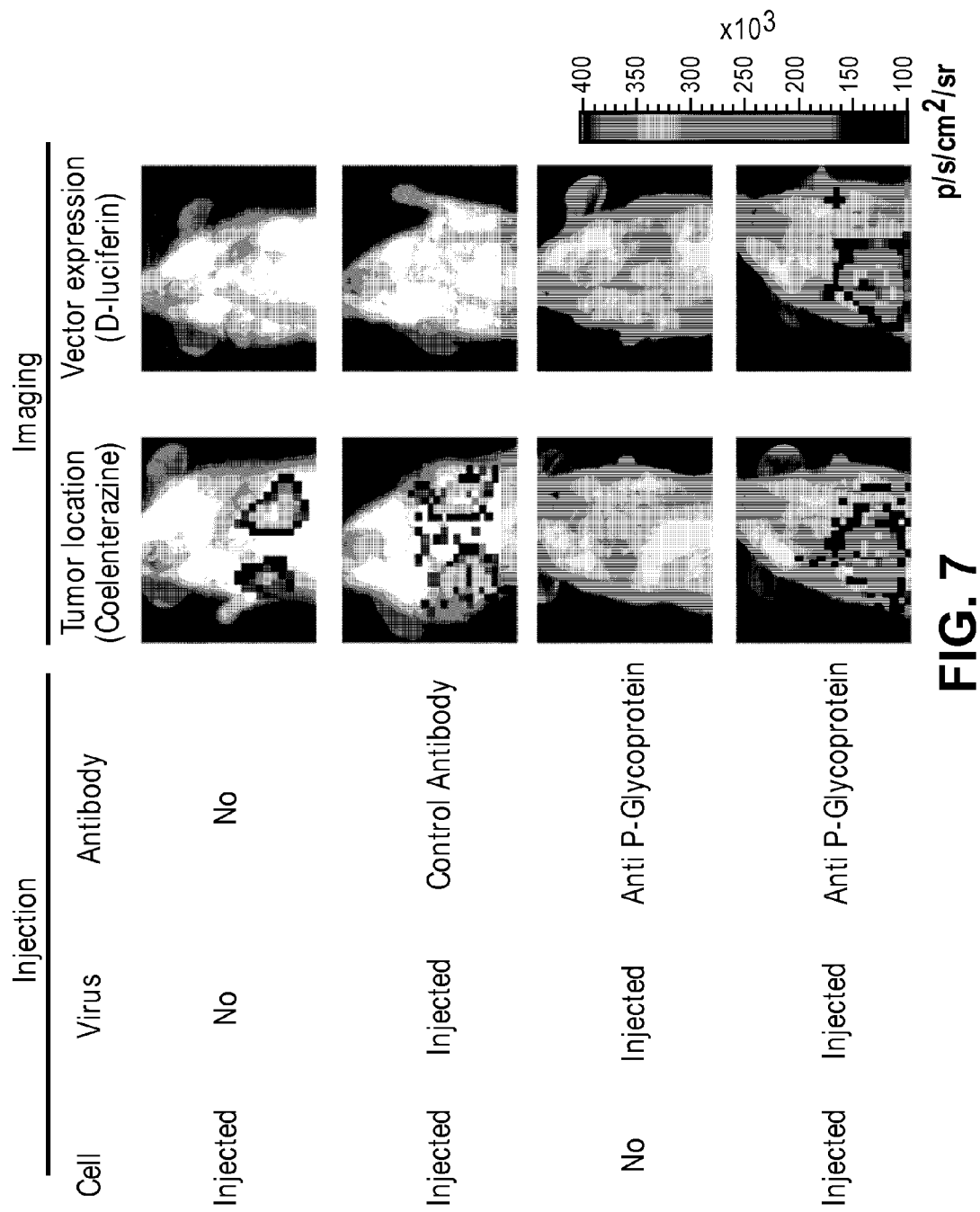
Figure 13A:
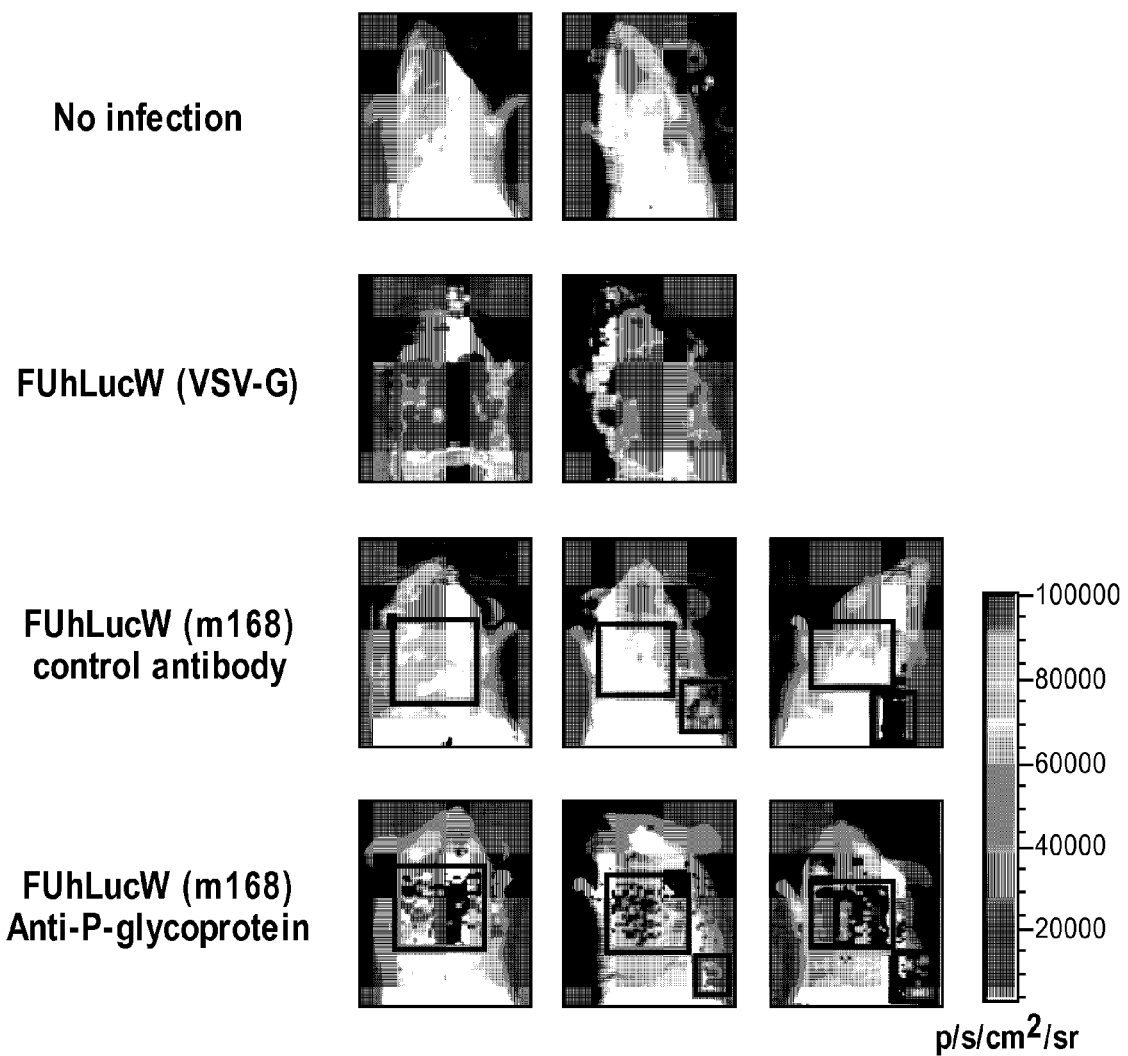
Figure 13B:
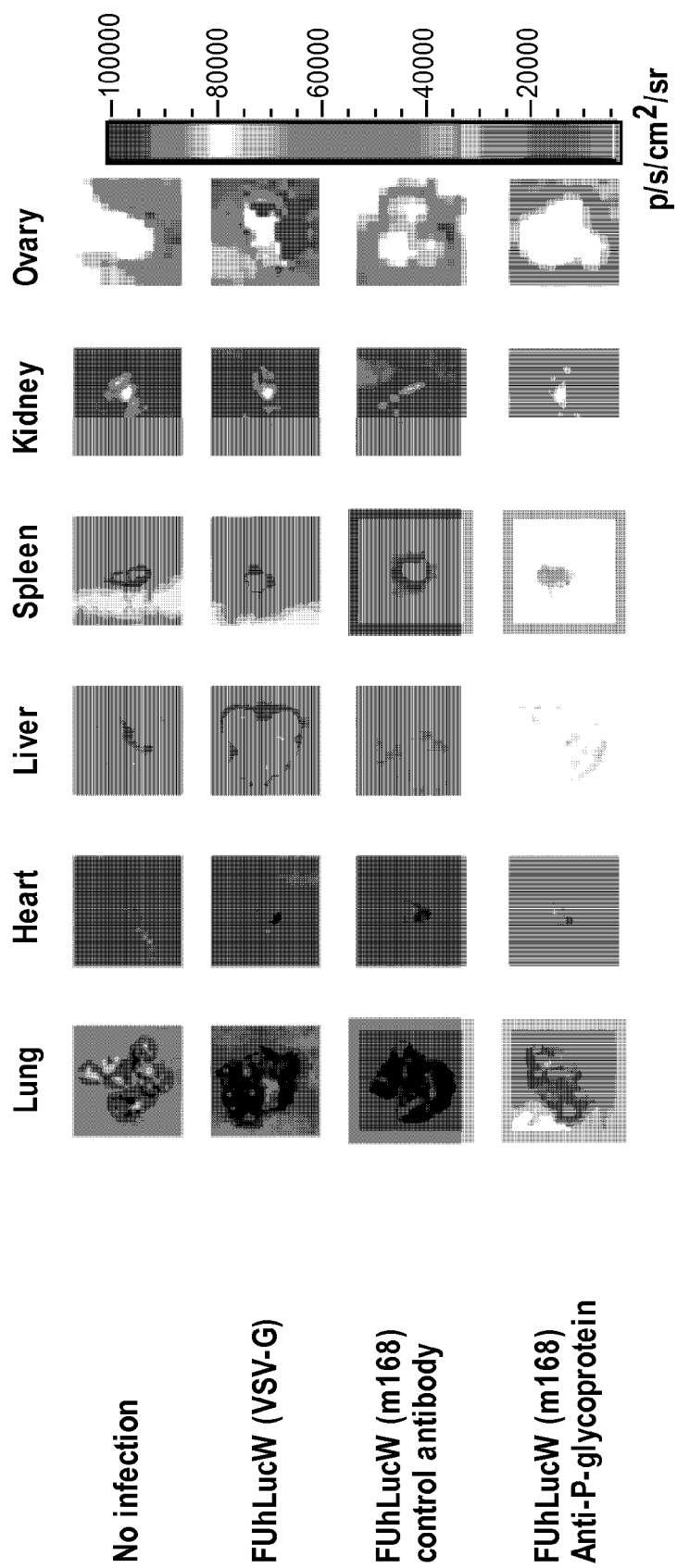

In another set of experiments, we tested the ability of the m168 vector to target established tumors. The same protocols as above were utilized except that tumors were allowed to form for 12 days prior to intravenous injection of the targeting vector. In this model system, visible tumors are evident at 8 days after inoculation and death occurs within 16 days after inoculation. Animals were visualized by CCCD imaging 3 days following intravenous injection for both the location of tumors and the specificity of targeting. Specific targeting to the tumors in the lungs of the animals was observed only following intravenous injection with m168 pseudotypes plus P-gp antibody (see, FIG. 13a). No non-specific infection was observed in the lungs in the absence of tumor and the infection to tumors in the lungs was dependent upon the presence of P-gp antibody. The transduction of organs was confirmed by isolation of specific organs following sacrifice (see FIG. 13b). The reduced signal intensity in lungs of this experiment relative to targeting of micrometastatic cells (compare mice of FIG. 13a with mice of FIG. 7) is due to limited growth of transduced cells (3 days versus 12 days after transduction) prior to imaging. For comparison, intravenous injection of VSVG pseudotypes show infection of a broad number of tissues without specificity for the tumors consistent with previously published studies (Sawai and Meruelo, *Biochem Biophys Res Commun* (1998) 248:315-323).

Discussion

We developed a gene therapy targeting strategy that for the first time allows production of a high titer virus that can be directed to specific cells and tissues. Most importantly, the high titer and specificity of this vector system makes it suitable for applications within living animals.

We took advantage of several aspects of the Sindbis virus envelope in designing our vector system. The Sindbis envelope consists of a cell derived lipid bilayer embedded with two integral membrane glycoproteins, E1 and E2, which mediate membrane fusion and receptor binding, respectively. Following binding of E2 to its receptor and endocytosis, E1 leads to fusion in a pH dependent fashion independent of E2. E1 and E2 are anchored in the cell membrane independently via transmembrane domains; an attribute that likely accounts for the high level of envelope stability and maintenance of function in chimeric molecules. Previous studies indicated that the Sindbis virus E2 envelope protein could be modified substantially yet retain infectivity (Dubuisson and Rice, *Journal of Virology* 67, 3363-3374 (1993)). Sindbis virus vectors with chimeric E2 envelopes were capable of targeting cells in vitro (Ohno et al., *Nat. Biotechnol.* 15, 763-767 (1997)).

Although Sindbis is an RNA virus, we previously created a DNA vector expressing the Sindbis envelope and demonstrated that it could be used to express functional envelope and form pseudotypes with both the HIV-1- and MuLV-based vectors (Morizono et al., *J. Virol.*, September; 75. (17):8015-20. 75, 8016-8020 (2001)). When the Sindbis virus envelope is modified to encode the ZZ domain of protein A, monoclonal antibodies directed to cell surface antigens can be used to redirect the target specificity of the retroviral vectors. Here, we substantially modified the Sindbis E2 envelope to further increase the specificity of infectivity to a degree sufficient to achieve the high level of specificity required for in vivo infection. In such a context, the virus would encounter multiple cell types and thus, an increased potential for non-specific infectivity. Although the parental (first generation) ZZ SINDBIS pseudotyped vector retains infectivity in the liver and spleen, the pseudotypes bearing modified Sindbis virus envelope show a substantially decreased level of infectivity in these organs.

Although we have not investigated the specific cellular receptors responsible for the non-specific infectivity of the parental ZZ SINDBIS virus, our results indicate that background infectivity is likely due to changes within the Sindbis envelope domains and not the ZZ domain. Some of the mutations we characterized are known to abolish binding of the Sindbis virus envelope to heparin sulfate and thus, are likely responsible for the decreased nonspecific infectivity and resultant enhanced selectivity of these viruses (Klimstra et al., *J. Virol.* 73, 6299-6306 (1999); Byrnes and Griffin, *J. Virol.* 74, 644-651 (2000)). The phenotypes of these mutants are consistent with a previous report that characterized the role of the heparin sulfate binding domain in non-specific transduction of a targeting adenovirus vector in mice (Smith et al., *Hum. Gene Ther.* 14, 777-787 (2003); Koizumi et al., *J. Viral.* 77, 13062-13072 (2003)). By reducing the non-specific infectivity, it was possible for us to redirect the target cell specificity of the virus to a specific human tumor cell antigen, P-gp, which is expressed on the surface of murine melanoma cells.

Once a melanoma acquires the ability to invade tissues, continue to proliferate and escape immune surveillance metastatic spread is likely to occur. Metastatic competent tumor cells migrate from the site of the primary lesion and subsequently grow at distant anatomical sites including the liver and lungs. Pulmonary metastases are the most common site of visceral metastasis with between 15% and 35% of recurrence occurring in this location (Allen and Coit, *Curr. Opin. Oncol.* 14, 221-226 (2002)). Only 4% of patients with pulmonary metastases survive 5 years. The murine melanoma model we chose to evaluate the specificity of our mutants mimics the progression of human melanoma to a metastatic stage often found in the lung. This system was ideal for testing specific targeting of our modified ZZ virus vectors to metastatic tumor cells by directly injecting them into the bloodstream of mice.

Targeting P-gp as a tumor antigen can be useful not only for metastatic melanoma, but for many other tumors, which express this gene and are thus rendered resistant to multiple chemotherapeutic drugs (Ambudkar et al., *Oncogene.* 22, 7468-7485 (2003)). However, P-gp is also expressed on some normal cells, thus the targeting of tumor cells that express P-gp would be most successful in those situations where the P-gp was significantly over-expressed in the tumor cells.

Although non-covalent interactions via the protein A ZZ domain would be useful in ex vivo applications, in an animal or patient with an immunocompetent humoral immune system, the presence of circulating antibodies would compete for the monoclonal antibodies of the targeting vector. Thus, clinical in vivo applications use chimeric, recombinant single chain antibody sequences or specific ligand and/or peptide sequences. Human chorionic gonadotropin sequences have been successfully recombined into chimeric Sindbis envelope to target Sindbis virus based vectors (Sawai and Meruelo, *Biochem. Biophys. Res. Commun.* 248, 315-323 (1998)). To date, we have tested these pseudotypes with over ten specific monoclonal antibodies. Any specific ligand or affinity reagent incorporated into the Sindbis envelope can be used to target a cell surface molecule specific to a given cell or tissue type.

The applications of a specific targeting gene therapy vector are broad. In the melanoma model, for example, one could introduce specific suicide genes to kill tumor cells and/or immunomodulatory genes to enhance immune response directed to metastatic legions. Early treatment of metastatic cells is of significant therapeutic value. In theory, metastases could be targeted well before they grow to a size to be visualized by current technologies. Residual tumor cells following localized treatment with radiation and/or surgery could also be targeted and eliminated.

The targeting of gene therapy vectors to specific cells and tissues at specific sites in the body has numerous applications. Current applications of gene therapy require either ex vivo purification of cells followed by transduction of the purified target cells and/or injection directly into localized sites, both of which require extensive technical manipulation (Kohn et al., *Nat. Med.* 1, 1017-1023 (1995); Cavazzana-Calvo et al., *Science* 288, 669-672 (2000)). Direct injection into the bloodstream and infection to specified regions would facilitate the application of gene therapy to many diseases. Since most diseases, both acquired and hereditary, either originate in specific cells or manifest their clinical phenotypes in specific tissues, the gene therapeutic vectors could be delivered where they would be most effective. For example, gene therapy utilizing hematopoeitic progenitor cells currently require purification of the hematopoeitic stem cells followed by transduction ex vivo. Specific targeting vectors can be developed that target antigens specific for hematopoeitic stem cells and thus, allow direct introduction of therapeutic genes into the stem cells through bone marrow and/or systemic injection after progenitor cell mobilization. As evidenced by our ability to target the melanoma tumor cells prior to establishment of visible tumors in the lungs, targeting vectors that circulate and home to specific cells could allow early therapeutic intervention in the case of diseases such as cancer, and residual cells of chronic or latent infections by infectious agents. This system could also be applied to treatment of pulmonary diseases such as cystic fibrosis and alpha-1 antitrypsin deficiency, caused by mutations in the CFTR (CF transmembrane conductance regulator) and alpha-1 antitrypsin genes respectively (West and Rodman, *Chest* 119, 613-617 (2001)). In principle, the CFTR and alpha-1 anti trypsin genes could be delivered efficiently to lung cells by a simple intravenous injection.

Finally, targeting of specific cells and tissues would greatly enhance the safety of gene therapeutic applications. Inappropriate expression due to inadvertent infection of irrelevant cells or tissues is one cause for concern in gene therapy applications and has resulted in serious adverse effects in some clinical trials (Lehrman, S., *Nature* 401, 517-518 (1999)). Targeting to specific cells would lessen the possibility of adverse side effects. In addition, insertional mutagenesis of the retroviral vector, if it does occur, would be limited to a much smaller subset of cells, thus diminishing the possibility of events leading to the initiation and/or progression of malignant transformation (Hacein-Bey-Abina et al., *Science* 302, 415-419 (2003)). It is important to note that this targeting system has broad applicability for use with other retroviral vectors. Although we utilized lentiviral vectors in this study, we previously demonstrated that the Sindbis ZZ pseudotypes will also form readily with MuLV vectors, more commonly utilized in most existing gene therapy clinical applications for a variety of diseases.

Example 2

Targeting Prostate Cancer Cells Through the Prostate Stem Cell Antigen (PSCA)

Prostate cancer is the most common cancer diagnosis and the second leading cause of cancer-related death in American men. Prostate cancer mortality frequently results from metastasis to bone and hormone-independent tumor growth. Physiologically relevant prostate cancer models exist, such as the LAPC-9 xenograft model (see, Craft, et al., *Cancer Res* (2000) 60:2541-2546). LAPC-9 cells were derived from a human bone metastasis, and are able to form a prostate cancer xenograft that can be propagated in SCID mice, and expresses prostate specific antigen and wild-type androgen receptor (Id.). Hormone independent outgrowths can be selected after castration of the mice, and micrometastasis can eventually be detected in half of the mice, recapitulating the clinical progression of human prostate cancer (Klein, et al., *Nature Med* (1997) 3:402-408).

Figure 14:
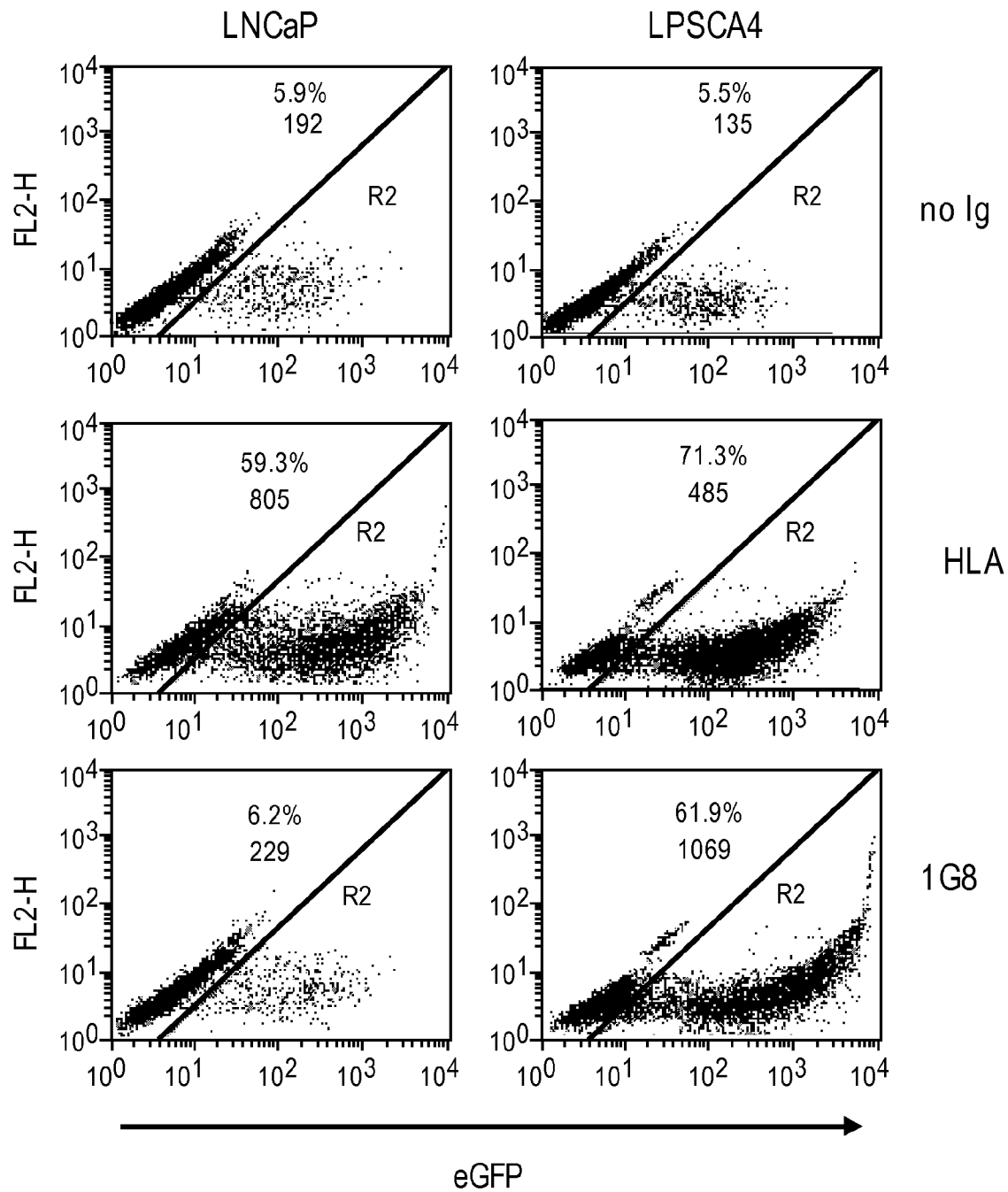

We generated vectors that specifically deliver genes to prostate cancer in a living animal, and validated our vectors in the LAPC-9 model system. First, we found a candidate surface molecule in prostate cancer cells that our engineered Sindbis envelopes could target. Prostate stem cell antigen (PSCA) is a prostate-specific gene with 30% homology to stem cell antigen 2, a member of the Thy-1/Ly-6 family of glycosylphosphatidylinositol (GPI)-anchored cell surface antigens. PSCA encodes a 123-aa protein with an amino-terminal signal sequence, a carboxyl-terminal GPI-anchoring sequence, and multiple N-glycosylation sites (Gu, et al., *Oncogene* (2000) 19:1288-96; and Reiter, et al., *Proc Natl Acad Sci USA* (1998) 95:1735-1740). PSCA mRNA expression is prostate-specific in normal male tissues and is highly up-regulated in both androgen-dependent and -independent prostate cancer xenografts. PSCA is expressed in over 80% of prostate cancers, among them the LAPC-9 xenograft (Saffran, et al., *Proc Natl Acad Sci* (2001) 98:2658-2663), and is a promising therapeutic target. Thus, we targeted Sindbis pseudotyped lentiviral vectors with an anti-PSCA mAb, 1G8 (Saffran, supra). Although PSCA is widely expressed in human prostate cancers, expression is very low or undetectable in prostate cancer cell lines. We obtained a LNCaP derivative cell line stably transfected with PSCA (R. Reiter, UCLA), LPSCA4, and analyzed the ability of 1G8 to mediate infection of FUGW (that expresses EGFP from ubiquitin C promoter) pseudotyped with m168 (FIG. 14). LPSCA4 was very effectively infected by FUGW with both αHLA and 1G8 antibodies, whereas the parental LNCaP cells could only be infected with αHLA. 1G8 did not mediate infection into LNCaP cells, as levels were comparable to background infection in the absence of targeting antibody.

Example 3

Combining Cell Surface Targeting with Selective Cell to Increase Efficiency of Specific Targeting The ubiquitin-C promoter in the FUGW lentiviral vector (Morizono, et al., *Nature Medicine* (2005) 11:346-352; and Lois, et al., *Science* (2002) 295:868-872), with a chimeric prostate specific antigen (PSA) promoter, designated (PSE-BC), to produce the construct FPGW. The key regulatory elements of the PSA enhancer include a proximal promoter (−541 to +12) comprising two binding sites for the androgen receptor (AREI and II) and a distal enhancer, which contains a 390-bp androgen responsive core region (Schuur, et al., *J Biol Chem* (1996) 8:1416-1426; and Cleutjens, et al., *J Biol Chem* (1996) 271:6379-6388). The core region contains a cluster of closely spaced androgen response elements (AREs) and sites for other transcription factors. The androgen receptor (AR) binds cooperatively to the enhancer and mediates synergistic transcription, and other factors within and outside of the enhancer contribute to prostate specificity (Reid, et al., *J Biol Chem* (2001) 276:2943-2952); and Huang, et al., (1999) *J Biol Chem* (1999) 274: 25756-25768). The PSE-BC promoter was generated by duplication of the PSA enhancer core and insertion of this duplicated element closer to the proximal promoter (200 bp upstream). After these modifications PSE-BC produced 20-fold higher expression levels than the parental construct, yet retained androgen inducibility and tissue specificity (Wu, et al, *Gene Ther* (2001) 8:1416-1426).

Figure 15B:
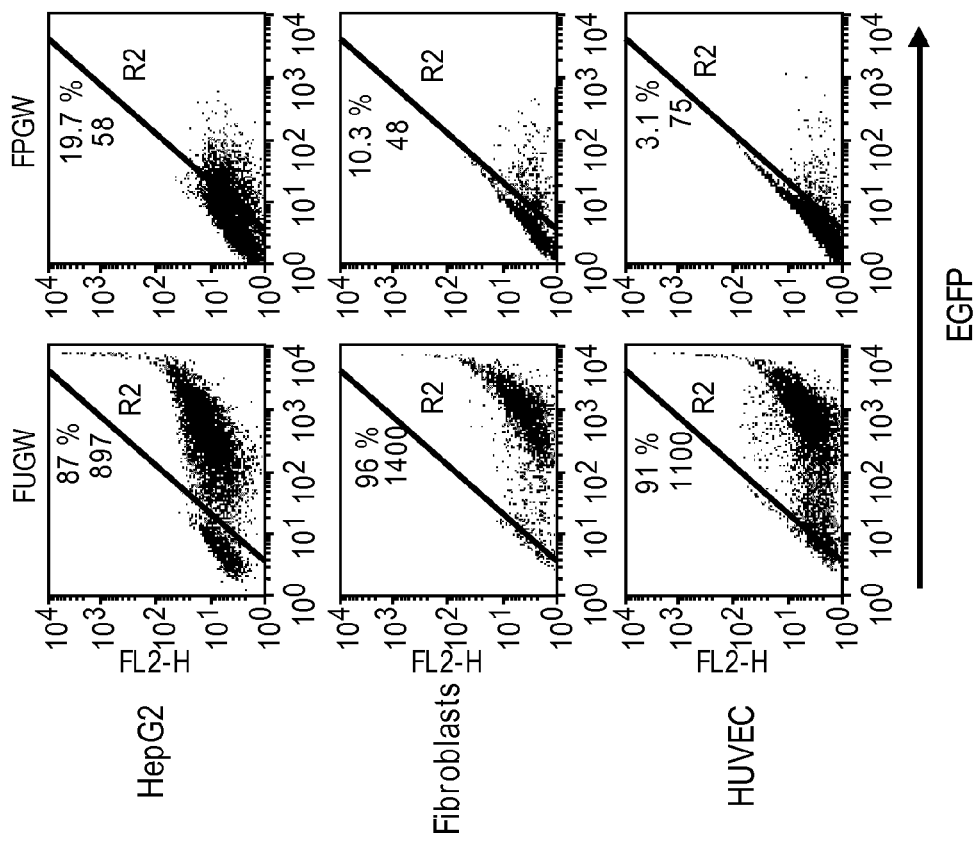
Figure 15A:
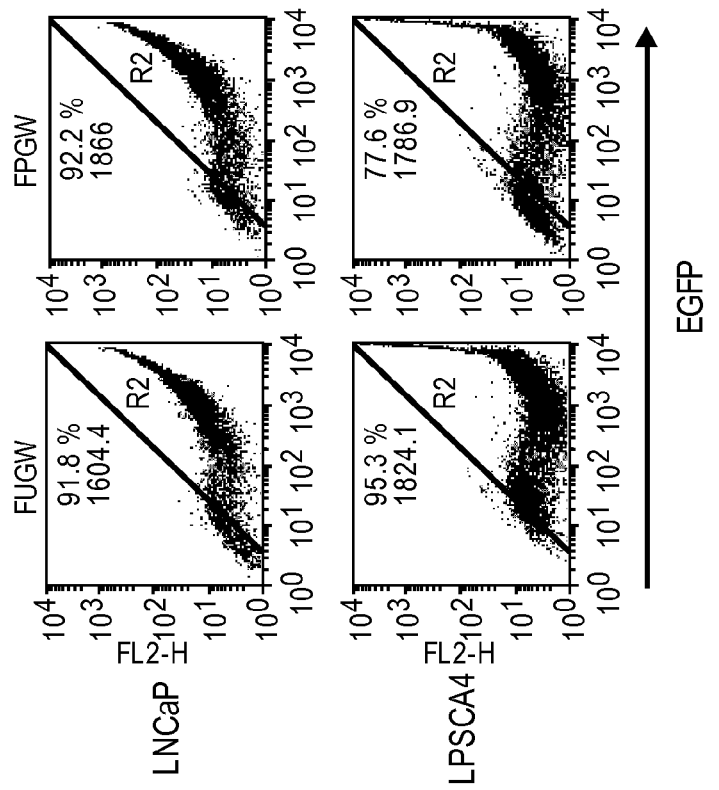

To assess the specificity of expression we infected prostate and non-prostate cell lines and primary cells with either FUGW or FPGW. Expression from the PSE-BC promoter was potent as the ubiquitin-C promoter in prostate cell lines, and specific to prostate cells, although some background expression could be detected in a hepatoma cell line (HepG2), primary fibroblasts and endothelial cells (FIG. 15). Of note, no expression from the PSE-BC promoter could be detected in primary macrophages in vitro.

Example 4

Targeting CNS Tissue by Conjugation to Anti-Transferrin Receptor Antibody

Successfully Targeted Transduction of Human Umbilical Vein Endothelial Cells (HUVEC) via TfR Using TfR Monoclonal Antibodies.

Transferrin receptor (TfR) is highly expressed on brain capillary endothelial cells and has been used by Pardridge and co-workers as a means to deliver therapeutic reagents into the brain (Pardridge, *Neuron* (2002) 36:555-558; and Pardridge, *Nat Rev Drug Discov* (2002) 1:131-139. We determined that TfR could serve as a receptor for targeted infection by testing infection with m168 pseudotypes conjugated with antibodies directed to human TfR expressed on human umbilical vein endothelial cells (HUVEC). There are several available monoclonal antibodies directed to different or unknown epitopes of TfR (Panaccio, et al., *Immunol Cell Biol* (1987) 65:461-472; Esserman, et al., *Blood* (1989) 74:2718-2729; and Takahashi, et al, *Blood* (1991) 77:826-832). Our results demonstrate successful infection of HUVEC with TfR antibody, but not in the absence of TfR antibody. However the levels of infectivity were low compared to targeting to other cell surface molecules such as CD4, HLA, and P-gp in other cell types. (FIG. 16)

It was reported that a single mutation within the E1 envelope protein renders Sindbis virus replication to be independent of a requirement for cholesterol (Lu, et al., *J Virol* (1999) 73:4272-4278). A similar mutation was also identified in Semliki Forest virus (Vashishtha, et al., *J Cell Biol* (1998) 140:91-99). The mechanism of this cholesterol independent replication is unclear. Since the E1 protein is responsible for fusion of Sindbis envelope to induce entry into the cell, we reasoned that this mutation in the context of our targeting vector would work in concert with antibody mediated binding to enhance the infectivity of the targeting viruses. Our results show that this is the case. Introduction of the cholesterol independent mutation (E1 AK226-227SG) into the targeting Sindbis envelope (termed 2.2) enhanced infectivity of lentiviral pseudotypes 8-fold over that of m168 pseudotypes targeted to TfR (FIG. 16). These results demonstrate that efficient targeting to TfR can be obtained in cell culture.

Targeting to the CNS in Living Mice.

Using the modified vector described above we tested its ability to target TfR, particularly TfR expressing cells of the brain capillary endothelium. Mice were injected intravenously with anti-TfR conjugated vector through the tail vein. Five (5) days after injection mice were analyzed for location of transduced cells by optical imaging for expression of the luciferase reporter gene. We observed a distribution of luciferase activity in the body consistent with successful targeting to the CNS. Intense optical signals were observed in regions corresponding to the brain and spinal column. These results were confirmed after sacrifice by removing the skin and muscle from the back of the animals confirming luciferase expression from the brain and spinal column (FIG. 17). Control mice injected with vector in the absence of TfR antibody did not show a signal in the CNS, consistent with typical control animals utilized in the experiments targeting P-gp on melanoma (Morizono, et al, supra). It is noteworthy that although TfR is expressed on multiple cells and tissues in the body (Gaffer, et al., *J Clin Pathol* (1983) 36:539-45; Lu, et al., *Acta Pathol Jpn* (1989) 39:759-764; and Soyer, et al., *J Cutan Pathol* (1987) 14:1-5), the major sites of transduction were observed in the regions corresponding to the central nervous system. Without being bound to any theory, this may be due to a higher density of transferrin receptor and/or enhanced rates of internalization of transferrin receptor in these regions (Pardridge, *Neuron*, supra; and Pardridge, *Nat Rev Drug Discov*, supra).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated pseudotyped retrovirus comprising mutant Sindbis virus E2 and E3 proteins, wherein the mutant Sindbis virus E2 protein comprises an IgG Fc binding ZZ domain polypeptide and the sequence SLKQ of a SINDBIS virus E2 protein is replaced with the sequence AAAA and wherein the mutant Sindbis virus E3 protein comprises a deletion of the sequence RSKR of a Sindbis virus E3 protein.

2. The isolated pseudotyped retrovirus of claim 1, further comprising a targeting moiety.

3. The isolated pseudotyped retrovirus of claim 2, wherein the targeting moiety is an antibody directed against a tumor specific cell surface antigen.

4. The isolated pseudotyped retrovirus of claim 3, wherein the targeting moiety is an antibody directed against p-glycoprotein.

5. The isolated pseudotyped retrovirus of claim 2, wherein the targeting moiety is an antibody directed against a tissue specific antigen.

6. The isolated pseudotyped retrovirus of claim 5, wherein the targeting moiety is an antibody directed against the transferrin receptor.

7. The isolated psuedotyped retrovirus of claim 1 further comprising a mutant Sindbis virus E1 protein wherein the mutant Sindbis virus E1 is the E1 protein encoded by SEQ ID NO:5.

8. The isolated psuedotyped retrovirus of claim 1 wherein the mutant E2 protein is the protein encoded by SEQ ID NO:3.

* * * * *